US006228597B1

(12) United States Patent
Parmentier et al.

(10) Patent No.: US 6,228,597 B1
(45) Date of Patent: May 8, 2001

(54) POLYPEPTIDES HAVING THYROTROPIN-RECEPTOR ACTIVITY, NUCLEIC ACID SEQUENCES CODING FOR SUCH RECEPTORS AND POLYPEPTIDES, AND APPLICATIONS OF THESE POLYPEPTIDES

(75) Inventors: Marc Parmentier, Brussels; Frederic Libert, St. Pieters-Leeuw; Jacques Dumont, Ohain; Gilbert Vassart, Brussels, all of (BE)

(73) Assignee: B.R.A.H.M.S. Diagnostica GmbH, Berlin (DE)

( * ) Notice: Subject to any disclaimer, the term of this patent is extended or adjusted under 35 U.S.C. 154(b) by 0 days.

(21) Appl. No.: 07/741,453

(22) PCT Filed: Dec. 12, 1990

(86) PCT No.: PCT/EP90/02154

§ 371 Date: Oct. 15, 1991

§ 102(e) Date: Oct. 15, 1991

(87) PCT Pub. No.: WO91/09121

PCT Pub. Date: Jun. 27, 1991

(30) Foreign Application Priority Data

Dec. 14, 1989 (EP) .................................................. 89403493

(51) Int. Cl.$^7$ ............................. G01N 33/53; C07K 1/00; C07H 21/00
(52) U.S. Cl. ................................ 435/7.1; 435/6; 435/7.2; 435/7.21; 435/69.1; 436/500; 436/518; 530/350; 530/854; 530/388.22; 530/387.9; 536/23.5
(58) Field of Search ............................ 435/7.1, 7.2, 7.21, 435/69.1, 172.3, 6; 436/500, 518, 539, 541, 548, 817; 530/350, 395, 413, 854, 388.22, 387.9; 536/27

(56) References Cited

U.S. PATENT DOCUMENTS 4,448,764 * 5/1984 Smith et al. .
5,144,007 * 9/1992 Pfahl .................................... 530/350
5,614,363 * 3/1997 Cone ........................................ 435/6

OTHER PUBLICATIONS

Nagayama et al., Mol. Endo. 6(2): 145–155, 1992.
Chan et al., Endrocrinology 120 (suppl.) T16 (Abstract 32), 1987.
Chan et al., J. Biol. Chem. 264(7): 3651–3654, 1989.
Frazier–Seabrook et al., Abstract 1072, Endocrine Society, 1989.
Rudinger J. Caracteristics of the amino acids as components of a peptide hormone sequence. Chapter 1 in "Peptide Hormones," edited by J. A.Parsons, University Park Press, Baltimore, pp. 1–7, 1976.*
Watson et al . The G–protein linked receptor facts book. Academic Press, San Diego p. 5, 1994.*
Costa et al. Immunohistochemiustry on whole mount preparations. Chapter 14 in "Immunohistochemistry" edited by A.C. Cuello John Wiley and Sons, New York, pp. 373–393, 1983.*
Harlow et al. Labeling of antibodies with iodine in "Antibodies a laboratory manual" Cold Sping Harbor Press, pp. 324–339, 1988.*
Koizumi et al Endocrinology 110 #4pp 1381–1391 (1982).*
Valente et al PNAS 79 pp 6680–6684 (1984).*
Massart et al Clin.Chem. 32/7, 1332–1335(1986).*
McFarland et al Science 245 pp 494–499 (1989).*
Frazier–Seabrook et al, Program 64$^{th}$ Meeting of American Thyroid Ass. Abstract T–51(1989).*
Bedin et al Mol. and Cellular Endicronology 65 pp 135–144(1989).*
Webster et al Cell 54 pp 199–207 (1988).*
Rees Smith et al Meth. Enx. 74 pp 405–420 (1981).*
Nagayama et al Biochem. and Biophy. Res, Comm. 165 #3 pp 1184–1190 (1989).*
Yoshida et al Clinical Research 36 3(1988) 610A "Molecular Cloning of a cDNA Encoding a Human Thyrotropin (hTSH) Receptor: Identification of Receptor mRNA in Thyroid and IM9 Lymphocytes".*
Young et al Proc.Natl. Acad. Sci. 80 (1983) pp. 1194–1198"Efficient isolation of genes by using antibody probes".*
Catty *Antibodies* vol. 1: *A Practical Approach* (1988) IRL Press Limited, pp 7–18.*

* cited by examiner

Primary Examiner—Jyothsna Venkat
Assistant Examiner—Joseph W. Ricigliano
(74) Attorney, Agent, or Firm—Pillsbury Winthrop LLP

(57) ABSTRACT

The invention concerns a polypeptide possessing thyrotropin receptor activity characterized in that it comprises the amino acid sequence shown in FIG. 11 (i.e., SEQ ID NO: 59) and cDNA molecules encoding this polypeptide. The invention also relates to vectors comprising cDNAs which encode the polypeptide of FIG. 11, cells transformed with these vectors, and the use the transformed cells expressing the thyrotropin receptor as in the detection of TSH or antibodies against the thyrotropin receptor.

11 Claims, 26 Drawing Sheets

FIG. 1

```
                3rd transmembrane segment
HGMP09     CDA  AGFFTVFASELSVYTLTAITL  ERWHTITHAMQLDCKVQLRHAASVMVMG-WIFAF
            *         *        *      *      *             *   *     *
M2HUM      CDL  WLALDYVVSNASVMNLLIISF  DRYFCVTKPLTYPVKRTTKMAGMMIAAA-WVLSF
M3HUM      CDL  WLALDYVVSNASVMNLLIISF  DRYFCVTKPLTYPARRTTKMAGLMIAAA-WVLSF
M1HUM      CDL  WLALDYVASNASVMNLLISF   DRYFSVTRPLSYRAKRTPRRAALMIGLA-WLVSF
M4HUM      CDL  WLAIDYVASNASVMNLLVISF  DRYFSITRPLTYRAKRTTKRAGVMIGLA-WVISF
A1ADRHAM   CDI  WAAVDVLCCTASILSLCAISI  DRYIGVRYSLQYPTLVTRRKAILALLSV-WVLST
D2R        CDI  FVTLDVMMCTASILNLCAISI  DRYTAVAMPMLYNTRYSSKRRVTVMIAIVWVLSF
B1ADRHAM   CEL  WTSVDVLCVTASIETLCVIAL  DRYLAITSPFRYQSLLTRARARGLVCTV-WAISA
B2ADRHUM   CEF  WTSIDVLCVTASIETLCVIAV  DRYFAITSPFKYQSLLTKNKARVIILMV-WIVSG
BADRHAM    CEF  WTSIDVLCVTASIETLCVIAV  DRYIAITSPFKYQSLLTKNKARMVILMV-WIVSG
RDC4       CDI  WLSSDITCCTASILHLCVIAL  DRYWAITDALEYSKRRTAGRAAVMIATV-WVISI
A2ADRHUM   CEI  YLALDVLFCTSSIVHLCAISL  DRYWSITQAIEYNLKRTRRRIKAIIITC-WVISA
G215HT1A   CDL  FIALDVLCCTSSILHLCAIAL  DRYWAITDPIDYVNKRTP-RPRALISLT-WLIGF
5HT1CRAT   CPV  WISLDVLFSTASIMHLCAISL  DRYVAIRNPIEHSRFNSRTKAIMKIAIV-WAISI
5HT2R      CAI  WIYLDVLFSTASIMHLCAISL  DRYVAIQNPIHHSRFNSRTKAFLKIIAV-WTISV
RDC8       CLF  FACFVLVLTQSSIFSLLAIAI  DRYIAIRIPLRYNGLVTGTRAKGIIAVC-WVLSF
RDC7       CLM  VACPVLILTQSSILALLAIAV  DRYLRVKIPLRYKTVVTPRRAAVAIAGC-WILSF
SKRBOV     CYF  QNLFPITAMFVSIYSMTAIAA  DRYMAIVHPFQP--RLSAPGTRAVIAGI-WLVAL
RDC1       CKI  THLIFSINLFGSIFFLTCMSV  DRYLSITYFASTSSRRKKVVRRAVCVLV-WLLAF
```

```
                                -20.                              1.
DOGTSH :         MRPPPPLLHLALLLALPRS-----LGGKGCPSPPCECHQEDDFRVT
RATHCG : MGRRVPALRQLLVLAVLLLKPSQLQSRELSGSRCPE-PCDCAPDGAL----
PIGHCG : MRRRSLALR--LLLALLLLPPPLPQT--LLGAPCPE-PCSCRPDGAL----
                *      *  **** *   * *      ** * *  ***   *
                            50.
DOGTSH : CKDIHRIPTLPPSTQTLKFIETQLKTIPSRAFSNLPNISRIYLSIDATLQ
RATHCG : ----RCPGPRAGLARLSLTYLPVKVIPSQAFRGLNEVVKIEISQSDSLE
PIGHCG : ----RCPGPRAGLSRLSLTYLPIKVIPSQAFRGLNEVVKIEISQSDSLE
             * *****   * *** ** ***** ** *   ** *    *
                            100.
DOGTSH : RLESHSFYNLSKMTHIEIRNTRSLTSIDPDALKELPLLKFLGIFNTGLGV
RATHCG : RIEANAFDNLLNLSELLIQNTKNLLYIEPGAFTNLPRLKYLSICNTGIRT
PIGHCG : KIEANAFDNLLNLSEILIQNTKNLLVYIEPGAFTNLPRLKYLSICNTGIRK
          *   *  **  * *  * ** ** *  * *  ** *** * *  **
                            150.
DOGTSH : FPDVTKVYSTDVFFILEITDNPYMASIPANAFQGLCNETLTLKLYNNGFT
RATHCG : LPDVTKISSSEFNFILEICDNLHITTIPGNAFQGMNNESVTLKLYGNGFE
PIGHCG : LPDVTKIFSSEFNFILEICDNLHITTVPANAFQGMNNESITLKLYGNGFE
          ***** *   ** ***** **  ** *  ****   *  *****  **
```

FIG. 2a

```
                       200.
DOGTSH : SIQGHAFNGTKLDAVYLNKNKYLSAIDKDAFGGVYSGPTLLDVSYTSVTA
RATHCG : EVQSHAFNGTTLISLELKENIYLEKMHSGAFQGAT-GPSILDISSTKLQA
PIGHCG : EIQSHAFNGTTLISLELKENAHLKKMHNDAFRGAR-GPSILDISSTKLQA
          ** ***** ** **  ***  * ** *   *  **** *******
                       250.
DOGTSH : LPSKGLEHLKELIARNTWTLKKLPLSLSFLHLTRADLSYPSHCCAFKNQK
RATHCG : LPSHGLESIQTLIALSSYSLKTLPSKEKFTSLLVATLTYPSHCCAFRNLP
PIGHCG : LPSYGLESIQTLIATSSYSLKKLPSREKFTNLLDATLTYPSHCCAFRNLP
         ***  **   **** ******  **   *    *   *********  
                       300.
DOGTSH : -KIRGILESLMCNESSIRSLRQRKSVN-TLNGPFDQEYEEYLGDSHAGYK
RATHCG : KKEQNFSFSIFENESKQCESTVRKADNETLYSAIFEENELSGWD------
PIGHCG : TKEQNFSFSIFKNFSKQCESTARRPNNETLYSAIFAESELSDWD------
           .  *    **   .  *   .   .   *                  
                       350.
DOGTSH : DNSQFQDTDSNSHYYVFFEEQEDEILGFGQELKNPQEETLQAFDSHYDYT
RATHCG : ---------------------------------------------YDYG
PIGHCG : ---------------------------------------------YDYG
                                                      ***

```
                    400.              I
DOGTSH  : VCGGNEDMVCTPKSDEFNPCEDIMGYKFLRIVVWFVSLLALLGNVFVLIV
RATHCG  : FCSPKT-LQCAPEPDAFNPCEDIMGYAFLRVLIWLINILAIFGNLTVLFV
PIGHCG  : FCSPKT-LQCAPEPDAFNPCEDIMGYDFLRVLIWLINILAMGNVTVLFV
HGMP09  :
          *        *    *       **.. **    ** . **

II    450.
DOGTSH  : LLTSHYKLTVPRFLMCNLAFADFCMGMYLLLIASVDLYTHSEYYNHAIDW
RATHCG  : LLTSRYKLTVPRFLMCNLSFADFCMGLYLLIASVDLYTHSEYYNHAIDW
PIGHCG  : LLTSHYKLTVPRFLMCNLSFADFCMGLYLLLIASVDAQTKGQYYNHAIDW
HGMP09  :                          IGIYLLLIASVDIHTKSQYHNYAIDW
          ***. *.*********.********  **  *

III          500.
DOGTSH  : QTGPGCNTAGFFTVFASELSVYTLTVITLERWYAITFAMRLDRKIRLRHA
RATHCG  : QTGSGCGAAGFFTVFASELSVYTLTVITLERWHTITYAVQLDQKLRLRHA
PIGHCG  : QTGNGCSVAGFFTVFASELSVYTLTVITLERWHTITYAIQLDQKLRLRHA
HGMP09  : QTGAGCDAAGFFTVFASELSVYTLTAITLERWHTITTHAMQLDCKVQLRHA
          ***  **  ****************  ******  **  .  ** ***

IV       550.
DOGTSH  : YAIMVGGWVCCFLLALLPLVGISSYAKVSICLPMDTETPLALAYIILVLL
RATHCG  : IPIMLGGWLFSTLIATMPLVGISNYMKVSICLPMDVESTLSQVYILSILI
PIGHCG  : IPIMLGGWLFSTLIAMLPLVGVSSYMKVSICLPMDVETTLSQVYILTILI
HGMP09  : ASVMVMGWIFAFAAALFPIFGISSYMKVSICLPMDIDSPLSQLYVMSLLV
            .*.**     .  *.* ** * *********   ** ** .
```

```
                                                       V                                         VI
DOGTSH  : LNIVAFIIVCSCYVKIYITVRNPQYNPGDKDTKIAKRMAVLIFTDFMCMA
RATHCG  : LNVVAFVVICACYIRIYFAVQNPELTAPNKDTKIAKKMAILIFTDFTCMA
PIGHCG  : LNVVAFIIICACYIKIYFAVQNPELMATNKDTKIAKKMAVLIFTDFTCMA
HGMP09  : LNVLAF
          **.***..... .***..* ** . ******..*******.*

650.  VII
DOGTSH  : PISFYALSALMNKPLITVTNSKILLVLFYPLNSCANPFLYAIFTKAFQRD
RATHCG  : PISFFAISAAFKVPLITVTNSKILLVLFYPVNSCANPFLYAIFTKAFQRD
PIGHCG  : PISFFAISAALKVPLITVTNSKVLLVLFYPVNSCANPFLYAIFTKAFRRD
HGMP09  :
          ****.*..** *.*********..******.******************. **

700.
DOGTSH  : VFILLLSKFGICKRQAQAYRGQRVSP----KNSAGIQIQKVTRDMRQSLP
RATHCG  : FLLLLSRFGCCKRRAELYRRKEFSAYTSNCKNGFPGASKPSQATLKLSTV
PIGHCG  : FFLLLSKSGCCKHQAELYRRKDFSAY---CKNGFTGSNKPSRSTLKLTTL
          .*** .*  **...***  ..*  *        **

DOGTSH  : NMQDEYELLENSHLTPNKQGQISKEYNQTVL
RATHCG  : HCQQPIPPRALTH
PIGHCG  : QCQYSTVMDKTCYKDC
          *
```

FIG. 2d

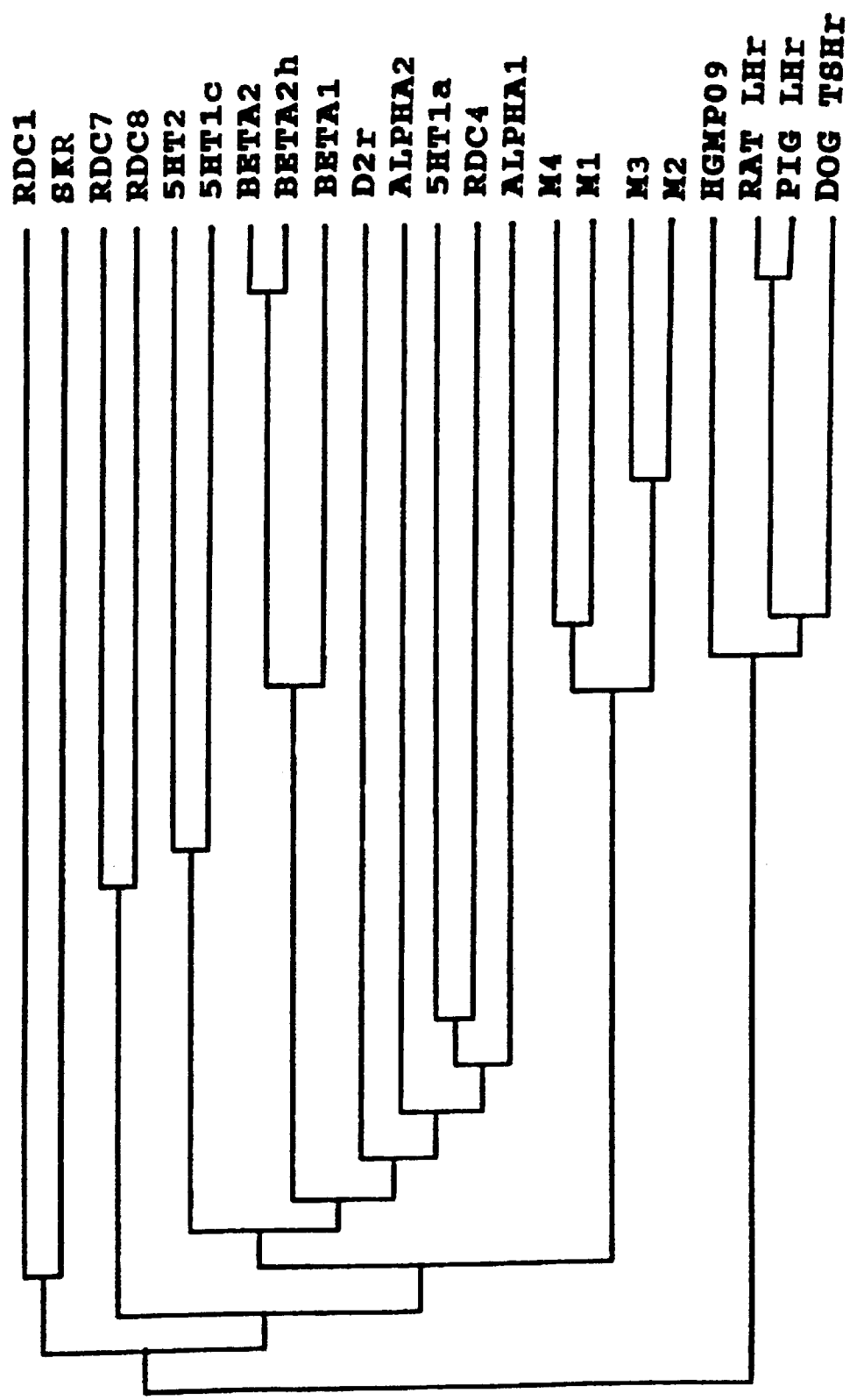

FIG. 5a

```
 -62                                                                CAGGGCGCAGAGGGGCCCAGAGACGACCGTGGAGGATGAAGAAATAGCCTTGGGACCCTTGGAAA
   1 ATGAGGGCCGCCCGCCCCTGCTGCACCTGGGCGCTGCTGTTCTCGCGGCTGGGAGCCTGGGGGGAAGGGTGTCCTTCTCCCCTGTGAG
  91 TGCCACCAGGAGGATGACTTCAGAGTCACCTGCAAGGATATCCACCGCATCCCACCCTACCACCCAGCACGCAGACTCTGAAGTTTATA
 181 GAGACTCAGCTGAAAACCATTCCTCCAGTCTGTGCATTTCAAATCTGCCCAATATTTCCAGGATCTGTCAATAGATGCAACTCTGCAG
 271 CGGCTGGAATCACATTCCTTCTACAATTAAGTAAAATGACTCACACATAGAGATTCGGAATACCAGAAGCTTAACATCATAGACCCTGAC
 361 GCCCTAAAAGAGCTCCCACTCTGAAGTTCCTTGGCATTTTCAACACTGGAGTATTCCCTGATGTGACCAAAGTTTATTCCACT
 451 GATGTATCTTTATACTGAAATCACAACAATGGCTTACTTCAAGGACAACAACCCTTCAATCCAAGGAGAGTGTACAGAAGCAACATGGGACAAACTGCTTCATGGGACAAACTG
 541 ACACTGAAACTATACAACAATGGCTTACTTCAAGGACAACAACCCTTCAATCCAAGGAGAGTGTACAGAAGCAACATGGGACAAACTG
 631 AAATACCTGTCAGCTATCGACAAAGATGCATTTGGGAGCATCTAAAGGAGCTGATAGCAAGCCAACACTGGACCAACCTTGCTGATGTCTCTTACACCAGTGTTACTGCC
 721 CTGCCATCCAAAGGCCTGACCTTTCTTATCCAAGCCTGCGCAGAAGGACAACTCTCAGTTGCTGTGCTTTTAAGAATACTTTGAATGCCCCTTTGACCAGGAATATGAAGAGTATCTG
 811 CACCTTACACGGGCTGACCTTTCTTATCCAAGCCTGCGCAGAAGGACAACTCTCAGTTGCTGTGCTTTTAAGAATACTTTGAATGCCCCTTTGACCAGGAATATGAAGAGTATCTG
 901 TGTAATGAAGAGCAGCCATGCTGGGTATTGGGAGCCTGCGCAGGACAACTCTCAGTTGCTGTTTAAGAATACTTTGAATGCCCCTTTGACCAGGAATATGAAGAGTATCTG
 991 GGTGACACAGCCATGCTGGGTATTGGGAGCCTGCAAGGACAACTCTCAGTTGCTGTTTCCAGGATACCAGCAATTCTCATTATTAGTCTCTTCGAAGAACAAGAA
1081 GATGAGACATCCTCGGTTTGGGCAGGAGCTTAAAAACCCACAGAAGAGACCCTCCAGGCTTTGATAGCCATTATGACTACACTGTGT
1171 GGTGGCAATGAAGACATGGTGTGTACTCCTAAGTCAGATCAGAGTTCAACCCTGTGAAGACATAATGGGCTACAAGTTCCTGAGGATTGTG
1261 GTGTGGTTTGTTAGTTCTGCAACTTGGCCTTTGCTGTCTCCTGGCTCTCCTGGGCAATGTCTTTGTCCTTACCAGTCACTACAAATTGACTGTCCCACGC
1351 TTTCTCAGTGCAACTGGCCTTTGCTGTCTCCTGGCTCTCCTGGCAGATTTCTGCATGGGGATGTATCGCTCCTCATGCCTGTAGACCTTCGCTCCTGCATTCTGAG
```

FIG. 5b

```
1441  TACTACAACCATGCCATCGACTGGCAGACAGGCCCTGGGTGTAACACAGTCTGGTTCTTCACTGTCTTTGCCAGTGAATTATCAGTGTAT
1531  ACACTGACAGTCATCACCCTGGAGCGCTGGTGTATGCCATTACCTTCGCCATGCCGCCTGGACAGGAAGATCCGCCTCAGGCATGCATATGCC
1621  ATCATGGTTGGGGCTGGGTTTGCTGCTTCGTGCTTCCTGCTCCGCCCTGCTCCTCGTGGGAATAAGCAGCTATGCCAAGGTCAGCATCTGCCTG
1711  CCCATGGACACTGAGACACCTCTTGCCCTGCCTGCATATATTATCCTTGTTCTGTTGCTCAACATAGTTGCCTTTATCATTGTCTGCTCCTGT
1801  TATGTGAAGATCTACATCACAGTCCGAAATCCCCAGTACAACCCGGGGACAAAGACACCAAAATTGCCAAAAGGATGGCTGTATTGATC
1891  TTCACTGACTTCATGTGCATGGCCCCCAATCTCATTCCTGTGCCAATCCATTTCTCTATGCCTTATGAACAAGCCTCTCATCACTGTACCAACTCCAA
1981  ATCTTGCTCGGTTCTCTTCTCACTTGAACTCGTGTAAACGCCAGGCATCAGGCTCAGGGCATACCGGGGCCAGCATACGGGGTTCTCCAAAGATAGTGCTGGTATTCAG
2071  ATCCCTGCTCAGCAAGTTTGGGCATCTGTAAACGCCAAGTCTCCCCAACATGAGGCAAGTCTCCCCAACAGTTCTGTAAGCAGCTGAACTGCTTGAAAACTCCCATCTAACCCAAAT
2161  ATCCAAAAGGTTACCCGGGACATGAGGCAAGTCTCCCCAACAGTTCTGTAAGCAGCTGAACTGCTTGAAAACTCCCATCTAACCCAAAT
2251  AAGCAGGGCCAAATCTCAAAAGAGTATAACCAAACAGTTCTGTAAGCAGCAGCTGACCTAACCCTTTGCAGGTGATGTTTCATGGGCAAATTCA
2341  TAGTTTCTTGAACACGTATTCCAAATTCATTATACACAAGACAGCTGACCTAACCCTTTGCAGGTGATGTTTCATGGGCAAATTCA
2431  TCTCCAAAAGGGGTAGCTCTACCACCTAATCATTACCTCCCAGAAGGAGAGGCTACCAGCACTTCTGAACCCTGGTGATATCAAG
2521  ATAACTGACACTTTCTAGAAAACTTGTTTGATGCTAACTGCTTAACAACATTGTATAAGCAAATGCTATTAACTGAGTTGGTGACCACAGGTC
2611  AACATTGAGCTTCTCACTTTCAAATAGCATTTCATGTGGAAGGTGAAGGAGGGAAAGGCTTAGTTGTTAGTTGTTATTTCAGCCTCTGAAACTATATCATCTCT
2701  GAATTAGCCCCACATGGCTTGGTCCACCTTCATGTTCTTGGATACAACAAAGAGAATGTGAATTCCTGAAACTGAAAAGTCCAGCAG
2791  GATACATGCATGAAGCAGCTATTATGAGGTGAAGGAGGGGAAAGGCTTAGTTGTTAGTTGTTATTTCAGCCTCTGAAACTATATCATCTCT
2881  TCACAAGGACCTACCTGATGTGACCCAACTGTTAGGTGTTGCCCAGGGGGAAAAAAACTGGCAAGATTTCAGCTTATGTGGCTGAGCAA
```

FIG. 5c

```
2971 AGTAAGAATTGTTCTTCTTGGCTAGTCTTATAGCATAAATACGTGAACCCTAGAAATATTTCTAAGTAGCAGCAAGTGGAATTATGAG
3061 CAGGGCACACTAAATCACACACTGATTAATAAAGCAGGGCCACAAGGTAACTGTTGGAGCTTGGGCAAATCACTGGGCCACTTCTAAGTC
3151 TAGAAATGAGAGAGCCTGATTGCTTCTTCAGTTTCAAAACTCTATGTATATCCCTTAAAATATGTTCCATGACAAAAAGAAA
3241 AGCACTAAAAAGAAAGAAAAGAAAAAGCACTAAGAAAGAAAAATTATTTTCCTATCTTGTAGTGCAGCCACCTCTTTCTCTTTGGAG
3331 GCTGGATATATGACCCAGGACATTTCTTTCTTTTTTTATTTTCATTTTTGATTATAATGTCTGATCCATGTTGGGCTGGATCT
3421 AAATCACTCAACTAATTACTAGATCTCTACAGCTACAATTATCAGGCCAAAACAGACTCATATTCACATAACAGAATAAAGGTGGTTT
3511 TGCAAATTTGGTTATTCAGAGTTACTCACTGTATAGATTAACTGTCCAGGGATTGGAAGCTATCAAACA
3601 CTCAGGCAAAGCAACACTAAAGCTATCAAGAGAAGTTTCTTCTCCAAACTGCTAGCCTTTTTCCAACCTGTTGATCATTGGACATAAT
3691 CTCTATTGCCCAATAGTGTTCTCTCTTACTTAAAATGGTTAGGATCAATCTTTAAATATAGACGTACTCTTCAGATTACCTGTCAAAACAGT
3781 CCCTTAATTTCCTCCCAAGCAGATGGCATTTGCTTCTCAATGTTCATGAGAAGCACACCAAGGAATTAGAAGCACCACCACTAGGATATCCCAACCACTGTTGTTTCAAGTC
3871 TGTGGAGTAGGGTTACTGGGCCCAATGCCCCCCCCCACAGAGATGTCCCCAACCACTCGAAATCATGACCACTCATGACTTATCCACCAGTTCACTGTAACTAATAAC
3961 CTGATTATCATTGAGATTGGACATCTTAGTAGAAATATTATACACACTCGAAATCATGACTTATCCACCAGTTCACTGTAACTAATAAC
4051 TAAACAGTTGTTGTTATCGTTTGGCATGTGTTTCTCACCTGTGACATTTGAAATAGTACATCCTGATAATGTATTTATCTTAAGTAGTT
4141 GAAATAACACTTTGGAAACCGTCCTAGAAAAGTAACTTCAACACAATTGTTACTAAAATTTGCATTCACAACATGAAATAAATTTCTTC
4231 CTATGAAATGATTGTGCTGAGTGCTGAGTCCTACAGTATGGCATTTGTGAGCTTCTTTTAATGTTACCGTTATATGTTACAACTGAA
4321 GACAGGGAAAAAAAAACAACTGGCAAATTTGCTAA
```

FIG. 7

```
 -20   MRPPPLLHLALLLALPRSLG
   1   GKGCPSPPCECHQEDDFRVTCKDIHRIPTLPPSTQT

37   LKF-IETQLKTIPSRAFSNLPNISR
  61   IYLSIDATLQRLESHSFYNLSKMTH     ˅
  86   IEIRNTRSLTSIDPDALKELPLLKF
 111   LGIFNTGLGVFPDVTKVYSTDVFFI
 136   LEITDNPYMASIPANAFQGLCNETL
 161   TLKLYNNGFTSIQGHAFNGTKLDAV
 186   YLN-KNKYLSAIDKDAFGGVYSGPT
 210   LLDVSYTSVTALPSKGLEHLKELIA
 235   RNTWTLKKLP-L-SLSFLHLTRADL....

Cons    L LIXX^N XXLX SIP SX^A FXGLXXXXX
        I       T        ALD  S
```

FIG. 8a

Comparison of human and dog TSH receptor sequences

```
              -20                  1                   20                    40
Human TSHR    MRPADLLQLVLLLDLPRDLGGMGCSSPPCECHQEEDFRVTCKDIQRIPSLPPSTQTLKLI
Dog TSHR         PP           HAA   S   K P       D           H  T         F 60                  80                   100
Human TSHR    ETHLRTIPSHAFSNLPNISRIYVSIDLTLQQLESHSFYNLSKVTHIEIRNTRNLTYIDPD
Dog TSHR         Q K     R              L A  R           M           S  S 120                 140                  160
Human TSHR    ALKELPLLKFLGIFNTGLKMFPDLTKVYSTDIFFILEITDNPYMTSIPVNAFQGLCNETL
Dog TSHR                           GV  V   V                    A  A 180                 200                  220
Human TSHR    TLKLYNNGFTSVQGYAFNGTKLDAVYLNKNKYLTVIDKDAFGGVYSGPSLLDVSQTSVTA
Dog TSHR              I  H                    SA              T   Y 240                 260                  280
Human TSHR    LPSKGLEHLKELIARNTWTLKKLPLSLSFLHLTRADLSYPSHCCAFKNQKKIRGILESLM
Dog TSHR 300                 320                  340
Human TSHR    CNESSMQSLRQRKSVNALNSPLHQEYEENLGDSIVGYKEKSKFQDTHNNAHYYVFFEEQE
Dog TSHR         IR               T  G FD       Y      HA   DN Q      DS S
```

FIG. 8b

```
                      360                                       380                            400
Human TSHR   DEIIGFGQELKNPQEETLQAFDSHYDTICGDSEDMVCTPKSDEFNPCEDIMGYKFLRIV
Dog   TSHR                L                              V GN 420              I                440      II              460
Human TSHR   VWFVSLLALLGNVFVLLILLTSHYKLNVPRFLMCNLAFADFCMGMYLLLIASVDLYTHSE
Dog   TSHR                                   T 480      III              500                             520
Human TSHR   YYNHAIDWQTGPGCNTAGFFTVFASELSVYTLTVITLERWYAITFAMRLDRKIRLRHACA
Dog   TSHR                                                                  Y 540      IV              560                    V         580
Human TSHR   IMVGGWVCCFLLALLPLVGISSYAKVSICLPMDTETPLALAYIVFVLTLNIVAFVIVCCC
Dog   TSHR                                              IL L      I        S 600                                VI 620                 640
Human TSHR   YVKIYITVRNPQYNPGDKDTKIAKRMAVLIFTDFICMAPISFYALSAILNKPLITVSNSK
Dog   TSHR                                   M                 LM          T 660      VII              680                             700
Human TSHR   ILLVLFYPLNSCANPFLYAIFTKAFQRDVFILLSKFGICKRQAQAYRGQRVPPKNSTDIQ
Dog   TSHR                                                            S    AG 720                            740
Human TSHR   VQKVTHDMRQGLHNMEDVYELIENSHLTPKKQGQISEEYMQTVL
Dog   TSHR   I          R       S P Q E L       N    K N
```

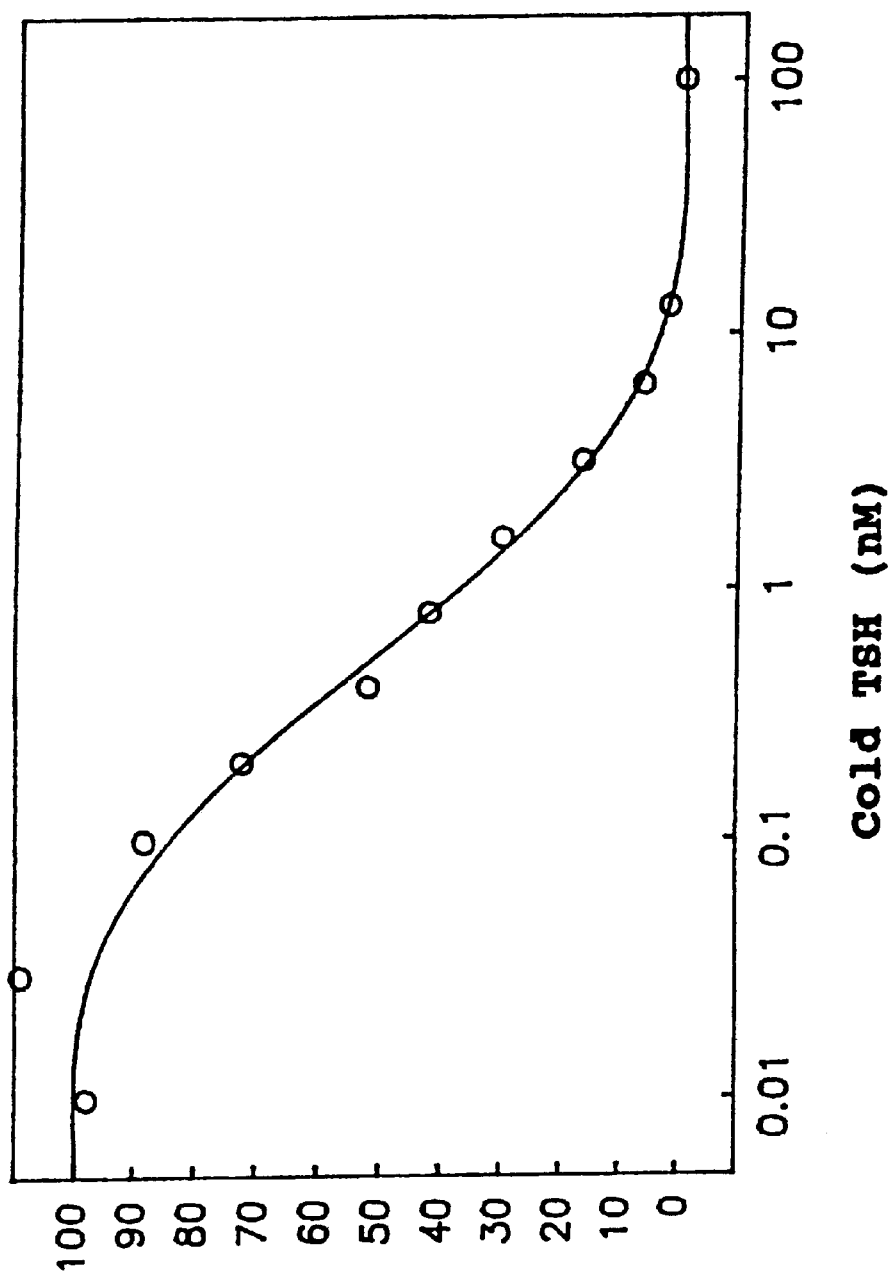

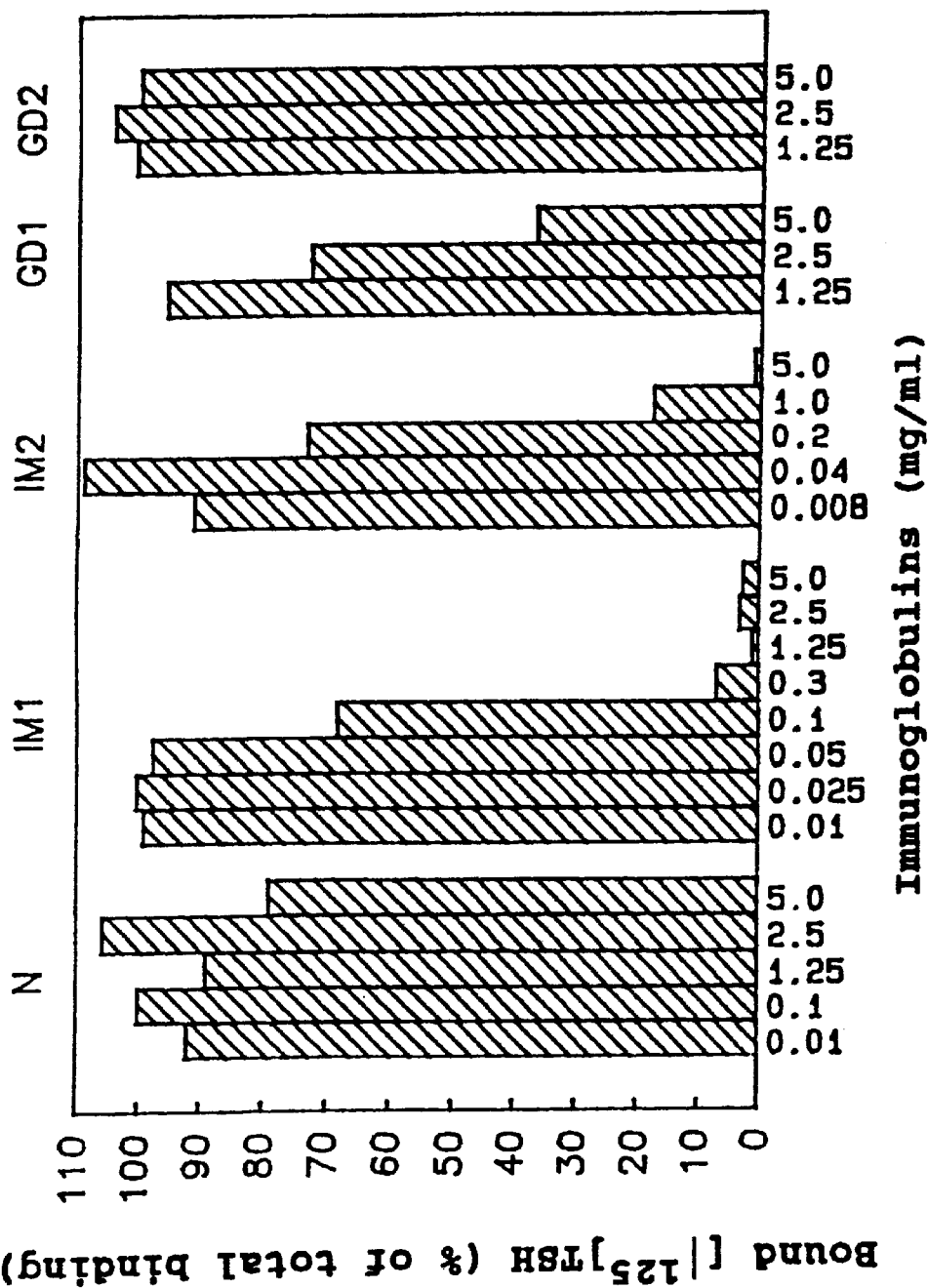

FIG. 11a

```
      -20
       MRPADLLQLVLLLDLPRDLGGMGCSSPPCECHQEEDFRVTCKDIQRIPSLPPSTQTLKLI  40
                   PP   H A   A    S    K  P           D    H  T               F

ETHLRTIPSHAFSNLPNISRIYVSIDLTLQQLESHSFYNLSKVTHIEIRNTRNLTYIDPD  100
           Q K R                L A   A              M              S S

ALKELPLLKFLGIFNTGLKMFPDLTKVYSTDIFFILEITDNPYMTSIPVNAFQGLCNETL  160
                             GV     V                              A   A

TLKLYNNGFTSVQGYAFNGTKLDAVYLNKNKYLTVIDKDAFGGVYSGPSLLDVSQTSVTA  220
                         I  H                         SA            T      Y

LPSKGLEHLKELIARNTWTLKKLPLSLSFLHLTRADLSYPSHCCAFKNQKKIRGILESLM  280

CNESSMQSLRQRKSVNALNSPLHQEYEENLGDSIVGYKEKSKFQDTHNNAHYYVFFEEQE  340
             IR              T  G FD     Y    HA      DN  Q    DS S

DEIIGFGQELKNPQEETLQAFDSHYDYTICGDSEDMVCTPKSDEFNPCEDIMGYKFLRIV  400
          L                                V  GN
```

FIG. IIb

```
                      I                            420                  440  II            460
             VWFVSLLALLIGNVFVLLILTSHYKLNVPRFLMCNLAFADFCMGMYLLLIASVDLYTHSE
                                   T                I I                  IH K Q

480  III         500                  520
             YYNHAIDWQTGPGCNTAGFFTVFASELSVYTLTVITLERWYAITFAMRLDRKIRLRHACA YS
                      H Y          A DA                    HT H Q C VQ          A

IV           540                  560              580
             IMVGGWVCCFLLALLPLVGISSYAKVSICLPMDTETPLALAYIVFVLTNIVAFVIVCCC
             V        M IFA AA  F IF     M                IDS  SLQ  VILL L      I S
                                                                    MS  V  VL 600                  620  VI          640
             YVKIYITVRNPQYNPGDKDTKIAKRMAVLIFTDFICMAPISFYALSAILNKPLITVSNSK
                                                             M                LM        T

VII          660                  680              700
             ILLVLFYPLNSCANPFLYAIFTKAFQRDVFILLSKFGICKRQAQAYRGQRVPPKNSTDIQ
                              S          P   Q E  L                              S   AG 720                  740
             VQKVTHDMRQGLHNMEDVYELIENSHLTPKKQGQISEEYMQTVL
             I       R            S      L         N K  N
```

FIG. 12a

```
       10         20         30         40         50         60         70
5' AGGCAGCAGTTCCTCCTGGGACCTGATGGCTCCCAGATCACTATCTTGGGCCCAGACTTTCTGGAGCTG
       80         90        100        110        120        130        140
   AATCTCCAGTTGCCTCGGAGCCTCCTCAGACTCAGTGTGGCCAGAATGGTGGTCCTGGCTTCCCTCGGG
      150        160        170        180        190        200        210
   CCTGCCCTTCTGCCTCCTTCTGCACCCTGAGATGGTCATCAGCTTTTCTCCCACTGCTGCCCTGTATGCA
      220        230        240        250        260        270        280
   GGGAAGGCCTGCCTGTGGCTGTATCTGTAGTACTTCTTGAATGTGTTTCCTTCTCCCCAGGCCAGAGCT
      290        300        310        320        330        340        350
   GAGAATGAGGCGATTTCGGAGGATGGAGAAAATAGCCCCAGGGACCTGGGCGGAAATGAGGCCGGACTTG
      360        370        380        390        400        410        420
   CTGCAGCTGGTGCTGCTCGACCTGCTCGTTGTTCGTCTCCACCCTGCG
      430        440        450        460        470        480        490
   AGTGCCATCAGGAGGAGGACTTCAGAGTCACCTGCAAGTCACCTGCAAGGATATTCAACGCATCCCCAGCTTACGCCCAG
      500        510        520        530        540        550        560
   TACGCAGACTCTGAAGCTTATTGAGACTCACCTGAGAACTATTCCAAGTCATGCATTTTCTAATCTGCCC
      570        580        590        600        610        620        630
   AATATTTCCAGAATCTACGTATCTATAGATCTGACTCTGCAGCAGCTGGAATCACACTCCTTCTACAATT
```

FIG. 12b

```
        640         650         660         670         680         690         700
TGAGTAAAGTGACTCACATAGAAATTCGGAATACCAGGAACTTAACTTACATAGACCCTGATGCCCTCAA
        710         720         730         740         750         760         770
AGAGCTCCCCTCCTAAAGTTCCTGGCATTTTCAACACTGGACTTAAAATGTTCCCTGACCTGACCAAA
        780         790         800         810         820         830         840
GTTTATTCCACTGATATATTCTTTATACTTGAAATTACAGACAACCCTTACATGACGTCAATCCCTGTGA
        850         860         870         880         890         900         910
ATGCTTTTCAGGGACTATGCAATGAAACCTGAAGCTGTACAACAATGGCTTTACTTCAGTCCA
        920         930         940         950         960         970         980
AGGATATGCTTTCAATGGGACAAAGCTGGATGGAGTATACAGAATAAAATACCTGACAGTTATT
        990         1000        1010        1020        1030        1040        1050
GACAAAGATGCATTTGGAGGAGTATACAGTGGACCAAGCTTGCTGTCTCAAACCAGTGTCACTG
        1060        1070        1080        1090        1100        1110        1120
CCCTTCCATCCAAAGGCCTGGAGCACCTGAAGGAACTGATAGCAAGAAACACCTGGACTCTTAAGAAACT
        1130        1140        1150        1160        1170        1180        1190
TCCACTTTCCTTGAGTTTTCCTTCACCTCACACGGGCTGACCTTTCTTACCCAAGCCACTGCTGTGCTTTT
```

FIG. 12c

```
       1200      1210      1220      1230      1240      1250      1260
AAGAATCAGAAGAAAATCAGAGGAATCCTTGAGTCCTTGATGTGTAATGAGAGCAGTATGCAGAGCTTGC
       1270      1280      1290      1300      1310      1320      1330
GCCAGAGAAAATCTGTGAATGCCTTTGAATAGCCCCCTCCACCAGGAATATGAAGAGAATCTGGGTGACAG
       1340      1350      1360      1370      1380      1390      1400
CATTGTTGGGTACAAGGAAAAAGTCCAAGGATACTCATAACAACGCTCATTATTACGTCTCTTT
       1410      1420      1430      1440      1450      1460      1470
GAAGAACAAGAGGATGAGATCATTGGTTTTTGGCCAGGAGCTCAAAAACCCCAGGAAGAGACTCTACAAG
       1480      1490      1500      1510      1520      1530      1540
CTTTTGACAGCCATTATGACTACACCATATGTGGGGACAGTGAAGACATGGTGTACCCCCAAGTCCGA
       1550      1560      1570      1580      1590      1600      1610
TGAGTTCAACCCGTGTGAAGACATAATGGGCTACAAGTTCCTGAGAATTGTGGTGTTCGTTAGTCTG
       1620      1630      1640      1650      1660      1670      1680
CTGGCTCCTCTGGGCAATGTCTTTGTCCTGCTTATTCTTCCTCACCAGCCACTACAAACTGAACGTCCCCC
       1690      1700      1710      1720      1730      1740      1750
GCTTTCTCATGTGCAACCTGGCCTTTGCGGATTTCTGCATGGGGATGTACCTGCTCCTCATGCCCTCTGT
```

FIG. 12d

```
           1760      1770      1780      1790      1800      1810      1820
AGACCTCTACACTCACTCTGAGTACTACAACCATGCCATCGACTGGCAGACAGGCCCTGGGTGCAACACG
           1830      1840      1850      1860      1870      1880      1890
GCTGGTTTCTTCACTGTCTTTGCAAGCGAGTTATCGGTGTATACGCTGACGGTCATCACCCTGGAGCGCT
           1900      1910      1920      1930      1940      1950      1960
GGTATGCCATCACCTTCGCCATGCGCCTGGACCGGAAGATCCGCCTCAGGCACGCATGTGCCATCATGGT
           1970      1980      1990      2000      2010      2020      2030
TGGGGCTGGGTTTGCTGCTTCCTTCTCGCCCCTGCTTCCTTTGGTGGGAATAAGTAGCTATGCCAAAGTC
           2040      2050      2060      2070      2080      2090      2100
AGTATCTGCCCTGCCCATGGACACCGAGACCCCTCTTGCTCTGGCATATATTGTTTTTGTTCTGACGCTCA
           2110      2120      2130      2140      2150      2160      2170
ACATAGTTGCCTTCGTCATCGTCTGCTGTTATGTGAAGATCTACATCACAGTCCGAAATCCGCAGTA
           2180      2190      2200      2210      2220      2230      2240
CAACCCAGGGGACAAAGATACCAAAATTGCCAAGAGGATGGCTGTGTTGATCTTCACCGACTTCATATGC
           2250      2260      2270      2280      2290      2300      2310
ATGGCCCCAATCTCATTCTATGCTCTGTCAGCAATTCTGAACAAGCCCTCTCATCACTGTTAGCAACTCCA
           2320      2330      2340      2350      2360      2370      2380
AAATCTTGCTGGTACTCTTCTATCCCACTTAACTCCTGTGCCAATCCATTCCTCTATGCTATTTTCACCAA
```

FIG. 12e

```
      2390      2400      2410      2420      2430      2440      2450
GGCCTTCCAGAGGGATGTGTTCATCCTACTCAGCAAGTTTGGCATCTGTAAACGCCAGGCTCAGGCATAC
      2460      2470      2480      2490      2500      2510      2520
CGGGGGCAGAGGGTTCCTCCAAAGAACACACTGATATTCAGGTTCAAAAGGTTACCCACGACATGAGGC
      2530      2540      2550      2560      2570      2580      2590
AGGGTCTCCACAACATGGAAGATGTCTATGAACTGATTGAAAACTCCATCTAACCCCAAAGAAGCAAGG
      2600      2610      2620      2630      2640      2650      2660
CCAAATCTCAGAAGAGTATATGCAAACGGTTTTGTAAGTTAACACTACTCACAATGCTAGGGGAA
      2670      2680      2690      2700      2710      2720      2730
CTTACAAAATAATAGTTTCTTGAATATGCATTCCAATCCCATGACACCCCAACACATAGCTGCCCTCAC
      2740      2750      2760      2770      2780      2790      2800
TCTTGTGCAGGCGATGTGTTTCAATGTTTCATGGGGCAAGAGTTTATCTCTGGAGAGTGATTAGTATTAACC
      2810      2820      2830      2840      2850      2860      2870
TAATCATTGCCCCAAGAAGGAAGTTAGGCTACCAGTCCAAGTCCAGGTGAAATGCCAGGTGAAATCAAAATAATCT
      2880      2890      2900      2910      2920      2930      2940
ACACTATCTAGAAGACTTTCTTGATGCCAAGTCCAGAGATGTCATTGTGTAGGATGTTCAGTAAATATTA
      2950      2960      2970      2980      2990      3000      3010
ACTGAGCTATGTCAATATAGAGCTTTCTCAGTTTTGTATAACATTTCATACTAAAGATTCAGCAAATGGAA
      3020      3030      3040      3050      3060      3070      3080
AATGCTATTAATTTGGTTGGGTGACCAACAAGATAAAATCAGTCCCACGTTGGCTTCAACTAGATGTT
```

FIG. 12f

```
      3090      3100      3110      3120      3130      3140      3150
CCCTGATACAAAGAGAACTTGATTTCCTTAAAACTGAAAAGCCAAAACAGCTAGCTGTCATACAAGAAA
      3160      3170      3180      3190      3200      3210      3220
CAGCTATTATGAGACATGAAGGAGGGTAAGAATTAGCTTTAAGTTTTGTTTTTGCTTTTGTTTTGTTTTA
      3230      3240      3250      3260      3270      3280      3290
ACTCAACCTATTAATCATCTCTTCACAAGAATCCACCTGATGTGACCAAGCTATTATGTTGCCTGGAA
      3300      3310      3320      3330      3340      3350      3360
AAACTGGCAAGATTTCAGCTTATGTGTGCCTAGCAAACTAAGAATTGCTCTTCTTGGCCAGCCTCATAGCA
      3370      3380      3390      3400      3410      3420      3430
TAAAGATGTGAACTCTAGGAAGTCTTTCTGAGTAGCAATAAGTGGGAATTATGGGCAGAGCACACTCAA
      3440      3450      3460      3470      3480      3490      3500
TCCCCTGTTGATTAATAAAACAGGCTGGACACTAATTAACTATGGGACTTAAATCTGTAGAAATGAAGGA
      3510      3520      3530      3540      3550      3560      3570
GTCCAATAGCTTCTTCCAATTTTAAAAACTCAGTACATCCCTTTCCCTCAAATATATATTTCTAAGATAA
      3580      3590      3600      3610      3620      3630      3640
AGAGAAAGAGAGCACTAAGTAAGTAGAATCTGTTTTTCCTATTTTGTAGGGCTGCTGACTCCTAGTCCT
      3650      3660      3670      3680      3690      3700      3710
TGAAGCCTAGACACATGACCCAGGAAATTTTCCTTTGTTTCACTTTTGATTATGATGTCTGAGCCAAAAA 3'
```

POLYPEPTIDES HAVING THYROTROPIN-RECEPTOR ACTIVITY, NUCLEIC ACID SEQUENCES CODING FOR SUCH RECEPTORS AND POLYPEPTIDES, AND APPLICATIONS OF THESE POLYPEPTIDES

The invention relates to polypeptides having thyrotropin-receptor activity, to nucleic acids coding for such polypeptides, to antibodies to these polypeptides and to the use of the polypeptides and antibodies in assay methods.

The literature references indicated by numbers in parentheses in this specification are listed in the form of a bibliography at the end of the description.

Pituitary glycoproteins (Luteinizing hormone, LH; follicle stimulating hormone, FHS; and thyroid stimulating hormone or thyrotropin, TSH) form a family of closely related hormones.

The pituitary hormone thyrotropin (TSH) is the main physiological agent regulating the thyroid gland. It stimulates the function and the proliferation of thyrocytes and induces the expression of differentiation (1). Most of its effects are mediated by cyclic AMP (cAMP) (1). As the other pituitary and placental glycoprotein hormones (FSH, LH, CG), TSH is a heterodimer. All these hormones share an identical alpha subunit; the beta subunit, despite sequence similarity, is specific for each (2). The activated TSH, FSH and LH-CG receptors stimulate adenylyl cyclase in their target cells via mechanisms mediated by the G protein Gs (3). In man, the TSH receptor may be the target of autoimmune reactions leading to hyper- or hypo-stimulation of the thyroid gland by autoantibodies in Grave's disease and in idiopathic myxoedema, respectively (4).

A prerequisite to studies of such diseases and to the elucidation of receptor structure and function is the availability of receptor preparations, particularly human, at a reasonable cost and in relative abundance.

To date, particulate membrane preparations and detergent-solubilised thyroid membranes, often of porcine or bovine origin (4) have been used in such studies. Human receptor preparations are not only costly but are also difficult to reproduce identically. Furthermore, the known preparations cannot be considered to be "purified" receptors; they are enriched with respect to their receptor content but do not allow purification of the receptor to a degree which would enable a partial sequence analysis, and hence its cloning. These receptor preparations have never allowed characterisation of the entity responsible for the TSH-binding activity.

Cloning and expression of the related LH-CG receptor has recently been achieved. A cDNA for the rat LH-CG receptor was isolated with use of a DNA probe generated in a polymerase chain reaction with oligonucleotide primers based on peptide sequences of purified receptor protein (15). Variants of the porcine LH-CG receptor were cloned by screening a λgt11 library with cDNA probes isolated with monoclonal antibodies (16).

Attempts have been made to clone the TSH receptor (6) using a method which exploits the sequence similarity displayed by all known G-protein coupled receptors. A pair of oligonucleotide primers corresponding to transmembrane segments III and VI were used on cDNA from thyroid tissue under conditions allowing amplification of the primed sequences by the polymerase chain reaction. The method did not allow cloning of the TSH receptor but led instead to the cloning of four new members of the G-protein coupled receptor family.

The difficulties encountered in purifying and in cloning the TSH receptor are thought to be due to its extra-ordinary low abundance even in thyroid cells.

The present inventors have succeeded in cloning the TSH receptor and variants thereof, firstly by applying the technique described in (6) but with different sets of primers, and with human genomic DNA as the template, rather than cDNA and secondly by use of a selected sequence amplified by this technique as a probe.

BRIEF DESCRIPTION OF THE DRAWINGS

Certain aspects of the invention are illustrated in the FIGS. 1 to 12. Figures illustrating amino-acid sequences use the one-letter abbreviation system.

FIG. 1 is a sequence comparison of clone HGMP09 with a panel of G-protein coupled receptors (6 and ref. therein). Only the sequence around transmembrane segment III of each receptor is shown in the one letter code. Residues conserved in HGMP09 and in more than 50% of the other receptors are indicated by an asterisk. The "DRY" and "Asp113" residues (9) are indicated by ^. Sequences HGMP09 through RDC1 are listed s SEQ ID NO:35 through SEQ ID NO:53 in the attached SEQUENCE LISTING.

FIGS. 2a–2d show the primary structure of the dog TSH receptor (SEQ ID NO:75), as deduced from the nucleic acid sequence of dTSHr. The sequence was aligned (17) with full-length rat and pig LH-CG sequences (SEQ ID NO:55 and SEQ ID NO:56, respectively) (15, 16) and with HGMP09 partial sequence. Numbering is given from the first residue predicted in the mature polypeptide by von Heihne algorithm (11). Identical residues and conservative replacements in TSHr and LH-CGr are indicated by * and ., respectively. Sites for N glycosylation are underlined. Putative transmembrane segments are overlined. Lambda phages containing dTSHr inserts were subcloned in M13 and sequenced on both strands (Applied Biosystems model 370A) using a combination of forced cloning and exonuclease III deletions (21).

FIG. 2e is a dendogram constructed from the sequences of G-protein coupled receptors. The CLUSTAL algorithm (17) was used to construct a dendogram from the sequences of 22 receptors (6) and references therein) including rat and pig LH-CG receptors (16, 17), HGMP09 and the TSH receptor. For each receptor, a segment corresponding to the known sequence of HGMP09 (131 residues, extending from transmembrane segments II to V) was used for comparison by the program.

FIGS. 5a–5c show the cDNA sequence coding for the dog TSH receptor (SEQ ID NO:57), which was expressed in oocytes and culture cells.

FIG. 7 shows the sequence alignment of the repeats constituting the extracellular domain of the thyrotropin receptor amino-acid sequence (SEQ ID NO:58). The signal peptide, as determined by Von Heijne algorithm is represented in italic. The repeat missing in the molecular variant of the receptor is indicated by the leftward arrow.

FIGS. 8a and 8b show the primary structure of the human TSH receptor as deduced from its cDNA sequence (SEQ ID NO:59). The amino-acid sequence corresponds to the 2292 nucleotide open reading frame determined from the sequencing of two overlapping inserts in lamda gt11 clones (see examples). It is aligned for comparison with the dog TSH receptor sequence (only non conserved amino-acids are indicated). Numbering starts from the first residue of the mature polypeptide as determined by von Heijne algorithm [11]. Potential N-glycosylation sites are underlined and putative transmembrane segments are overlined.

FIG. 9 shows the displacement by nonradioactive TSH of [$^{125}$I]TSH from human TSH receptors expressed in cos-7 cells. Results are expressed as percentage of the [$^{125}$I]-labelled TSH bound by transfected cells in the absence of competitor (1400 cpm) after correcting for nonspecific binding (radioactivity bound in the presence of 100 nM unlabelled TSH, 240 cpm).

FIG. 10 represents the displacement by immunoglobulins of [$^{125}$I]TSH from human TSH receptor expressed in cos-7 cells. Results are expressed as described in the legend to FIG. 9. Immoglobulins were prepared (see examples) from a normal individual (N), from patients with idiopathic myxoedema (IM1, IM2) or Graves' disease (GD1, GD2). The concentration of immunoglobulins in the assay is indicated. The ability of IM1 and IM2 (1.5 mg/ml) to inhibit TSH-stimulated cAMP production in a human thyrocyte assay was 100% and 85%, respectively. The thyroid stimulating activity of GD1 and GD2 (1.5 mg/ml) was equivalent to that of 10 mU/ml of TSH, respectively.

FIGS. 11a and 11b show the primary structure of a TSH receptor according to the invention, in which a plurality of letters at any one site indicates the presence of one of the given amino acid residues at that site, SEQ ID NO:29 lists the complete sequence. SEQ ID NO:81 and SEQ ID NO:82 list the first and second full sequences, respectively with all possible substitutions included. SEQ ID NO:81 lists the complete sequence shown and SEQ ID NO:82 lists the sequence with substitution shown in the figure.

FIGS. 12a–12f illustrate the cDNA sequence of the cloned human TSH receptor (SEQ ID NO:62).

Figure 3A:
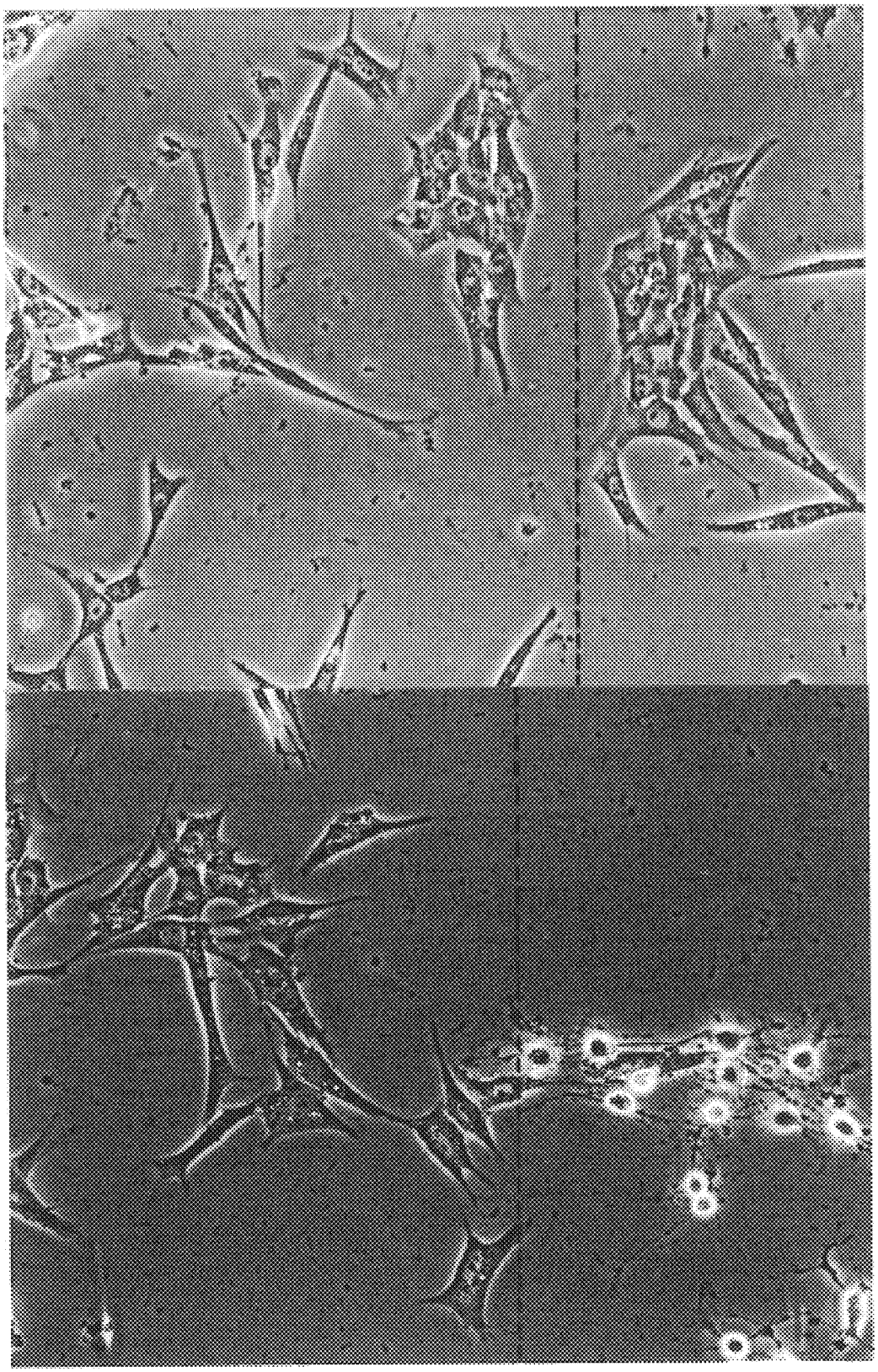
FIG. 3a shows TSH induced morphological changes in Y1 cells microinjected with TSH receptor mRNA. Y1 cells were microinjected with recombinant TSH receptor mRNA (0.1 pl at 0.25 ug/ul) (right) or water (left) as described (13) and incubated in control medium (upper panel) or with TSH (0.1 nM) (lower panel). RO 201724 and insobutylmethylxanthine ($10^{-6}$ M each) were present in all incubations.

The invention relates to polypeptides possessing thyrotropin receptor activity, characterised in that they comprise the amino-acid sequence shown in FIG. 11, or a fragment thereof, or an amino-acid sequence derived from this sequence by substitution or deletion of any of the amino-acid residues indicated in FIG. 11, or by insertion of additional amino-acid residues. Such derived sequences may show, for example, about 80% homology with the sequence of FIG. 11. The polypeptides of the invention are in substantially pure form, and are preferably in a non-thyroid environment. By 'substantially pure form' is meant 'free of impurities' associated with detergent-solubilised thyroid membrane preparations.

By "TSH-receptor activity" is meant either TSH-binding properties or anti-TSH receptor antibody-binding properties or ability to activate adenylyl cyclase or phospholipase C via G proteins when exposed to TSH or anti-TSHr antibodies. These properties are easily verified by contacting the polypeptide with for example labelled TSH or labelled anti-TSHr antibodies or by monitoring the adenylyl cyclase activity of a membrane preparation containing the polypeptide. The polypeptides of the invention include the entire TSH receptor as identified by the inventors, and fragments or variants of this polypeptide as defined below. The entire TSH receptor is composed of a signal peptide (20 residues) followed by a large putative extracellular domain (398 residues) containing 5 sites for N-glycosylation, connected to a 346 residue COOH domain containing seven putative transmembrane segments. The amino-acid sequence of the receptor is illustrated in FIG. 11.

More particularly, the invention relates to a polypeptide characterised in that it comprises an amino-acid sequence represented by the following general formula:

$$[x]_n-[y]_m-[z]_p$$

wherein n=0 or 1; m=0 or 1; p=0 or 1;
with the proviso that n+m+p>0
and x, y and z are defined as follows (using the one-letter amino-acid symbol and wherein
a plurality of letters at any one site indicates the presence of one of the given amino-acid residues at that site (Sequences are listed in full with replacement residues in the SEQUENCE LISTING; i.e., x=SEQ ID NO:1 or alternately SEQ ID NO:2 with alternate residues shown below sequence.),

```
x = MRPADLLQLVLLLDLPRDL,
     PP  H  A    S
``` y=at least the minimum number of consecutive amino-acids of the following sequence (SEQ ID NO:3 or alternately SEQ ID NO:4 which contains alternate residues shown below sequence.) necessary for the presentation of immunogenic properties:

```
GGMGCSSPPCECHQEEDFRVTCKDIQRIPSLPPSTQTLKLI
   K  P         D        H  T        F

ETHLRTIPSHAFSNLPNISRIYVSIDLTLQQLESHSFYNLSKVTHIEIRNTRNLTYIDPD
  Q K   R       L    A   R         M        S S

ALKELPLLKFLGIFNTGLKMFPDLTKVYSTDIFFILEITDNPYMTSIPVNAFQGLCNETL
             GV  V              V               A A

TLKLYNNGFTSVQGYAFNGTKLDAVYLNKNKYLTVIDKDAFGGVYSGPSLLDVSQTSVTA
        I H                  SA            T        Y

LPSKGLEHLKELIARNTWTLKKLPLSLSFLHLTRADLSYPSHCCAFKNQKKIRGILESLM

CNESSMQSLRQRKSVNALNSPLHQEYEENLGDSIVGYKEKSKFQDTHNNAHYYVFFEEQE
  IR        T  G FD    Y      HA  DN Q   DS S

DEIIGFGQELKNPQEETLQAFDSHYDYTICGDSEDMVCTPKSDEFNPCED
   L                 V  GN
``` and $z=[I-II-II_i-III-III_i-IV-V-VI-VII-VII_i]$ wherein the amino-acid sequences I-II-II$_i$-III-III$_i$-IV-V-VI-VII-VII$_i$ are independently present or absent and have the following meanings:

```
I = IMGYKFLRIVVWFVSLLALLGNVFVLLILLTSHYK
                                    IV
```

(SEQ ID NO:5 or SEQ ID NO:6) or at least 12 consecutive amino-acid residues of this sequence;

```
II = LNVPRFLMCNLAFADFCMGMYLLLIASVDLYTHSEYYNHA
     T              I I            IH K Q H Y
```

(SEQ ID NO:7 or SEQ ID NO:8, respectively) or at least 12 consecutive amino-acid residues of this sequence;

```
II¹ =
IDWQTGPGC
       A
```

(SEQ ID NO:9 or SEQ ID NO:10, respectively) or at least 2 consecutive amino-acid residues of this sequence;

```
III = NTAGFFTVFASELSVYTLTVITL
         DA
```

(SEQ ID NO:11 or SEQ ID NO:12, respectively) or at least 22 consecutive amino-acid residues of this sequence;

```
III_i =
ERWYAITFAMRLD
  HT  H  Q
```

(SEQ ID NO:13 or SEQ ID NO:14, respectively) or at least 2 consecutive amino-acid residues of this sequence;

```
IV = RKIRLRHACAIMVGGWVCCFLLALLPLVGISSYAKVSICL
        C  VQ    YSV  M IFA AA  F IF       M
```

(SEQ ID NO:15, SEQ ID NO:16 or SEQ ID NO:17, respectively) or at least 12 consecutive amino-acid residues of this sequence;

```
V = PMDTETPLALAYIVFVLTLNIVAFVIVCCCYVKIYITVRN
       IDS   SQL VIL  L  VL  I      S
                 MSL V
```

(SEQ ID NO:18, SEQ ID NO:19, or SEQ ID NO:20, respectively) or at least 12 consecutive amino-acid residues of this sequence;

```
VI = PQYNPGDKDTKIAKRMAVLIFTDFICMAPISFYALSAILNKPLIT
                             M              LM
```

(SEQ ID NO:21 or SEQ ID NO:22, respectively) or at least 12 consecutive amino-acid residues of this sequence;

```
VII = VSNSKILLVLFYPLNSCANPFLYAIFTKAFQRD
                                    T
```

(SEQ ID NO:23 or SEQ ID NO:24, respectively) or at least 12 consecutive amino-acid residues of this sequence;

```
VII_i =
VFILLSKFGICKRQAQAYRGQRVPPKNSTDIQVQKVTHDMRQGLHNMEDVYELIENS
       S        AG  I     R        SP  Q  E       L

HLTPKKQGQISEEYMQTVL
     N   K  N
```

(SEQ ID NO:25 or SEQ ID NO:26, respectively) or at least 12 consecutive amino-acid residues of this sequence;

it being understood that any of the above-specified amino-acids can be replaced or deleted, and that extra amino-acid residues may be inserted provided the thyrotropin receptor activity is maintained.

The sequence represented by $[x]_n$ in the above general formula corresponds to the signal sequence of the TSH receptor. This part of the polypeptide naturally ensures the transport to the cell membrane of the adjoining [y] and/or [z] fragments, after its production in the cell. Clearly the signal sequence does not need to be present in the polypeptide in cases where transport to the membrane is not required (for example in in vitro translation of the mRNA encoding the polypeptide), or may be replaced by other signal sequences to facilitate production of the recombinant receptor in certain host cells.

The sequence represented by $[z]_p$ in the above general formula corresponds to the COOH domain of the entire polypeptide containing the seven putative transmembrane fragments I–VII, which show homology with the corresponding region of other G-protein coupled receptors. The polypeptides of the invention include, as indicated above, variants of the basic TSH receptor sequence lacking part or all of the transmembrane domain. It is thought that these types of variants may exist naturally as a result of an alternative splicing phenomenom. By homology with other, known G-protein coupled receptors, the seven putative transmembrane segments have tentatively been identified as shown in FIG. 11 (numbered I to VII). The variant polypeptides of the invention include polypeptides missing some or all of the fragments I–VII$_i$ as defined above, which definition includes the putative extracellular and intracellular "loops" occuring between the transmembrane segments (see FIG. 6). The transmembrane segment(s) missing may therefore, for example, be a segment selected from segments I to VII as indicated in FIG. 11 or may be part of one of those segments, or may be a transmembrane segment in conjunction with its adjoining intracellular and/or extracellular loop.

It is also within the terms of the invention to replace some or all of the transmembrane domain by the transmembrane domain, or part of this domain, of a different receptor, thus giving rise to a hybrid receptor. This type of receptor is particularly interesting in cases where the extracellular part of the TSH receptor needs to be anchored in a cell membrane having characteristics which are different from, or even incompatible with, the transmembrane portion of the TSH receptor. It is also possible to use as the transmembrane domain in a hybrid receptor any amino-acid sequence exhibiting suitable anchoring properties. Such a sequence could be entirely synthetic or based on any transmembrane protein.

It is to be noted that the invention also embraces polypeptides having thyrotropin receptor activity which lack the entire transmembrane domain. In this case, the polypeptide corresponds to the extracellular domain of the naturally occuring receptor. This extracellular part of the receptor which is apparently responsible for ligand binding, is identified by the region [y] in the general formula. A polypeptide lacking the entire transmembrane domain is respresented by the general formula $[y]_m$, where m=1, the [z] part of the sequence being absent. This extracellular part of the receptor [y], is characterised by an imperfect repeat structure which can be aligned as shown in FIG. 7. The polypeptides of the invention include variants in which one or more of these repeats is missing. It is however important that sufficient aminoacids be present to allow formation of antibodies (monoclonal or polyclonal). Such immunogenic amino-acid sequences may comprise for example 5, 6, 7, 8 or 9 consecutive amino-acids of the "y" sequence defined above. The immunogenic nature of the fragments of the invention is tested by injection of the fragment in question into a laboratory animal, followed by investigation of the reactivity between any antibodies thus formed and the immunising fragment.

In particular, the invention encompasses polypeptides in which the second repeat (marked by an arrow in FIG. 7) is missing.

The invention also relates to nucleic acid sequences coding for the polypeptides of the invention as well as the corresponding complementary sequences. Examples of such sequences are those shown in FIGS. 5 and 12, and fragments of these sequences, as well as corresponding degenerate sequences. The nucleic acid fragments embraced by the invention normally have at least 8 nucleotides and have preferably at least 12 or preferably at least 16 nucleotides. Such fragments, or their complementary sequences can be used as primers in the amplification of segments of DNA using the polymerase chain reaction, for example in the production of cDNA coding for the polypeptides having thyrotropin receptor activity.

The nucleic acid sequences of the invention coding for the entire TSH receptor are in a genetic environment other than that found naturally in thyroid cells. For example, the genetic environment may be that of a Cos-7 cell, a CH0 cell or Y1 cells.

The polypeptides of the invention can be produced in several different ways. For example, a host cell such as COS 7 cells, CHO cells, NIH3T3 cells, Xenopus oocytes or Y1 cells can be transformed by a vector containing a nucleic acid insert coding for the desired peptide, in conjunction with all the necessary regulatory elements such as promoter, transcription termination signals etc, or can be microinjected with recombinant mRNA transcribed from appropriate vectors containing the receptor encoded sequence. Expression of the insert normally leads to the insertion of the recombinant polypeptide in the membrane of the cell used as host. In this way, the receptor polypeptide can be used in this form, the receptor thus being present in a non-thyroidal eukaryotic cellular environment, or in a solubilised membrane fragment form. The non-thyroid cells expressing the recombinant receptor exhibit a receptor density of up to ten times that observed in thyroid cells.

Furthermore, in the case where only a fragment of the polypeptide is required, the correspondingly shorter nucleic acid sequence can be used to transform a suitable host cell, for example, a DNA coding for the putative extracellular region only, or one or more repeats of the repetitive portion of this region. It is also within the terms of the invention to synthesise the polypeptide chemically, by successive assembly of the required amino-acid residues. In cases where larger fragments are desired, it is possible to synthesise first a series of smaller fragments and to ultimately assemble these fragments to form the larger fragment.

The invention also relates to antibodies, both polyclonal and monoclonal, to the thyrotropin-receptor polypeptides. The antibodies of the invention are preferably in a purified form, and may be of animal origin e.g. rabbit or mouse. As mentioned earlier, in man the TSH-receptor may be the target of auto-immune reactions giving rise to hyper- or hypo-stimulation of the thyroid gland by stimulating or blocking autoantibodies respectively. The antigenic nature of the polypeptides of the invention, particularly the putative extracellular domain, permits the preparation of antibodies, which can be used in a variety of studies and assays. The TSH-receptor binds both TSH and anti-TSHr antibodies, thus it is possible in certain studies to replace TSH by anti-TSHr antibodies. The phenomenon of competition between labelled and unlabelled species is particularly useful in such assays. Use of specific fragments of the TSH receptor allows the preparation of antibodies against defined epitopes, and, by using a panel of such antibodies, allows further characterisation of the type of disorder present in auto-immune patients.

One such assay falling within the terms of the invention is a process for the quantitative detection of thyrotropine (TSH) or of anti-thyrotropine receptor antibodies (anti-TSHr) in a biological sample characterised in that a polypeptide according to the invention is contacted with the biological sample suspected of containing TSH or anti-TSHr antibodies and, either simultaneously or subsequently, contacted with labelled TSH, or with labelled anti-TSHr antibodies and the remaining, bound labelled TSH or bound labelled anti-TSHr antibodies after competition between the labelled and unlabelled species, is measured.

In this type of assay, the competition between the labelled TSH or labelled antibodies with the unlabelled TSH or antibodies present in the biological sample is measured as an indication of the concentration of that species in the sample.

Alternatively, instead of using competition between two like-species to measure TSH, it is also possible to use a receptor polypeptide to bind the TSH in the biological sample, and then after washing to add labelled anti-TSH antibodies which selectively detect the bound TSH. This type of assay can also be carried out using immobilized or solubilised receptor polypeptide to bind the anti-TSHr-antibody in a biological sample, followed by detection of the bound antibody by labelled anti immunoglobulins or protein A or protein G or any other agent capable of recognizing an antibody.

Another means of assaying the TSH or anti-TSHr antibodies in a sample exploits the effect which the binding of these species with the TSH receptor has on the adenylyl cyclase activity of the cell bearing the receptor. Thus, this aspect of the inventions relates to a process for the quantitative detection of TSH or of anti-TSHr antibodies characterised by contacting intact cells operationally transformed by a nucleotide sequence, encoding a polypeptide of the invention or membrane preparations of such cells with the biological sample suspected of containing TSH or anti-TSHr antibodies and measuring in the intact cells or membranes the change in adenylyl cyclase activity, for example by measuring C-AMP generation or release.

The binding of TSH itself or of stimulating anti-TSHr antibodies to the receptor polypeptide leads to an increase in adenylyl cyclase activity, whereas the binding of blocking anti-TSHr antibodies leads to an inhibition of TSH-induced adenylyl cyclase stimulation. By comparing the adenyl cyclase activity induced by exposure of the receptor polypeptide to TSH with that induced by antibodies in a sample, it is possible, according to the invention, to distinguish blocking antibodies from stimulating antibodies. In order to quantitatively determine blocking antibodies in a sample, the sample is contacted with the receptor polypeptides either at the same time as with TSH, or before contacting with TSH. In this way the adenylyl cyclase stimulating effect of TSH on the receptor is blocked by the blocking antibodies and is quantified to indicate the concentration of blocking antibodies present in the sample. Such measurements can be carried out in intact cells bearing the TSH receptors of the invention, or in membrane preparations of such cells. Other effector systems which can be used in this type of detection are, for example, activities of phospholiphase C, protein tyrosine kinase, phospholipase A2 etc.

The labels used in the assays of the invention are those conventionally used in the art, for example, radioactive labelling, enzymatic labelling, labelled anti-immunoglobulins, protein A, protein G, depending upon the type of assay.

Another aspect of the invention relates to a process for the quantitative detection of fragments of TSH receptor in a biological fluid. Such fragments may be found circulating in patients suffering from thyroid disorders. This aspect of the invention involves contacting the sample with antibodies according to the invention which have previously been labelled, if necessary, and determining the binding, if any, in the sample by any method involving separation of bound labelled antibody from unbound labelled antibody or by competition between the said fragments and a polypeptide according to the invention. In this latter case it is necessary to label the receptor polypeptide, for example with $^{125}$I.

The antibodies of the invention may also be used in the immunohistochemical detection of TSH receptors, for example in endocrinological investigations or in anatomopathology. In this type of process, the antibodies are again labelled to permit their detection.

The polypeptides of the invention may also be used in the purification of stimulating or blocking antibodies to TSHr and of TSH by contacting the polypeptide with a source of TSH or anti-TSHr antibodies, separating the bound and free fractions and finally dissociating the receptor-bound entity. If necessary, further successive purification steps known per se may be added. Such a purification process is facilitated by the immobilisation of the receptor polypeptide, for example in a column or any other solid support.

The invention also embraces kits suitable for the detection of TSH or anti-TSHr antibodies. Such kits are characterised in that they contain:

a) a polypeptide according to the invention and defined above, said polypeptide having thyrotropin receptor activity and being either in an immobilised or solibilised form;

b) at least one of the following reagents:
   i) labelled TSH
   ii) labelled anti-TSHr antibodies
   iii) reagents necessary for the measurement of adenylyl cyclase activity.

For example, a kit for effecting the detection of autoantibodies directed against the TSH receptor by competition would include the polypeptide of the invention, in immobilised or solubilised form, with labelled TSH or unlabelled TSH in combination with agents permitting the TSH to be labelled. Alternatively, such a kit might include antibodies to the TSH receptor and means of labelling them, instead of the TSH.

The invention will be illustrated by the following examples:

EXAMPLES

I—Cloning of Dog TSHr a) Identification of HGMP09

As most G protein-coupled receptor genes do not contain introns in their coding sequence, a similar strategy to that previously described (6) was used, but using different sets of degenerated primers and with human genomic DNA as starting material. Eleven clones displaying sequence similarity with G-protein coupled receptors where thus obtained (7). Out of these, one clone (HGMP09) which was amplified with primers corresponding to transmembrane segments II and VII, presented sequence characteristics suggesting that it belonged to a distinct subfamily of receptors.

The primers used in this amplification were:

```
5' TAGATCTAGACCTGGCGITTGCCGATCT 3'
            T   T C GC   T   CA
                         G and 5' ACTTAAGCTTGCAGTAGCCCAIAGGATT 3'
                   A   AAAG   G  G
``` a plurality of nucleotides at any one site indicating the presence of one of the given nucleotides at that site. Sequences are listed sequentially as SEQ ID NO:51 through SEQ ID NO:55 with alternative nucleotides inserted.

A dendrogram constructed from the alignment shown in FIG. 1 demonstrated that it is equally distant from all receptors cloned to date (7); in particular, it does not contain the canonical Asp Arg Tyr (DRY) tripeptide close to transmembrane segment III [(8)] and lacks the Asp residue implicated in the binding of charged amines is adrenergic (Asp113), muscarinic, dopaminergic and serotonergic receptors (9).

b) Identification of dog TSHr

In the frame of a systematic screening for the expression of the new receptors in thyroid tissue, HGMP09 was used as a probe both in Northern blotting experiments with thyroid and non-thyroid tissues, and in screening of a dog thyroid cDNA library. HGMP09 did not hybridize to thyroid mRNA but identified a major 2.6 kb transcript in the ovary and the testis. However, under moderate conditions of stringency it hybridized to one out of 50,000 thyroid cDNA clones suggesting cross-hybridization with a relatively abundant putative receptor of the thyroid. From these characteristics, it was hypothesized that HGMP09 encoded a receptor fragment, distinct from the TSH receptor, but with sequence characteristics expected from close relatives like LH or FSH receptors. A full-length cross-hybridizing clone (dTSHr) was isolated and used as a probe in Northern blots of ten different dog tissues. It hybridized to a 4.9 kb transcript present only in the thyroid gland and in cultured thyrocytes. Interestingly, the signal was much stronger in cultured thyrocytes exposed for several days to the cAMP agonist forskolin than in thyroid tissue. This is a characteristic one would expect from the TSH receptor whose expression is known to be up-regulated by cAMP agonists in cultured cells (10). A 4,417 bp cDNA clone was sequenced completely. It contains an open reading frame of 764 aminoacids beginning with a 20 residue signal peptide, as predicted by Von Heijne algorithm (11) (FIG. 2a). Comparison to known G-protein coupled receptors (see hereunder and FIG. 2b) and hydropathy profile analysis (not shown) demonstrated a 346 residue C-terminal structure with seven putative transmembrane domains preceded by 398 aminoacids constituting a large putative extracellular domain.

c) Expression of dog TSHr

Figure 3B:
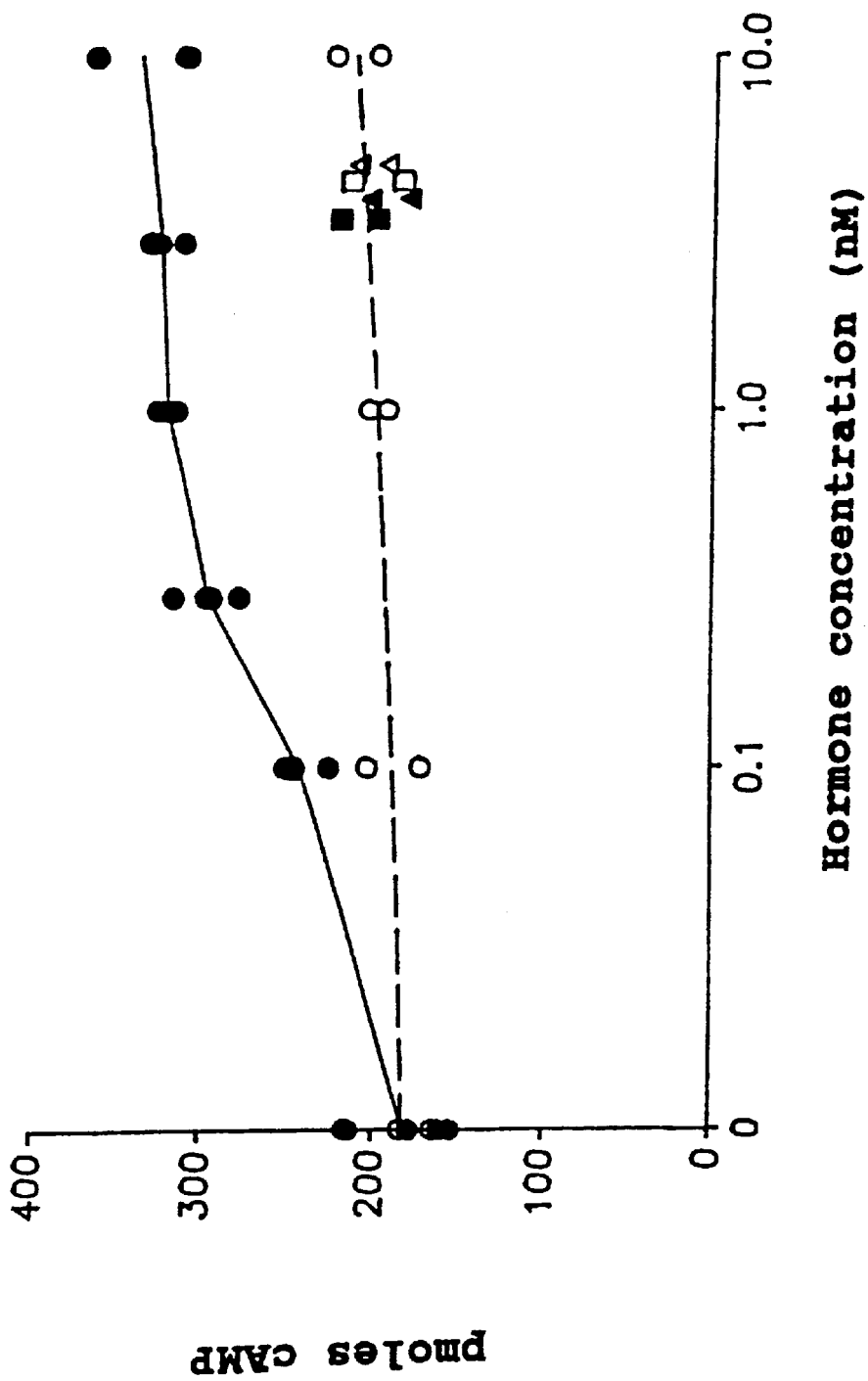
FIG. 3b shows TSH induced cAMP accumulation in Xenopus oocytes microinjected with TSH receptor mRNA. Xenopus oocytes were handled as described (22) and injected with water (open symbols) or recombinant TSH receptor mRNA (13) (50 nl at 0.1 ug/ul) (filled symbols). After 3 days in control medium, batches of 35 oocytes were incubated for 90 min. in medium supplemented with various concentrations of TSH (circles), LH (squares) or FSH (triangles). cAMP was determined as described (14). RO 201724 and isobutylmethylxanthine ($10^{-6}$ M each) were present in all incubations. Incubation of control oocytes in forskolin at $10^{-4}$ M resulted in doubling of the cAMP concentration (not shown).
Figure 4:
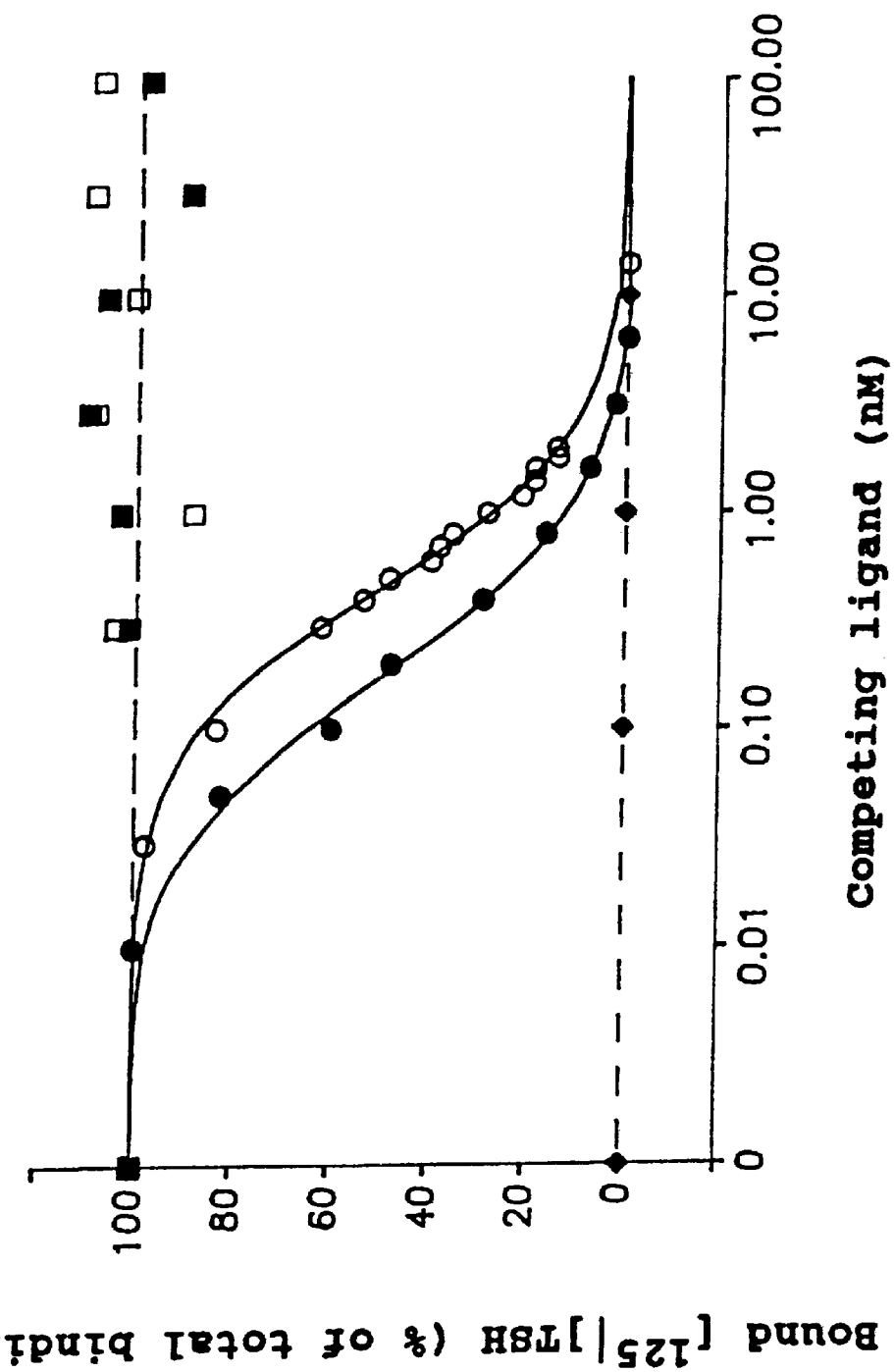
FIG. 4 illustrates the displacement of $^{125}$I TSH receptors expressed in cos7 cells. Cos7 cells were transfected with TSH receptor cDNA subcloned in pSVL (23). After 72 hours, cells were harvested and a membrane fraction was prepared (24). Membranes were similarly prepared from wild type cos7 cells and from dog thyrocytes in primary culture (20). Binding of $^{125}$I TSH (TRAK Henning) was performed at 0° C. for 120 min. in the presence of various concentrations of competitors (TSH-Armour, FSH and LH, UCB bioproducts). Bound radioactivity was separated by centrifugation and counted. Results are expressed as percent $^{125}$I TSH bound by transfected cells in the absence of competitor (3,000 cpm) over non-specific binding (radioactivity bound in the presence of 100 nM cold TSH, 800 cpm). Open and filled circles represent displacement by cold TSH from cos7 and thyrocyte membranes respectively. Open and filled squares represent displacement from cos7 by LH and FSH, respectively. Diamonds represent control cos7 cells in presence of various amounts of cold TSH.

The encoded polypeptide was unambiguously identified as the TSH receptor by expression of the cDNA in a variety of systems. Microinjection of recombinant mRNA in adrenocortical Y1 cells and in Xenopus oocytes conferred a TSH responsive phenotype to both systems. Y1 cells responded to TSH by a characteristic morphological change which is triggered by elevation of cAMP in the cytoplasm (12,13). Xenopus oocytes (FIG. 3) displayed a dose-dependant increase in cAMP which was specific for stimulation by TSH and corresponded to the expected sensivity of the dog receptor to bovine TSH (half-maximal effect around 0.3 nM) (14). Transient expression of the receptor cDNA was obtained in Cos7 cells (FIG. 4). Specific binding of $^{125}$I TSH to membranes was observed only in transfected cells. The displacement curve of the label by TSH presented characteristics very similar to that obtained with membranes from dog thyrocytes (half-maximal displacement at 0.4 nM and 0.16 nM for cos cells and thyrocytes, respectively) (FIG. 4c). The slight rightward shift of the displacement curve obtained with Cos7 cell membranes may reflect the higher amount of receptors in this system.

The cDNA coding for the dog TSH receptor was sequenced completely. The sequence is given in FIG. 5.

d) Comparison of TSHr with LH-CGr

Comparison of the TSH receptor with the LH-CG receptor cloned recently (15, 16) reveals interesting common characteristics which make them members of a new subfamily of G-protein coupled receptors. They both display a long aminoterminal extension containing multiple sites for N glycosylation (five in the TSH receptor). The TSH receptor has an extra 52 residue insert close to the junction between the putative extracellular domain and the first transmembrane segment (FIG. 2a). The overall sequence similarity between the extracellular domains of the TSH and LH-CG receptors is 45% (FIG. 2a). The similarity between a segment of soybean lectin and the rat LH receptor (15) is not conserved in the TSH receptor, which suggests that it may be fortuitous. The C-terminal half of the TSH receptor containing the transmembrane segments is 70% similar to both the pig and rat LH receptors (FIG. 2a). The homology is particularly impressive in the transmembrane segments themselves, where stretches of up to 24 identical residues are observed in a row (transmembrane region III). Also, the carboxyl terminal region of the third putative intracellular loop, which is particularly short in TSH and LH receptors and which has been implicated in the interaction with $G_{\alpha s}$ (8, 9), is identical in both receptor types. This pattern of similarities gives support to the view that the extracellular domain would be involved in the recognition of the ligands [(4)], while the membrane-inserted domain would be responsible for the activation of $G_{\alpha s}$ (15, 16). Together, the TSH and LH-CG receptors, and HGMP09 (there is strong preliminary evidence that HGMP09 could actually be the FSH receptor (7)) constitute clearly a distinct subfamily of G-protein coupled receptors. A sequence similarity dendrogram (17) including most of the G-protein coupled receptors cloned to date demonstrates both their close relationships and their distance from the bulk of the other receptors (FIG. 2b). The complete sequence of the FSH receptor will reveal whether the known ability of LH-CG to stimulate the TSH receptor (18) is reflected by a higher sequence similarity of the extracellular domains of LH and TSH receptors.

e) Identification of a dog TSHr variant

Screening of the dog thyroid cDNA library (30) with the HGMP09 clone (thought to be part of the FSH receptor), gave rise to 16 positive clones out of the 840,000 screened plaques. Hybridization was carried out at 42° C. in 35% formamide and the filters were washed at 65° C. in 2×SSC, 0.1% SDS before autoradiography. 12 clones were purified to homogeneity and analyzed by EcoRI digestion. Three clones (dTSHR1, dTSHR2 and dTSHR3) were subcloned in M13mp18 and pBS vectors. dTSHR1 and dTSHR2 consisted of two EcoRI fragments of respectively 2800 and 1500 bp. dTSHR3 was shorter, and consisted of 2200 and 1500 bp EcoRI fragments. Restriction analysis of the 2800 bp fragments of dTSHR1 and dTSHR2 revealed slight differences in the restriction map, the main discordance being the presence of a PstI restriction site in dTSHR1 and its absence in dTSGR2. dTSHR1 was sequenced completely and revealed an open reading frame of 764 codons which was identified as the thyrotropin receptor by expression of the cDNA in oocytes and cell cultures (see example I(b)+ FIG. 5). dTSHR3 was shown by sequencing to be completely colinear with dTSHR1 but this cloned lacked 600 bp at its 5' end. Because of the difference in the restriction map of dTSHR1 and dTSHR2, this latter clone was also sequenced on both strands.

Figure 6:
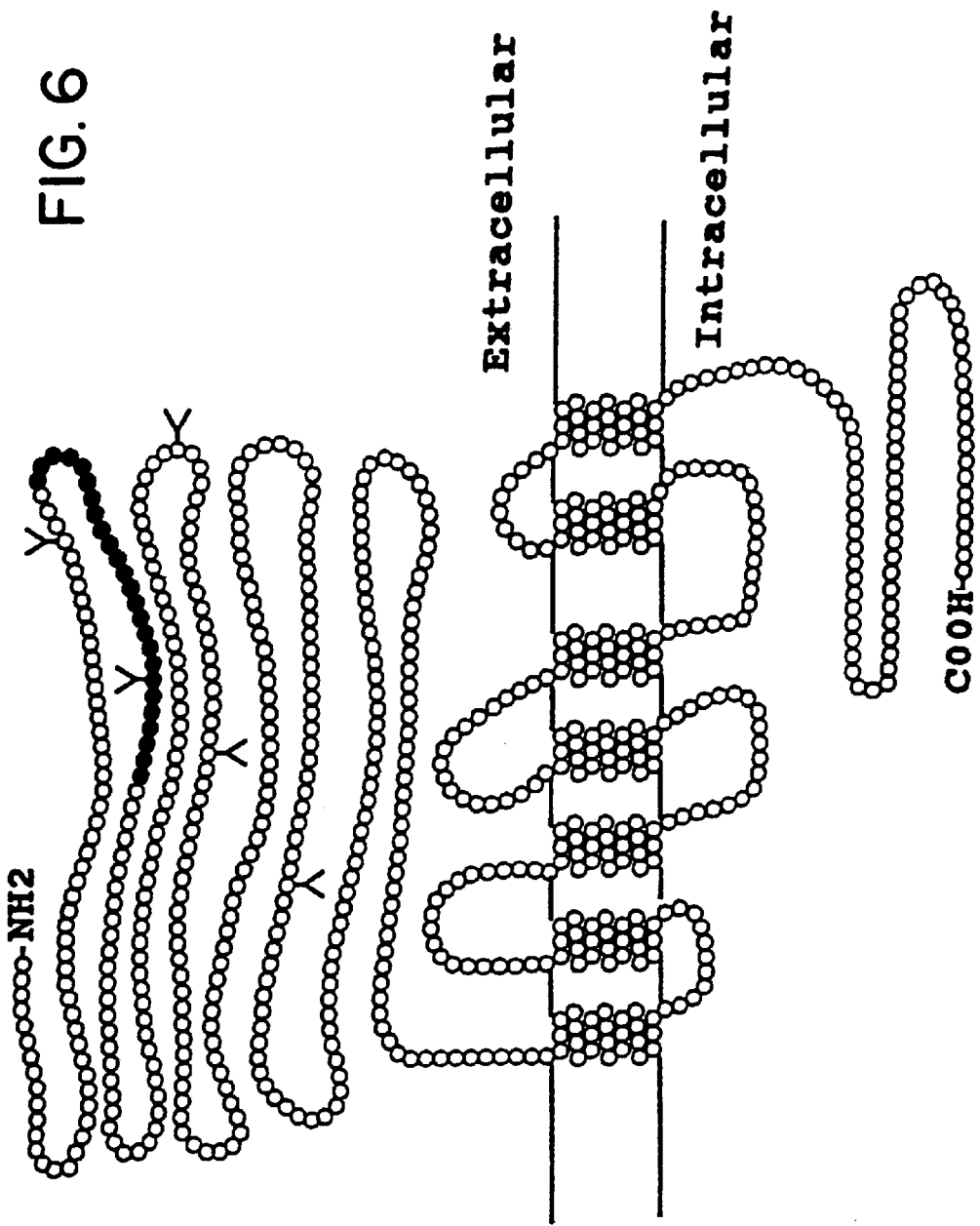
FIG. 6 is a schematic representation of the dog thyrotropin receptor, showing the 7 putative transmembrane segments and the large NH2 terminal extracellular domain (to the exclusion of the signal peptide). The amino-acids deleted in the variant form are indicated in black. The five putative glycosylation sites are shown.

The sequence revealed a number of mutations when compared with the dTSHR1 clone. A total of 5 mutations, including two single base substitutions, one single base deletion, one single base insertion and one 5 base insertion were found scattered in the 2060 bp long 3' untranslated region (not shown). However, the main difference between dTSHR2 and dTSHR1 was located in the coding region, and consisted in a 75 bp deletion located 240 bp after the start codon. The corresponding 25 amino-acids deletion in the protein itself is located in the long NH2 terminal extracellular domain which is characteristic of the TSH receptor (25) and its recently cloned close relative, the LH receptor (15, 16) (FIG. 6). As in the LH receptor, the NH2 terminal part of the thyrotropin receptor is characterized by an imperfect repeat structure that can be aligned as indicated in FIG. 7. These repeats are similar in structure to the leucine-rich repeats found in the various proteins comprising the family of leucine-rich glycoproteins (26, 15), and references therein). The deletion in the dTSHR2 clone corresponds exactly to one of these repeats, in a region of the protein where the repeat length is regular and their alignment unambiguous. The existence of such variant reinforces considerably the significance of this repeated structure and sets up interesting questions concerning its functional meaning and the structure of the chromosomal gene.

The extracellular domains of TSH and LH receptors are apparently responsible for the ligand binding (4). The deleted repeat also contains one of the 5 consensus sequences for N-glycosylation. Glycosylation of the TSH receptor could be important for ligand binding or signal transduction. If, and to what extent, the lack of this repeat influences the binding capabilities and/or the function of the receptor variant, is not yet known. Comparison of cell lines expressing this variant with the presently available stable transfectants expressing the full size receptor should partially answer this question. The functional analysis of other in-vitro generated mutants of the TSH receptor will complete the study.

The deletion of a full repeat gives also some insight on the structure of the TSH receptor gene. It is highly probable that the repeat unit corresponds to a complete exon, and it is therefore possible that all repeats would be separated by introns. It is interesting to note that most of the genes coding for G-protein coupled receptors are completely devoid of intronic structures. The functional or evolutionary significance of this observation is not known, but a highly fragmented exonic structure of the glycoprotein hormone receptor genes would be in clear contrast to the rest of the receptor family.

II—Cloning of the Human TSHr

A human lambda gt11 cDNA library (29) was screened with a fragment of the dog TSHr (25). Out of the 218 clones scored as positive (1/6000), 24 were plaque-purified to homogeneity and the size of the inserts was determined. Two clones which harbored inserts of 2370 bp and 3050 bp, respectively, were subcloned as overlapping fragments in M13 derivatives and sequenced (FIG. 12). A total of 4272 bp were determined in which a 2292 bp open reading frame was identified. When translated into protein, the coding sequence showed an overall 90.3% similarity with the dog TSHr (FIG. 8) [1]. It displayed all the characteristics described recently for the subfamily of G protein-coupled receptors binding glycoprotein hormones (25, 15, 16); a signal peptide (20 residues) followed by a large putative extracellular domain (398 residues) containing 5 sites for N-glycosylation, connected to a 346 residue carboxyl-terminal domain containing seven putative transmembrane segments (FIG. 8). It has been suggested that the amino-terminal domain, which is not found in other G protein-coupled receptors, might correspond to the region involved in the binding of the bulky pituitary and placental glycoprotein hormones (25, 15, 16).

Variants of the hTSHr

When probed with the putative human TSHr, a Northern blot of RNA from human placenta, testis and thyroid reveaeld two major 4.6 and 4.4 kb thyroid-specific transcripts. Minor thyroid-specific RNA species of smaller size were also observed. Although the former could simply correspond to multiple polyadenylation sites in the 3' region of the gene, this situation is reminiscent of what has been observed for the porcine LH-CG receptor. In this case, multiple transcripts were found to correspond to variants of the receptor cDNA lacking the potential to encode the membrane spanning segments (16). Whether this observation with important implications on receptor function and regulation also applies to the human TSHr will await sequencing of additional clones from the cDNA library.

Expression of hTSHr

To provide definite proof that the clones isolated encoded a human TSH receptor, the coding sequence was inserted in the SV40-based vector pSVL, and the resulting construct transfected in Cos-7 cells (24). Membranes prepared from transfected cells demonstrated specific binding of [$^{125}$I]TSH (FIG. 9). The unlabelled competitor TSH was bovine. The characteristics of the displacement curve with unlabelled TSH were similar to those observed with the dog TSHr assayed under similar conditions (half maximal displacement around 0.5 nM) (25).

From the sequence similarity with dog TSHr, the tissue specific expression of the corresponding transcripts and the binding studies on membranes from transfected COS-7 cells, it was concluded that a bona fide human TSHr has been cloned.

Antibodies to hTSHr

To investigate the relevance of the cloned human TSHr to thyroid autoimmunity, competition was tested between [$^{125}$I]TSH and immunoglobulins prepared from patients, for binding to the recombinant receptor expressed in Cos-7 cells (FIG. 10). Immunoglobulins were prepared from the serum of patients or normal individuals by ammonium sulphate precipitation. They were dissolved in water and dialysed extensively against Dulbecco's modified Eagle medium. While immunoglobulins from normal individuals did not displace [$^{125}$I]TSH, samples from two patients with idiopathic myxoedema clearly did, in a dose-dependant manner. The steep dose-response which was observed suggests that immunoglobulins from these patients present a very high affinity for the recombinant receptor. When samples from two patients with Graves' disease having high levels of thyroid stimulating immunoglobulins in the circulation were tested, one of them showed limited ability to displace labelled TSH under the conditions of the assay (FIG. 10). The difference in the potency of these two categories of immunoglobulins to displace TSH from the receptor expressed in Cos-7 cells may reflect differences in their affinity for a common antigen. Alternatively, despite previous studies suggesting that both stimulating and blocking antibodies would bind to the same part of the TSHr (26, 27), it may correspond to more basic differences in the actual nature of their respective antigenic targets. Studies where binding activity of a larger collection of immunoglobulins are compared to their ability to activate adenylate cyclase in permanently transfected cells will help to clarify this point.

BIBLIOGRAPHY

1. J. E. Dumont, G. Vassart & S. Refetoff, in The Metabolic Bases of Inherited Diseases, C. R. Scrivers, A. L. Beaudet, W. S. Sly & D. Vale eds. McGraw-Hill, pp 1843–1880 (1989).
2. I. A. Kourides, J. A. Gurr & O. Wolw, Rec. Progr. Horm. Res. 40, 79–120 (1984)
3. F. Ribeiro-Neto, L. Birnbaumer and J M. B. Field, Mol. Endo. 1, pp 482–490 (1987).
4. B. Rees-Smith, S. M. McLachlan & J. Furmaniak, Endocrine Rev. 9, 106–121 (1988).
5. R. K. Saiki et al., Science 239, pp. 487–491 (1988).
6. F. Libert et al., Science 244, pp. 569–572 (1988).
7. M. Parmentier et al; to be published elsewhere.
8. B. F. O'Dowd, et al. J. Biol. Chem. 263, 15985–15992 (1988).
9. C. Strader, I. S. Sigal & R. Dixon. FASEB J 3, 1825–1832 (1989)
10. S. Lissitzky, G. Fayet and B. Verrier. Adv. Cyclic Nucl. Res. 5, 133–152 (1975).
11. G. von Heijne, Nucl. Acids Res. 14, 4683 (1986).
12. B. P. Schimmer, in Functionally Differentiated cell lines. pp 61–92. G. Sato, ed. AlanR. Riss Inc. (1981) N.Y.
13. C. Maenhaut & F. Libert, submitted. Y1 cells were grown as monolayers as described (12). 1 $mm^2$ areas were marked on the bottom of the dishes and all cells in these areas were microinjected with mRNA at 0.25 ug/ul in water. mRNA was synthesized from TSH receptor cDNA subcloned in pSP64 (Promega). After 30 min;, TSH was added and the cells were photographed 120 min. later. The morphological changes (stable for 20 hours) were observed with TSH concentrations down to 0.1 nM. FSH, LH and hCG were ineffective (not shown).
14. J. Van Sande, P. Cochaux and J. E. Dumont. FEBS Lett. 150, 137–141 (1982).
15. K. C. McFarland et al., Science 245, 494 (1989).
16. H Loosfelt et al., ibid 245, 525, (1989).
17. D. G. Higgins and P. M. Sharp, Gene, 73, 237–244 (1988).
18 J. G. Kenimer, J. M. Hershman & H. P. Higgins. J. Clin. Endpe. Metab. 40, 482 (1975).
19. T. Maniatis, E. F. Fritsch and J. Sambrook, (1982) In Molecular Cloning: A Laboratory Manual (Cold Spring Harbor Laboratory Press, New York).
20. P. Roger et al. Eur. J. Biochem. 152, 239–245 (1985).
21. F. Sanger, S. Nicklen & A. R. Coulson. Proc Natl. Acad. SCi. U.S.A. 74, 5463 (1977). S. Henikoff. Gene 28, 351 (1984).
22. B. K. Kobilka et al. J. Biol. Chem. 262, 7321 (1987).
23. G. Wong, Y. S. et al. Science 228, 810–815 (1985).
24. R. A. F. Dixon et al. Nature 326, 73–77 (1987).
25. Parmentier, M., Libert, F., Maenhaut, C., Lefort, A., Gerard, C., Perret, J., Van Sande, J, Dumont J. E. and Vassart, G. (1989). Submitted.
26. Takahashi, N., Takahashi, Y. and Putman, F. W. (1985). Proc. Natl. Acad. Sci. U.S.A. 82, 1906.
27. Davies Jones, E., Hashim, F., Creagh, F. Williams, S. and Rees Smith, B. (1985) Mol. Cell. Endo. 41, 257–265.
28. Amino, N., Watanabe, Y., Tamaki, H., Iwatani, Y; and Miyai, K. (1987) Clin. Endo. 27, 615–620.
29. Libert, F., Ruel, J., Ludgate, M., Swillens, S., Alexander, N., Vassart, G. and Dinsart, C. (1987) EMBO J. T, 4193–4196.
30. Lefort, A., Lecocq, R., Libert, F., Lamy, F., Swillens, S., Vassart, G. and Dumont, J. E. (1989) EMBO J. 8, 111–116.

SEQUENCE LISTING (1) GENERAL INFORMATION:

(iii) NUMBER OF SEQUENCES: 62

(2) INFORMATION FOR SEQ ID NO:1:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION: 4
      (D) OTHER INFORMATION: /label= Xaa
          /note= "A or P"

(ix) FEATURE:
      (A) NAME/KEY: Modified-site
      (B) LOCATION: 5

```
            (D) OTHER INFORMATION: /label= Xaa
                /note= "D or P"

(ix) FEATURE:
            (A) NAME/KEY: Modified-site
            (B) LOCATION: 8
            (D) OTHER INFORMATION: /label= Xaa
                /note= "Q or H"

(ix) FEATURE:
            (A) NAME/KEY: Modified-site
            (B) LOCATION: 10
            (D) OTHER INFORMATION: /label= Xaa
                /note= "V or A"

(ix) FEATURE:
            (A) NAME/KEY: Modified-site
            (B) LOCATION: 14
            (D) OTHER INFORMATION: /label= Xaa
                /note= "D or A"

(ix) FEATURE:
            (A) NAME/KEY: Modified-site
            (B) LOCATION: 18
            (D) OTHER INFORMATION: /label= Xaa
                /note= "D or S"

(xi) SEQUENCE DESCRIPTION: SEQ ID NO:1:

Met Arg Pro Xaa Xaa Leu Leu Xaa Leu Xaa Leu Leu Leu Xaa Leu Pro
1               5                   10                  15

Arg Xaa Leu (2) INFORMATION FOR SEQ ID NO:2:

(i) SEQUENCE CHARACTERISTICS:
            (A) LENGTH: 391 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /label= Xaa
                /note= "K or M"

(ix) FEATURE:
            (A) NAME/KEY: Modified-site
            (B) LOCATION: 6
            (D) OTHER INFORMATION: /label= Xaa
                /note= "S or P"

(ix) FEATURE:
            (A) NAME/KEY: Modified-site
            (B) LOCATION: 16
            (D) OTHER INFORMATION: /label= Xaa
                /note= "E or D"

(ix) FEATURE:
            (A) NAME/KEY: Modified-site
            (B) LOCATION: 26
            (D) OTHER INFORMATION: /label= Xaa
                /note= "Q or H"

(ix) FEATURE:
            (A) NAME/KEY: Modified-site
            (B) LOCATION: 30
            (D) OTHER INFORMATION: /label= Xaa
                /note= "S or T"

(ix) FEATURE:
            (A) NAME/KEY: Modified-site
            (B) LOCATION: 40
```

```
            (D) OTHER INFORMATION: /label= Xaa
                /note= "L or F"

(ix) FEATURE:
     (A) NAME/KEY: Modified-site
     (B) LOCATION: 44
     (D) OTHER INFORMATION: /label= Xaa
         /note= "H or Q"

(ix) FEATURE:
     (A) NAME/KEY: Modified-site
     (B) LOCATION: 46
     (D) OTHER INFORMATION: /label= Xaa
         /note= "R or K"

(ix) FEATURE:
     (A) NAME/KEY: Modified-site
     (B) LOCATION: 51
     (D) OTHER INFORMATION: /label= Xaa
         /note= "H or R"

(ix) FEATURE:
     (A) NAME/KEY: Modified-site
     (B) LOCATION: 64
     (D) OTHER INFORMATION: /label= Xaa
         /note= "L or V"

(ix) FEATURE:
     (A) NAME/KEY: Modified-site
     (B) LOCATION: 68
     (D) OTHER INFORMATION: /label= Xaa
         /note= "L or A"

(ix) FEATURE:
     (A) NAME/KEY: Modified-site
     (B) LOCATION: 72
     (D) OTHER INFORMATION: /label= Xaa
         /note= "Q or R"

(ix) FEATURE:
     (A) NAME/KEY: Modified-site
     (B) LOCATION: 84
     (D) OTHER INFORMATION: /label= Xaa
         /note= "V or M"

(ix) FEATURE:
     (A) NAME/KEY: Modified-site
     (B) LOCATION: 94
     (D) OTHER INFORMATION: /label= Xaa
         /note= "N or S"

(ix) FEATURE:
     (A) NAME/KEY: Modified-site
     (B) LOCATION: 97
     (D) OTHER INFORMATION: /label= Xaa
         /note= "Y or S"

(ix) FEATURE:
     (A) NAME/KEY: Modified-site
     (B) LOCATION: 120
     (D) OTHER INFORMATION: /label= Xaa
         /note= "K or G"

(ix) FEATURE:
     (A) NAME/KEY: Modified-site
     (B) LOCATION: 121
     (D) OTHER INFORMATION: /label= Xaa
         /note= "M or V"

(ix) FEATURE:
     (A) NAME/KEY: Modified-site
     (B) LOCATION: 125
     (D) OTHER INFORMATION: /label= Xaa
         /note= "L or V"

(ix) FEATURE:
     (A) NAME/KEY: Modified-site
     (B) LOCATION: 133
```

```
            (D) OTHER INFORMATION: /label= Xaa
                /note= "I or V"

(ix) FEATURE:
     (A) NAME/KEY: Modified-site
     (B) LOCATION: 146
     (D) OTHER INFORMATION: /label= Xaa
         /note= "T or A"

(ix) FEATURE:
     (A) NAME/KEY: Modified-site
     (B) LOCATION: 150
     (D) OTHER INFORMATION: /label= Xaa
         /note= "V or A"

(ix) FEATURE:
     (A) NAME/KEY: Modified-site
     (B) LOCATION: 173
     (D) OTHER INFORMATION: /label= Xaa
         /note= "V or I"

(ix) FEATURE:
     (A) NAME/KEY: Modified-site
     (B) LOCATION: 176
     (D) OTHER INFORMATION: /label= Xaa
         /note= "Y or H"

(ix) FEATURE:
     (A) NAME/KEY: Modified-site
     (B) LOCATION: 195
     (D) OTHER INFORMATION: /label= Xaa
         /note= "T or S"

(ix) FEATURE:
     (A) NAME/KEY: Modified-site
     (B) LOCATION: 196
     (D) OTHER INFORMATION: /label= Xaa
         /note= "V or A"

(ix) FEATURE:
     (A) NAME/KEY: Modified-site
     (B) LOCATION: 210
     (D) OTHER INFORMATION: /label= Xaa
         /note= "S or T"

(ix) FEATURE:
     (A) NAME/KEY: Modified-site
     (B) LOCATION: 216
     (D) OTHER INFORMATION: /label= Xaa
         /note= "Q or Y"

(ix) FEATURE:
     (A) NAME/KEY: Modified-site
     (B) LOCATION: 287
     (D) OTHER INFORMATION: /label= Xaa
         /note= "M or I"

(ix) FEATURE:
     (A) NAME/KEY: Modified-site
     (B) LOCATION: 288
     (D) OTHER INFORMATION: /label= Xaa
         /note= "Q or R"

(ix) FEATURE:
     (A) NAME/KEY: Modified-site
     (B) LOCATION: 298
     (D) OTHER INFORMATION: /label= Xaa
         /note= "A or T"

(ix) FEATURE:
     (A) NAME/KEY: Modified-site
     (B) LOCATION: 301
     (D) OTHER INFORMATION: /label= Xaa
         /note= "S or G"

(ix) FEATURE:
     (A) NAME/KEY: Modified-site
     (B) LOCATION: 303
```

```
            (D) OTHER INFORMATION: /label= Xaa
                /note= "L or F"

(ix) FEATURE:
     (A) NAME/KEY: Modified-site
     (B) LOCATION: 304
     (D) OTHER INFORMATION: /label= Xaa
         /note= "H or D"

(ix) FEATURE:
     (A) NAME/KEY: Modified-site
     (B) LOCATION: 310
     (D) OTHER INFORMATION: /label= Xaa
         /note= "N or Y"

(ix) FEATURE:
     (A) NAME/KEY: Modified-site
     (B) LOCATION: 315
     (D) OTHER INFORMATION: /label= Xaa
         /note= "I or H"

(ix) FEATURE:
     (A) NAME/KEY: Modified-site
     (B) LOCATION: 316
     (D) OTHER INFORMATION: /label= Xaa
         /note= "V or A"

(ix) FEATURE:
     (A) NAME/KEY: Modified-site
     (B) LOCATION: 320
     (D) OTHER INFORMATION: /label= Xaa
         /note= "E or D"

(ix) FEATURE:
     (A) NAME/KEY: Modified-site
     (B) LOCATION: 321
     (D) OTHER INFORMATION: /label= Xaa
         /note= "K or N"

(ix) FEATURE:
     (A) NAME/KEY: Modified-site
     (B) LOCATION: 323
     (D) OTHER INFORMATION: /label= Xaa
         /note= "K or Q"

(ix) FEATURE:
     (A) NAME/KEY: Modified-site
     (B) LOCATION: 328
     (D) OTHER INFORMATION: /label= Xaa
         /note= "H or D"

(ix) FEATURE:
     (A) NAME/KEY: Modified-site
     (B) LOCATION: 329
     (D) OTHER INFORMATION: /label= Xaa
         /note= "N or S"

(ix) FEATURE:
     (A) NAME/KEY: Modified-site
     (B) LOCATION: 331
     (D) OTHER INFORMATION: /label= Xaa
         /note= "A or S"

(ix) FEATURE:
     (A) NAME/KEY: Modified-site
     (B) LOCATION: 345
     (D) OTHER INFORMATION: /label= Xaa
         /note= "I or L"

(ix) FEATURE:
     (A) NAME/KEY: Modified-site
     (B) LOCATION: 370
     (D) OTHER INFORMATION: /label= Xaa
         /note= "I or V"

(ix) FEATURE:
     (A) NAME/KEY: Modified-site
     (B) LOCATION: 373
```

(D) OTHER INFORMATION: /label= Xaa
    /note= "D or G"

(ix) FEATURE:
    (A) NAME/KEY: Modified-site
    (B) LOCATION: 374
    (D) OTHER INFORMATION: /label= Xaa
        /note= "S or N"

(xi) SEQUENCE DESCRIPTION: SEQ ID NO:2:

```
Gly Gly Xaa Gly Cys Xaa Ser Pro Pro Cys Glu Cys His Gln Glu Xaa
1               5                   10                  15

Asp Phe Arg Val Thr Cys Lys Asp Ile Xaa Arg Ile Pro Xaa Leu Pro
            20                  25                  30

Pro Ser Thr Gln Thr Leu Lys Xaa Ile Glu Thr Xaa Leu Xaa Thr Ile
        35                  40                  45

Pro Ser Xaa Ala Phe Ser Asn Leu Pro Asn Ile Ser Arg Ile Tyr Xaa
    50                  55                  60

Ser Ile Asp Xaa Thr Leu Gln Xaa Leu Glu Ser His Ser Phe Tyr Asn
65                  70                  75                  80

Leu Ser Lys Xaa Thr His Ile Glu Ile Arg Asn Thr Arg Xaa Leu Thr
            85                  90                  95

Xaa Ile Asp Pro Asp Ala Leu Lys Glu Leu Pro Leu Leu Lys Phe Leu
            100                 105                 110

Gly Ile Phe Asn Thr Gly Leu Xaa Xaa Phe Pro Asp Xaa Thr Lys Val
            115                 120                 125

Tyr Ser Thr Asp Xaa Phe Phe Ile Leu Glu Ile Thr Asp Asn Pro Tyr
        130                 135                 140

Met Xaa Ser Ile Pro Xaa Asn Ala Phe Gln Gly Leu Cys Asn Glu Thr
145                 150                 155                 160

Leu Thr Leu Lys Leu Tyr Asn Asn Gly Phe Thr Ser Xaa Gln Gly Xaa
            165                 170                 175

Ala Phe Asn Gly Thr Lys Leu Asp Ala Val Tyr Leu Asn Lys Asn Lys
            180                 185                 190

Tyr Leu Xaa Xaa Ile Asp Lys Asp Ala Phe Gly Gly Val Tyr Ser Gly
            195                 200                 205

Pro Xaa Leu Leu Asp Val Ser Xaa Thr Ser Val Thr Ala Leu Pro Ser
    210                 215                 220

Lys Gly Leu Glu His Leu Lys Glu Leu Ile Ala Arg Asn Thr Trp Thr
225                 230                 235                 240

Leu Lys Lys Leu Pro Leu Ser Leu Ser Phe Leu His Leu Thr Arg Ala
            245                 250                 255

Asp Leu Ser Tyr Pro Ser His Cys Cys Ala Phe Lys Asn Gln Lys Lys
            260                 265                 270

Ile Arg Gly Ile Leu Glu Ser Leu Met Cys Asn Glu Ser Ser Xaa Xaa
            275                 280                 285

Ser Leu Arg Gln Arg Lys Ser Val Asn Xaa Leu Asn Xaa Pro Xaa Xaa
            290                 295                 300

Gln Glu Tyr Glu Glu Xaa Leu Gly Asp Ser Xaa Gly Tyr Lys Xaa
305                 310                 315                 320

Xaa Ser Xaa Phe Gln Asp Thr Xaa Xaa Asn Xaa His Tyr Tyr Val Phe
            325                 330                 335

Phe Glu Glu Gln Glu Asp Glu Ile Xaa Gly Phe Gly Gln Glu Leu Lys
            340                 345                 350

Asn Pro Gln Glu Glu Thr Leu Gln Ala Phe Asp Ser His Tyr Asp Tyr
            355                 360                 365
```

```
Thr Xaa Cys Gly Xaa Xaa Glu Asp Met Val Cys Thr Pro Lys Ser Asp
    370             375                 380

Glu Phe Asn Pro Cys Glu Asp
385             390
```

(2) INFORMATION FOR SEQ ID NO:3:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 27
        (D) OTHER INFORMATION: /label= Xaa
            /note= "L or I"

(ix) FEATURE:
        (A) NAME/KEY: Modified-site
        (B) LOCATION: 28
        (D) OTHER INFORMATION: /label= Xaa
            /note= "I or V"

(xi) SEQUENCE DESCRIPTION: SEQ ID NO:3:

```
Ile Met Gly Tyr Lys Phe Leu Arg Ile Val Val Trp Phe Val Ser Leu
1               5                   10                  15

Leu Ala Leu Leu Gly Asn Val Phe Val Leu Xaa Xaa Leu Leu Thr Ser
            20                  25              30

His Tyr Lys
        35
```

(2) INFORMATION FOR SEQ ID NO:4:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label= Xaa
            /note= "N or T"

(ix) FEATURE:
        (A) NAME/KEY: Modified-site
        (B) LOCATION: 18
        (D) OTHER INFORMATION: /label= Xaa
            /note= "M or I"

(ix) FEATURE:
        (A) NAME/KEY: Modified-site
        (B) LOCATION: 20
        (D) OTHER INFORMATION: /label= Xaa
            /note= "M or I"

(ix) FEATURE:
        (A) NAME/KEY: Modified-site
        (B) LOCATION: 30
        (D) OTHER INFORMATION: /label= Xaa
            /note= "L or I"

(ix) FEATURE:
        (A) NAME/KEY: Modified-site
        (B) LOCATION: 31

```
           (D) OTHER INFORMATION: /label= Xaa
               /note= "Y or H"

(ix) FEATURE:
           (A) NAME/KEY: Modified-site
           (B) LOCATION: 33
           (D) OTHER INFORMATION: /label= Xaa
               /note= "H or K"

(ix) FEATURE:
           (A) NAME/KEY: Modified-site
           (B) LOCATION: 35
           (D) OTHER INFORMATION: /label= Xaa
               /note= "E or Q"

(ix) FEATURE:
           (A) NAME/KEY: Modified-site
           (B) LOCATION: 37
           (D) OTHER INFORMATION: /label= Xaa
               /note= "Y or H"

(ix) FEATURE:
           (A) NAME/KEY: Modified-site
           (B) LOCATION: 39
           (D) OTHER INFORMATION: /label= Xaa
               /note= "Y or H"

(xi) SEQUENCE DESCRIPTION: SEQ ID NO:4:

Leu Xaa Val Pro Arg Phe Leu Met Cys Asn Leu Ala Phe Ala Asp Phe
1               5                   10                  15

Cys Xaa Gly Xaa Tyr Leu Leu Leu Ile Ala Ser Val Asp Xaa Xaa Thr
            20                  25                  30

Xaa Ser Xaa Tyr Xaa Asn Xaa Ala
        35                  40

(2) INFORMATION FOR SEQ ID NO:5:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:5:

Ile Asp Trp Gln Thr Gly Pro Gly Cys
1               5

(2) INFORMATION FOR SEQ ID NO:6:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:6:

Ile Asp Trp Gln Thr Gly Ala Gly Cys
1               5

(2) INFORMATION FOR SEQ ID NO:7:

(i) SEQUENCE CHARACTERISTICS:
          (A) LENGTH: 23 amino acids
          (B) TYPE: amino acid
          (C) STRANDEDNESS: single
          (D) TOPOLOGY: linear
```

```
        (ii) MOLECULE TYPE: peptide (ix) FEATURE:
              (A) NAME/KEY: Modified-site
              (B) LOCATION: 1
              (D) OTHER INFORMATION: /label= Xaa
                  /note= "N or D"

(ix) FEATURE:
              (A) NAME/KEY: Modified-site
              (B) LOCATION: 2
              (D) OTHER INFORMATION: /label= Xaa
                  /note= "T or A"

(xi) SEQUENCE DESCRIPTION: SEQ ID NO:7:

Xaa Xaa Ala Gly Phe Phe Thr Val Phe Ala Ser Glu Leu Ser Val Tyr
1               5                   10                  15

Thr Leu Thr Val Ile Thr Leu
            20

(2) INFORMATION FOR SEQ ID NO:8:

(i) SEQUENCE CHARACTERISTICS:
              (A) LENGTH: 13 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 4
              (D) OTHER INFORMATION: /label= Xaa
                  /note= "Y or H"

(ix) FEATURE:
              (A) NAME/KEY: Modified-site
              (B) LOCATION: 5
              (D) OTHER INFORMATION: /label= Xaa
                  /note= "A or T"

(ix) FEATURE:
              (A) NAME/KEY: Modified-site
              (B) LOCATION: 8
              (D) OTHER INFORMATION: /label= Xaa
                  /note= "F or H"

(ix) FEATURE:
              (A) NAME/KEY: Modified-site
              (B) LOCATION: 11
              (D) OTHER INFORMATION: /label= Xaa
                  /note= "R or Q"

(xi) SEQUENCE DESCRIPTION: SEQ ID NO:8:

Glu Arg Trp Xaa Xaa Ile Thr Xaa Ala Met Xaa Leu Asp
1               5                   10

(2) INFORMATION FOR SEQ ID NO:9:

(i) SEQUENCE CHARACTERISTICS:
              (A) LENGTH: 40 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /label= Xaa
                  /note= "R or C"
```

```
     (ix) FEATURE:
           (A) NAME/KEY: Modified-site
           (B) LOCATION: 3
           (D) OTHER INFORMATION: /label= Xaa
               /note= "I or V"

(ix) FEATURE:
           (A) NAME/KEY: Modified-site
           (B) LOCATION: 4
           (D) OTHER INFORMATION: /label= Xaa
               /note= "R or Q"

(ix) FEATURE:
           (A) NAME/KEY: Modified-site
           (B) LOCATION: 9
           (D) OTHER INFORMATION: /label= Xaa
               /note= "C or Y or A"

(ix) FEATURE:
           (A) NAME/KEY: Modified-site
           (B) LOCATION: 10
           (D) OTHER INFORMATION: /label= Xaa
               /note= "A or S"

(ix) FEATURE:
           (A) NAME/KEY: Modified-site
           (B) LOCATION: 11
           (D) OTHER INFORMATION: /label= Xaa
               /note= "I or V"

(ix) FEATURE:
           (A) NAME/KEY: Modified-site
           (B) LOCATION: 15
           (D) OTHER INFORMATION: /label= Xaa
               /note= "G or M"

(ix) FEATURE:
           (A) NAME/KEY: Modified-site
           (B) LOCATION: 17
           (D) OTHER INFORMATION: /label= Xaa
               /note= "V or I"

(ix) FEATURE:
           (A) NAME/KEY: Modified-site
           (B) LOCATION: 18
           (D) OTHER INFORMATION: /label= Xaa
               /note= "C or F"

(ix) FEATURE:
           (A) NAME/KEY: Modified-site
           (B) LOCATION: 19
           (D) OTHER INFORMATION: /label= Xaa
               /note= "C or A"

(ix) FEATURE:
           (A) NAME/KEY: Modified-site
           (B) LOCATION: 21
           (D) OTHER INFORMATION: /label= Xaa
               /note= "L or A"

(ix) FEATURE:
           (A) NAME/KEY: Modified-site
           (B) LOCATION: 22
           (D) OTHER INFORMATION: /label= Xaa
               /note= "L or A"

(ix) FEATURE:
           (A) NAME/KEY: Modified-site
           (B) LOCATION: 25
           (D) OTHER INFORMATION: /label= Xaa
               /note= "L or F"

(ix) FEATURE:
           (A) NAME/KEY: Modified-site
           (B) LOCATION: 27
           (D) OTHER INFORMATION: /label= Xaa
               /note= "L or I"
```

```
    (ix) FEATURE:
         (A) NAME/KEY: Modified-site
         (B) LOCATION: 28
         (D) OTHER INFORMATION: /label= Xaa
             /note= "V or F"

(ix) FEATURE:
         (A) NAME/KEY: Modified-site
         (B) LOCATION: 34
         (D) OTHER INFORMATION: /label= Xaa
             /note= "A or M"

(xi) SEQUENCE DESCRIPTION: SEQ ID NO:9:

Xaa Lys Xaa Xaa Leu Arg His Ala Xaa Xaa Xaa Met Val Gly Xaa Trp
 1               5                  10                  15

Xaa Xaa Xaa Phe Xaa Xaa Ala Leu Xaa Pro Xaa Xaa Gly Ile Ser Ser
            20                  25                  30

Tyr Xaa Lys Val Ser Ile Cys Leu
        35                  40

(2) INFORMATION FOR SEQ ID NO:10:

(i) SEQUENCE CHARACTERISTICS:
         (A) LENGTH: 40 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: 4
         (D) OTHER INFORMATION: /label= Xaa
             /note= "T or I"

(ix) FEATURE:
         (A) NAME/KEY: Modified-site
         (B) LOCATION: 5
         (D) OTHER INFORMATION: /label= Xaa
             /note= "E or D"

(ix) FEATURE:
         (A) NAME/KEY: Modified-site
         (B) LOCATION: 6
         (D) OTHER INFORMATION: /label= Xaa
             /note= "T or S"

(ix) FEATURE:
         (A) NAME/KEY: Modified-site
         (B) LOCATION: 9
         (D) OTHER INFORMATION: /label= Xaa
             /note= "A or S"

(ix) FEATURE:
         (A) NAME/KEY: Modified-site
         (B) LOCATION: 10
         (D) OTHER INFORMATION: /label= Xaa
             /note= "L or Q"

(ix) FEATURE:
         (A) NAME/KEY: Modified-site
         (B) LOCATION: 11
         (D) OTHER INFORMATION: /label= Xaa
             /note= "A or L"

(ix) FEATURE:
         (A) NAME/KEY: Modified-site
         (B) LOCATION: 13
         (D) OTHER INFORMATION: /label= Xaa
             /note= "I or V"

(ix) FEATURE:
         (A) NAME/KEY: Modified-site
         (B) LOCATION: 14
```

```
        (D) OTHER INFORMATION: /label= Xaa
            /note= "V or I or M"

(ix) FEATURE:
        (A) NAME/KEY: Modified-site
        (B) LOCATION: 15
        (D) OTHER INFORMATION: /label= Xaa
            /note= "F or L or S"

(ix) FEATURE:
        (A) NAME/KEY: Modified-site
        (B) LOCATION: 16
        (D) OTHER INFORMATION: /label= Xaa
            /note= "V or L"

(ix) FEATURE:
        (A) NAME/KEY: Modified-site
        (B) LOCATION: 18
        (D) OTHER INFORMATION: /label= Xaa
            /note= "T or L or V"

(ix) FEATURE:
        (A) NAME/KEY: Modified-site
        (B) LOCATION: 21
        (D) OTHER INFORMATION: /label= Xaa
            /note= "I or V"

(ix) FEATURE:
        (A) NAME/KEY: Modified-site
        (B) LOCATION: 22
        (D) OTHER INFORMATION: /label= Xaa
            /note= "V or L"

(ix) FEATURE:
        (A) NAME/KEY: Modified-site
        (B) LOCATION: 25
        (D) OTHER INFORMATION: /label= Xaa
            /note= "V or I"

(ix) FEATURE:
        (A) NAME/KEY: Modified-site
        (B) LOCATION: 29
        (D) OTHER INFORMATION: /label= Xaa
            /note= "C or S"

(xi) SEQUENCE DESCRIPTION: SEQ ID NO:10:

Pro Met Asp Xaa Xaa Xaa Pro Leu Xaa Xaa Xaa Tyr Xaa Xaa Xaa Xaa
1               5                   10                  15

Leu Xaa Leu Asn Xaa Xaa Ala Phe Xaa Ile Val Cys Xaa Cys Tyr Val
            20                  25                  30

Lys Ile Tyr Ile Thr Val Arg Asn
        35                  40

(2) INFORMATION FOR SEQ ID NO:11:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 25
        (D) OTHER INFORMATION: /label= Xaa
            /note= "I or M"

(ix) FEATURE:
        (A) NAME/KEY: Modified-site
        (B) LOCATION: 38
        (D) OTHER INFORMATION: /label= Xaa
            /note= "I or L"
```

```
        (ix) FEATURE:
            (A) NAME/KEY: Modified-site
            (B) LOCATION: 39
            (D) OTHER INFORMATION: /label= Xaa
                /note= "L or M"

(xi) SEQUENCE DESCRIPTION: SEQ ID NO:11:

Pro Gln Tyr Asn Pro Gly Asp Lys Asp Thr Lys Ile Ala Lys Arg Met
1               5                   10                  15

Ala Val Leu Ile Phe Thr Asp Phe Xaa Cys Met Ala Pro Ile Ser Phe
                20                  25                  30

Tyr Ala Leu Ser Ala Xaa Xaa Asn Lys Pro Leu Ile Thr
                35              40                  45

(2) INFORMATION FOR SEQ ID NO:12:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Val Ser Asn Ser Lys Ile Leu Leu Val Leu Phe Tyr Pro Leu Asn Ser
1               5                   10                  15

Cys Ala Asn Pro Phe Leu Tyr Ala Ile Phe Thr Lys Ala Phe Gln Arg
                20                  25                  30

Asp (2) INFORMATION FOR SEQ ID NO:13:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Val Thr Asn Ser Lys Ile Leu Leu Val Leu Phe Tyr Pro Leu Asn Ser
1               5                   10                  15

Cys Ala Asn Pro Phe Leu Tyr Ala Ile Phe Thr Lys Ala Phe Gln Arg
                20                  25                  30

Asp (2) INFORMATION FOR SEQ ID NO:14:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 24
        (D) OTHER INFORMATION: /label= Xaa
                /note= "P or S"

(ix) FEATURE:
        (A) NAME/KEY: Modified-site
        (B) LOCATION: 29
```

(D) OTHER INFORMATION: /label= Xaa
                /note= "T or A"

(ix) FEATURE:
            (A) NAME/KEY: Modified-site
            (B) LOCATION: 30
            (D) OTHER INFORMATION: /label= Xaa
                /note= "D or G"

(ix) FEATURE:
            (A) NAME/KEY: Modified-site
            (B) LOCATION: 33
            (D) OTHER INFORMATION: /label= Xaa
                /note= "V or I"

(ix) FEATURE:
            (A) NAME/KEY: Modified-site
            (B) LOCATION: 38
            (D) OTHER INFORMATION: /label= Xaa
                /note= "H or R"

(ix) FEATURE:
            (A) NAME/KEY: Modified-site
            (B) LOCATION: 43
            (D) OTHER INFORMATION: /label= Xaa
                /note= "G or S"

(ix) FEATURE:
            (A) NAME/KEY: Modified-site
            (B) LOCATION: 45
            (D) OTHER INFORMATION: /label= Xaa
                /note= "H or P"

(ix) FEATURE:
            (A) NAME/KEY: Modified-site
            (B) LOCATION: 48
            (D) OTHER INFORMATION: /label= Xaa
                /note= "E or Q"

(ix) FEATURE:
            (A) NAME/KEY: Modified-site
            (B) LOCATION: 50
            (D) OTHER INFORMATION: /label= Xaa
                /note= "V or E"

(ix) FEATURE:
            (A) NAME/KEY: Modified-site
            (B) LOCATION: 54
            (D) OTHER INFORMATION: /label= Xaa
                /note= "I or L"

(ix) FEATURE:
            (A) NAME/KEY: Modified-site
            (B) LOCATION: 62
            (D) OTHER INFORMATION: /label= Xaa
                /note= "K or N"

(ix) FEATURE:
            (A) NAME/KEY: Modified-site
            (B) LOCATION: 69
            (D) OTHER INFORMATION: /label= Xaa
                /note= "E or K"

(ix) FEATURE:
            (A) NAME/KEY: Modified-site
            (B) LOCATION: 72
            (D) OTHER INFORMATION: /label= Xaa
                /note= "M or N"

(xi) SEQUENCE DESCRIPTION: SEQ ID NO:14:

Val Phe Ile Leu Leu Ser Lys Phe Gly Ile Cys Lys Arg Gln Ala Gln
1               5                   10                  15

Ala Tyr Arg Gly Gln Arg Val Xaa Pro Lys Asn Ser Xaa Xaa Ile Gln
                20                  25                  30

Xaa Gln Lys Val Thr Xaa Asp Met Arg Gln Xaa Leu Xaa Asn Met Xaa
            35                  40                  45

```
Asp Xaa Tyr Glu Leu Xaa Glu Asn Ser His Leu Thr Pro Xaa Lys Gln
    50                  55                  60

Gly Gln Ile Ser Xaa Glu Tyr Xaa Gln Thr Val Leu
65                  70                  75
```

(2) INFORMATION FOR SEQ ID NO:15:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label= Xaa
            /note= "M or K"

(ix) FEATURE:
        (A) NAME/KEY: Modified-site
        (B) LOCATION: 5
        (D) OTHER INFORMATION: /label= Xaa
            /note= "S or P"

(ix) FEATURE:
        (A) NAME/KEY: Modified-site
        (B) LOCATION: 15
        (D) OTHER INFORMATION: /label= Xaa
            /note= "E or D"

(ix) FEATURE:
        (A) NAME/KEY: Modified-site
        (B) LOCATION: 25
        (D) OTHER INFORMATION: /label= Xaa
            /note= "Q or H"

(ix) FEATURE:
        (A) NAME/KEY: Modified-site
        (B) LOCATION: 29
        (D) OTHER INFORMATION: /label= Xaa
            /note= "S or T"

(xi) SEQUENCE DESCRIPTION: SEQ ID NO:15:

```
Gly Xaa Met Gly Cys Xaa Ser Pro Pro Cys Glu Cys His Gln Glu Xaa
1               5                   10                  15

Asp Phe Arg Val Thr Cys Lys Asp Ile Xaa Arg Ile Pro Xaa Leu Pro
                20                  25                  30

Pro Ser Thr Gln Thr
            35
```

(2) INFORMATION FOR SEQ ID NO:16:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /label= Xaa
            /note= "L or F"

(ix) FEATURE:
        (A) NAME/KEY: Modified-site
        (B) LOCATION: 7

(D) OTHER INFORMATION: /label= Xaa
            /note= "H or Q"

(ix) FEATURE:
        (A) NAME/KEY: Modified-site
        (B) LOCATION: 9
        (D) OTHER INFORMATION: /label= Xaa
            /note= "R or K"

(ix) FEATURE:
        (A) NAME/KEY: Modified-site
        (B) LOCATION: 14
        (D) OTHER INFORMATION: /label= Xaa
            /note= "H or R"

(xi) SEQUENCE DESCRIPTION: SEQ ID NO:16:

Leu Lys Xaa Ile Glu Thr Xaa Leu Xaa Thr Ile Pro Ser Xaa Ala Phe
1               5                  10                  15

Ser Asn Leu Pro Asn Ile Ser Arg
            20

(2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /label= Xaa
            /note= "V or L"

(ix) FEATURE:
        (A) NAME/KEY: Modified-site
        (B) LOCATION: 7
        (D) OTHER INFORMATION: /label= Xaa
            /note= "L or A"

(ix) FEATURE:
        (A) NAME/KEY: Modified-site
        (B) LOCATION: 11
        (D) OTHER INFORMATION: /label= Xaa
            /note= "Q or R"

(ix) FEATURE:
        (A) NAME/KEY: Modified-site
        (B) LOCATION: 23
        (D) OTHER INFORMATION: /label= Xaa
            /note= "V or M"

(xi) SEQUENCE DESCRIPTION: SEQ ID NO:17:

Ile Tyr Xaa Ser Ile Asp Xaa Thr Leu Gln Xaa Leu Glu Ser His Ser
1               5                  10                  15

Phe Tyr Asn Leu Ser Lys Xaa Thr His
            20                  25

(2) INFORMATION FOR SEQ ID NO:18:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide

```
        (ix) FEATURE:
              (A) NAME/KEY: Modified-site
              (B) LOCATION: 8
              (D) OTHER INFORMATION: /label= Xaa
                  /note= "N or S"

(ix) FEATURE:
              (A) NAME/KEY: Modified-site
              (B) LOCATION: 11
              (D) OTHER INFORMATION: /label= Xaa
                  /note= "Y or S"

(xi) SEQUENCE DESCRIPTION: SEQ ID NO:18:

Ile Glu Ile Arg Asn Thr Arg Xaa Leu Thr Xaa Ile Asp Pro Asp Ala
1               5                   10                  15

Leu Lys Glu Leu Pro Leu Leu Lys Phe
            20                  25

(2) INFORMATION FOR SEQ ID NO:19:

(i) SEQUENCE CHARACTERISTICS:
              (A) LENGTH: 25 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 9
              (D) OTHER INFORMATION: /label= Xaa
                  /note= "K or G"

(ix) FEATURE:
              (A) NAME/KEY: Modified-site
              (B) LOCATION: 10
              (D) OTHER INFORMATION: /label= Xaa
                  /note= "M or V"

(ix) FEATURE:
              (A) NAME/KEY: Modified-site
              (B) LOCATION: 14
              (D) OTHER INFORMATION: /label= Xaa
                  /note= "L or V"

(ix) FEATURE:
              (A) NAME/KEY: Modified-site
              (B) LOCATION: 22
              (D) OTHER INFORMATION: /label= Xaa
                  /note= "I or V"

(xi) SEQUENCE DESCRIPTION: SEQ ID NO:19:

Leu Gly Ile Phe Asn Thr Gly Leu Xaa Xaa Phe Pro Asp Xaa Thr Lys
1               5                   10                  15

Val Tyr Ser Thr Asp Xaa Phe Phe Ile
            20                  25

(2) INFORMATION FOR SEQ ID NO:20:

(i) SEQUENCE CHARACTERISTICS:
              (A) LENGTH: 25 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 10
              (D) OTHER INFORMATION: /label= Xaa
                  /note= "T or A"
```

```
    (ix) FEATURE:
         (A) NAME/KEY: Modified-site
         (B) LOCATION: 14
         (D) OTHER INFORMATION: /label= Xaa
             /note= "V or A"

(xi) SEQUENCE DESCRIPTION: SEQ ID NO:20:

Leu Glu Ile Thr Asp Asn Pro Tyr Met Xaa Ser Ile Pro Xaa Asn Ala
1               5                   10                  15

Phe Gln Gly Leu Cys Asn Glu Thr Leu
            20                  25

(2) INFORMATION FOR SEQ ID NO:21:

(i) SEQUENCE CHARACTERISTICS:
         (A) LENGTH: 25 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: 12
         (D) OTHER INFORMATION: /label= Xaa
             /note= "V or I"

(ix) FEATURE:
         (A) NAME/KEY: Modified-site
         (B) LOCATION: 15
         (D) OTHER INFORMATION: /label= Xaa
             /note= "Y or H"

(xi) SEQUENCE DESCRIPTION: SEQ ID NO:21:

Thr Leu Lys Leu Tyr Asn Asn Gly Phe Thr Ser Xaa Gln Gly Xaa Ala
1               5                   10                  15

Phe Asn Gly Thr Lys Leu Asp Ala Val
            20                  25

(2) INFORMATION FOR SEQ ID NO:22:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: 9
         (D) OTHER INFORMATION: /label= Xaa
             /note= "T or S"

(ix) FEATURE:
         (A) NAME/KEY: Modified-site
         (B) LOCATION: 10
         (D) OTHER INFORMATION: /label= Xaa
             /note= "V or A"

(ix) FEATURE:
         (A) NAME/KEY: Modified-site
         (B) LOCATION: 24
         (D) OTHER INFORMATION: /label= Xaa
             /note= "S or T"

(xi) SEQUENCE DESCRIPTION: SEQ ID NO:22:

Tyr Leu Asn Lys Asn Lys Tyr Leu Xaa Xaa Ile Asp Lys Asp Ala Phe
1               5                   10                  15
```

```
Gly Gly Val Tyr Ser Gly Pro Xaa
            20

(2) INFORMATION FOR SEQ ID NO:23:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Leu Leu Asp Val Ser Gln Thr Ser Val Thr Ala Leu Pro Ser Lys Gly
1               5                  10                  15

Leu Glu His Leu Lys Glu Leu Ile Ala
            20                  25

(2) INFORMATION FOR SEQ ID NO:24:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Leu Leu Asp Val Ser Tyr Thr Ser Val Thr Ala Leu Pro Ser Lys Gly
1               5                  10                  15

Leu Glu His Leu Lys Glu Leu Ile Ala
            20                  25

(2) INFORMATION FOR SEQ ID NO:25:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Arg Asn Thr Trp Thr Leu Lys Lys Leu Pro Leu Ser Leu Ser Phe Leu
1               5                  10                  15

His Leu Thr Arg Ala Asp Leu
            20

(2) INFORMATION FOR SEQ ID NO:26:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Ser Tyr Pro Ser His Cys Cys Ala Phe Lys Asn Gln Lys Lys Ile Arg
1               5                  10                  15

Gly Ile Leu Glu Ser Leu Met Cys Asn
            20                  25
```

(2) INFORMATION FOR SEQ ID NO:27:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /label= Xaa
            /note= "M or I"

(ix) FEATURE:
        (A) NAME/KEY: Modified-site
        (B) LOCATION: 5
        (D) OTHER INFORMATION: /label= Xaa
            /note= "Q or R"

(ix) FEATURE:
        (A) NAME/KEY: Modified-site
        (B) LOCATION: 15
        (D) OTHER INFORMATION: /label= Xaa
            /note= "A or T"

(ix) FEATURE:
        (A) NAME/KEY: Modified-site
        (B) LOCATION: 18
        (D) OTHER INFORMATION: /label= Xaa
            /note= "S or G"

(ix) FEATURE:
        (A) NAME/KEY: Modified-site
        (B) LOCATION: 20
        (D) OTHER INFORMATION: /label= Xaa
            /note= "L or F"

(ix) FEATURE:
        (A) NAME/KEY: Modified-site
        (B) LOCATION: 21
        (D) OTHER INFORMATION: /label= Xaa
            /note= "H or D"

(xi) SEQUENCE DESCRIPTION: SEQ ID NO:27:

Glu Ser Ser Met Xaa Xaa Leu Arg Gln Arg Lys Ser Val Asn Xaa Leu
1               5                   10                  15

Asn Xaa Pro Xaa Xaa Gln Glu Tyr Glu
            20                  25

(2) INFORMATION FOR SEQ ID NO:28:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label= Xaa
            /note= "N or Y"

(ix) FEATURE:
        (A) NAME/KEY: Modified-site
        (B) LOCATION: 7
        (D) OTHER INFORMATION: /label= Xaa
            /note= "I or H"

```
    (ix) FEATURE:
        (A) NAME/KEY: Modified-site
        (B) LOCATION: 8
        (D) OTHER INFORMATION: /label= Xaa
            /note= "V or A"

(ix) FEATURE:
        (A) NAME/KEY: Modified-site
        (B) LOCATION: 12
        (D) OTHER INFORMATION: /label= Xaa
            /note= "E or D"

(ix) FEATURE:
        (A) NAME/KEY: Modified-site
        (B) LOCATION: 13
        (D) OTHER INFORMATION: /label= Xaa
            /note= "K or N"

(ix) FEATURE:
        (A) NAME/KEY: Modified-site
        (B) LOCATION: 15
        (D) OTHER INFORMATION: /label= Xaa
            /note= "K or Q"

(ix) FEATURE:
        (A) NAME/KEY: Modified-site
        (B) LOCATION: 20
        (D) OTHER INFORMATION: /label= Xaa
            /note= "H or D"

(ix) FEATURE:
        (A) NAME/KEY: Modified-site
        (B) LOCATION: 21
        (D) OTHER INFORMATION: /label= Xaa
            /note= "N or S"

(ix) FEATURE:
        (A) NAME/KEY: Modified-site
        (B) LOCATION: 23
        (D) OTHER INFORMATION: /label= Xaa
            /note= "A or S"

(ix) FEATURE:
        (A) NAME/KEY: Modified-site
        (B) LOCATION: 37
        (D) OTHER INFORMATION: /label= Xaa
            /note= "I or L"

(ix) FEATURE:
        (A) NAME/KEY: Modified-site
        (B) LOCATION: 62
        (D) OTHER INFORMATION: /label= Xaa
            /note= "I or V"

(ix) FEATURE:
        (A) NAME/KEY: Modified-site
        (B) LOCATION: 65
        (D) OTHER INFORMATION: /label= Xaa
            /note= "D or G"

(ix) FEATURE:
        (A) NAME/KEY: Modified-site
        (B) LOCATION: 66
        (D) OTHER INFORMATION: /label= Xaa
            /note= "S or N"

(xi) SEQUENCE DESCRIPTION: SEQ ID NO:28:

Glu Xaa Leu Gly Asp Ser Xaa Xaa Gly Tyr Lys Xaa Xaa Ser Xaa Phe
1               5                  10                  15

Gln Asp Thr Xaa Xaa Asn Xaa His Tyr Tyr Val Phe Phe Glu Glu Gln
                20                  25                  30

Glu Asp Glu Ile Xaa Gly Phe Gly Gln Glu Leu Lys Asn Pro Gln Glu
            35                  40                  45

Glu Thr Leu Gln Ala Phe Asp Ser His Tyr Asp Tyr Thr Xaa Cys Gly
50                  55                  60
```

```
Xaa Xaa Glu Asp Met Val Cys Thr Pro Lys Ser Asp Glu Phe Asn Pro
65              70                  75                  80

Cys Glu Asp
```

(2) INFORMATION FOR SEQ ID NO:29:

(i) SEQUENCE CHARACTERISTICS:
        (A) LENGTH: 764 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /label= Xaa
            /note= "A or P"

(ix) FEATURE:
        (A) NAME/KEY: Modified-site
        (B) LOCATION: 5
        (D) OTHER INFORMATION: /label= Xaa
            /note= "D or P"

(ix) FEATURE:
        (A) NAME/KEY: Modified-site
        (B) LOCATION: 8
        (D) OTHER INFORMATION: /label= Xaa
            /note= "Q or H"

(ix) FEATURE:
        (A) NAME/KEY: Modified-site
        (B) LOCATION: 10
        (D) OTHER INFORMATION: /label= Xaa
            /note= "V or A"

(ix) FEATURE:
        (A) NAME/KEY: Modified-site
        (B) LOCATION: 14
        (D) OTHER INFORMATION: /label= Xaa
            /note= "D or A"

(ix) FEATURE:
        (A) NAME/KEY: Modified-site
        (B) LOCATION: 18
        (D) OTHER INFORMATION: /label= Xaa
            /note= "D or S"

(ix) FEATURE:
        (A) NAME/KEY: Modified-site
        (B) LOCATION: 22
        (D) OTHER INFORMATION: /label= Xaa
            /note= "M or K"

(ix) FEATURE:
        (A) NAME/KEY: Modified-site
        (B) LOCATION: 25
        (D) OTHER INFORMATION: /label= Xaa
            /note= "S or P"

(ix) FEATURE:
        (A) NAME/KEY: Modified-site
        (B) LOCATION: 35
        (D) OTHER INFORMATION: /label= Xaa
            /note= "E or D"

(ix) FEATURE:
        (A) NAME/KEY: Modified-site
        (B) LOCATION: 45
        (D) OTHER INFORMATION: /label= Xaa
            /note= "Q or H"

(ix) FEATURE:
        (A) NAME/KEY: Modified-site
        (B) LOCATION: 49

```
            (D) OTHER INFORMATION: /label= Xaa
                /note= "S or T"

(ix) FEATURE:
     (A) NAME/KEY: Modified-site
     (B) LOCATION: 59
     (D) OTHER INFORMATION: /label= Xaa
         /note= "L or F"

(ix) FEATURE:
     (A) NAME/KEY: Modified-site
     (B) LOCATION: 63
     (D) OTHER INFORMATION: /label= Xaa
         /note= "H or Q"

(ix) FEATURE:
     (A) NAME/KEY: Modified-site
     (B) LOCATION: 65
     (D) OTHER INFORMATION: /label= Xaa
         /note= "R or K"

(ix) FEATURE:
     (A) NAME/KEY: Modified-site
     (B) LOCATION: 70
     (D) OTHER INFORMATION: /label= Xaa
         /note= "H or R"

(ix) FEATURE:
     (A) NAME/KEY: Modified-site
     (B) LOCATION: 83
     (D) OTHER INFORMATION: /label= Xaa
         /note= "V or L"

(ix) FEATURE:
     (A) NAME/KEY: Modified-site
     (B) LOCATION: 87
     (D) OTHER INFORMATION: /label= Xaa
         /note= "L or A"

(ix) FEATURE:
     (A) NAME/KEY: Modified-site
     (B) LOCATION: 91
     (D) OTHER INFORMATION: /label= Xaa
         /note= "Q or R"

(ix) FEATURE:
     (A) NAME/KEY: Modified-site
     (B) LOCATION: 103
     (D) OTHER INFORMATION: /label= Xaa
         /note= "V or M"

(ix) FEATURE:
     (A) NAME/KEY: Modified-site
     (B) LOCATION: 113
     (D) OTHER INFORMATION: /label= Xaa
         /note= "N or S"

(ix) FEATURE:
     (A) NAME/KEY: Modified-site
     (B) LOCATION: 116
     (D) OTHER INFORMATION: /label= Xaa
         /note= "Y or S"

(ix) FEATURE:
     (A) NAME/KEY: Modified-site
     (B) LOCATION: 139
     (D) OTHER INFORMATION: /label= Xaa
         /note= "K or G"

(ix) FEATURE:
     (A) NAME/KEY: Modified-site
     (B) LOCATION: 140
     (D) OTHER INFORMATION: /label= Xaa
         /note= "M or V"

(ix) FEATURE:
     (A) NAME/KEY: Modified-site
     (B) LOCATION: 144
```

-continued

```
            (D) OTHER INFORMATION: /label= Xaa
                /note= "L or V"

(ix) FEATURE:
            (A) NAME/KEY: Modified-site
            (B) LOCATION: 152
            (D) OTHER INFORMATION: /label= Xaa
                /note= "I or V"

(ix) FEATURE:
            (A) NAME/KEY: Modified-site
            (B) LOCATION: 165
            (D) OTHER INFORMATION: /label= Xaa
                /note= "T or A"

(ix) FEATURE:
            (A) NAME/KEY: Modified-site
            (B) LOCATION: 169
            (D) OTHER INFORMATION: /label= Xaa
                /note= "V or A"

(ix) FEATURE:
            (A) NAME/KEY: Modified-site
            (B) LOCATION: 192
            (D) OTHER INFORMATION: /label= Xaa
                /note= "V or I"

(ix) FEATURE:
            (A) NAME/KEY: Modified-site
            (B) LOCATION: 195
            (D) OTHER INFORMATION: /label= Xaa
                /note= "Y or H"

(ix) FEATURE:
            (A) NAME/KEY: Modified-site
            (B) LOCATION: 214
            (D) OTHER INFORMATION: /label= Xaa
                /note= "T or S"

(ix) FEATURE:
            (A) NAME/KEY: Modified-site
            (B) LOCATION: 215
            (D) OTHER INFORMATION: /label= Xaa
                /note= "V or A"

(ix) FEATURE:
            (A) NAME/KEY: Modified-site
            (B) LOCATION: 229
            (D) OTHER INFORMATION: /label= Xaa
                /note= "S or T"

(ix) FEATURE:
            (A) NAME/KEY: Modified-site
            (B) LOCATION: 235
            (D) OTHER INFORMATION: /label= Xaa
                /note= "Q or Y"

(ix) FEATURE:
            (A) NAME/KEY: Modified-site
            (B) LOCATION: 306
            (D) OTHER INFORMATION: /label= Xaa
                /note= "M or I"

(ix) FEATURE:
            (A) NAME/KEY: Modified-site
            (B) LOCATION: 307
            (D) OTHER INFORMATION: /label= Xaa
                /note= "Q or R"

(ix) FEATURE:
            (A) NAME/KEY: Modified-site
            (B) LOCATION: 317
            (D) OTHER INFORMATION: /label= Xaa
                /note= "A or T"

(ix) FEATURE:
            (A) NAME/KEY: Modified-site
            (B) LOCATION: 320
```

```
          (D) OTHER INFORMATION: /label= Xaa
              /note= "A or T"

(ix) FEATURE:
     (A) NAME/KEY: Modified-site
     (B) LOCATION: 322
     (D) OTHER INFORMATION: /label= Xaa
         /note= "S or G"

(ix) FEATURE:
     (A) NAME/KEY: Modified-site
     (B) LOCATION: 323
     (D) OTHER INFORMATION: /label= Xaa
         /note= "L or F"

(ix) FEATURE:
     (A) NAME/KEY: Modified-site
     (B) LOCATION: 329
     (D) OTHER INFORMATION: /label= Xaa
         /note= "N or Y"

(ix) FEATURE:
     (A) NAME/KEY: Modified-site
     (B) LOCATION: 334
     (D) OTHER INFORMATION: /label= Xaa
         /note= "I or H"

(ix) FEATURE:
     (A) NAME/KEY: Modified-site
     (B) LOCATION: 335
     (D) OTHER INFORMATION: /label= Xaa
         /note= "V or A"

(ix) FEATURE:
     (A) NAME/KEY: Modified-site
     (B) LOCATION: 339
     (D) OTHER INFORMATION: /label= Xaa
         /note= "E or D"

(ix) FEATURE:
     (A) NAME/KEY: Modified-site
     (B) LOCATION: 340
     (D) OTHER INFORMATION: /label= Xaa
         /note= "K or N"

(ix) FEATURE:
     (A) NAME/KEY: Modified-site
     (B) LOCATION: 342
     (D) OTHER INFORMATION: /label= Xaa
         /note= "K or Q"

(ix) FEATURE:
     (A) NAME/KEY: Modified-site
     (B) LOCATION: 347
     (D) OTHER INFORMATION: /label= Xaa
         /note= "H or D"

(ix) FEATURE:
     (A) NAME/KEY: Modified-site
     (B) LOCATION: 348
     (D) OTHER INFORMATION: /label= Xaa
         /note= "N or S"

(ix) FEATURE:
     (A) NAME/KEY: Modified-site
     (B) LOCATION: 350
     (D) OTHER INFORMATION: /label= Xaa
         /note= "A or S"

(ix) FEATURE:
     (A) NAME/KEY: Modified-site
     (B) LOCATION: 364
     (D) OTHER INFORMATION: /label= Xaa
         /note= "I or L"

(ix) FEATURE:
     (A) NAME/KEY: Modified-site
     (B) LOCATION: 389
```

-continued

```
          (D) OTHER INFORMATION: /label= Xaa
              /note= "I or V"

(ix) FEATURE:
     (A) NAME/KEY: Modified-site
     (B) LOCATION: 392
     (D) OTHER INFORMATION: /label= Xaa
         /note= "D or G"

(ix) FEATURE:
     (A) NAME/KEY: Modified-site
     (B) LOCATION: 393
     (D) OTHER INFORMATION: /label= Xaa
         /note= "S or N"

(ix) FEATURE:
     (A) NAME/KEY: Modified-site
     (B) LOCATION: 437
     (D) OTHER INFORMATION: /label= Xaa
         /note= "L or I"

(ix) FEATURE:
     (A) NAME/KEY: Modified-site
     (B) LOCATION: 438
     (D) OTHER INFORMATION: /label= Xaa
         /note= "I or V"

(ix) FEATURE:
     (A) NAME/KEY: Modified-site
     (B) LOCATION: 447
     (D) OTHER INFORMATION: /label= Xaa
         /note= "N or T"

(ix) FEATURE:
     (A) NAME/KEY: Modified-site
     (B) LOCATION: 463
     (D) OTHER INFORMATION: /label= Xaa
         /note= "M or I"

(ix) FEATURE:
     (A) NAME/KEY: Modified-site
     (B) LOCATION: 465
     (D) OTHER INFORMATION: /label= Xaa
         /note= "M or I"

(ix) FEATURE:
     (A) NAME/KEY: Modified-site
     (B) LOCATION: 475
     (D) OTHER INFORMATION: /label= Xaa
         /note= "L or I"

(ix) FEATURE:
     (A) NAME/KEY: Modified-site
     (B) LOCATION: 476
     (D) OTHER INFORMATION: /label= Xaa
         /note= "Y or H"

(ix) FEATURE:
     (A) NAME/KEY: Modified-site
     (B) LOCATION: 478
     (D) OTHER INFORMATION: /label= Xaa
         /note= "H or K"

(ix) FEATURE:
     (A) NAME/KEY: Modified-site
     (B) LOCATION: 480
     (D) OTHER INFORMATION: /label= Xaa
         /note= "E or Q"

(ix) FEATURE:
     (A) NAME/KEY: Modified-site
     (B) LOCATION: 482
     (D) OTHER INFORMATION: /label= Xaa
         /note= "Y or H"

(ix) FEATURE:
     (A) NAME/KEY: Modified-site
     (B) LOCATION: 484
```

```
          (D) OTHER INFORMATION: /label= Xaa
              /note= "H or Y"

(ix) FEATURE:
     (A) NAME/KEY: Modified-site
     (B) LOCATION: 492
     (D) OTHER INFORMATION: /label= Xaa
         /note= "P or A"

(ix) FEATURE:
     (A) NAME/KEY: Modified-site
     (B) LOCATION: 495
     (D) OTHER INFORMATION: /label= Xaa
         /note= "N or D"

(ix) FEATURE:
     (A) NAME/KEY: Modified-site
     (B) LOCATION: 496
     (D) OTHER INFORMATION: /label= Xaa
         /note= "T or A"

(ix) FEATURE:
     (A) NAME/KEY: Modified-site
     (B) LOCATION: 521
     (D) OTHER INFORMATION: /label= Xaa
         /note= "Y or A"

(ix) FEATURE:
     (A) NAME/KEY: Modified-site
     (B) LOCATION: 522
     (D) OTHER INFORMATION: /label= Xaa
         /note= "A or T"

(ix) FEATURE:
     (A) NAME/KEY: Modified-site
     (B) LOCATION: 525
     (D) OTHER INFORMATION: /label= Xaa
         /note= "F or H"

(ix) FEATURE:
     (A) NAME/KEY: Modified-site
     (B) LOCATION: 528
     (D) OTHER INFORMATION: /label= Xaa
         /note= "R or Q"

(ix) FEATURE:
     (A) NAME/KEY: Modified-site
     (B) LOCATION: 531
     (D) OTHER INFORMATION: /label= Xaa
         /note= "R or C"

(ix) FEATURE:
     (A) NAME/KEY: Modified-site
     (B) LOCATION: 533
     (D) OTHER INFORMATION: /label= Xaa
         /note= "I or V"

(ix) FEATURE:
     (A) NAME/KEY: Modified-site
     (B) LOCATION: 534
     (D) OTHER INFORMATION: /label= Xaa
         /note= "R or Q"

(ix) FEATURE:
     (A) NAME/KEY: Modified-site
     (B) LOCATION: 539
     (D) OTHER INFORMATION: /label= Xaa
         /note= "C or Y or A"

(ix) FEATURE:
     (A) NAME/KEY: Modified-site
     (B) LOCATION: 540
     (D) OTHER INFORMATION: /label= Xaa
         /note= "A or S"

(ix) FEATURE:
     (A) NAME/KEY: Modified-site
     (B) LOCATION: 541
```

```
          (D) OTHER INFORMATION: /label= Xaa
              /note= "I or V"

(ix) FEATURE:
     (A) NAME/KEY: Modified-site
     (B) LOCATION: 545
     (D) OTHER INFORMATION: /label= Xaa
         /note= "G or M"

(ix) FEATURE:
     (A) NAME/KEY: Modified-site
     (B) LOCATION: 547
     (D) OTHER INFORMATION: /label= Xaa
         /note= "V or I"

(ix) FEATURE:
     (A) NAME/KEY: Modified-site
     (B) LOCATION: 548
     (D) OTHER INFORMATION: /label= Xaa
         /note= "C or F"

(ix) FEATURE:
     (A) NAME/KEY: Modified-site
     (B) LOCATION: 549
     (D) OTHER INFORMATION: /label= Xaa
         /note= "C or A"

(ix) FEATURE:
     (A) NAME/KEY: Modified-site
     (B) LOCATION: 551
     (D) OTHER INFORMATION: /label= Xaa
         /note= "L or A"

(ix) FEATURE:
     (A) NAME/KEY: Modified-site
     (B) LOCATION: 552
     (D) OTHER INFORMATION: /label= Xaa
         /note= "L or A"

(ix) FEATURE:
     (A) NAME/KEY: Modified-site
     (B) LOCATION: 555
     (D) OTHER INFORMATION: /label= Xaa
         /note= "L or F"

(ix) FEATURE:
     (A) NAME/KEY: Modified-site
     (B) LOCATION: 557
     (D) OTHER INFORMATION: /label= Xaa
         /note= "L or I"

(ix) FEATURE:
     (A) NAME/KEY: Modified-site
     (B) LOCATION: 558
     (D) OTHER INFORMATION: /label= Xaa
         /note= "V or F"

(ix) FEATURE:
     (A) NAME/KEY: Modified-site
     (B) LOCATION: 564
     (D) OTHER INFORMATION: /label= Xaa
         /note= "A or M"

(ix) FEATURE:
     (A) NAME/KEY: Modified-site
     (B) LOCATION: 574
     (D) OTHER INFORMATION: /label= Xaa
         /note= "T or I"

(ix) FEATURE:
     (A) NAME/KEY: Modified-site
     (B) LOCATION: 575
     (D) OTHER INFORMATION: /label= Xaa
         /note= "E or D"

(ix) FEATURE:
     (A) NAME/KEY: Modified-site
     (B) LOCATION: 576
```

```
          (D) OTHER INFORMATION: /label= Xaa
              /note= "T or S"

(ix) FEATURE:
     (A) NAME/KEY: Modified-site
     (B) LOCATION: 579
     (D) OTHER INFORMATION: /label= Xaa
         /note= "A or S"

(ix) FEATURE:
     (A) NAME/KEY: Modified-site
     (B) LOCATION: 580
     (D) OTHER INFORMATION: /label= Xaa
         /note= "L"

(ix) FEATURE:
     (A) NAME/KEY: Modified-site
     (B) LOCATION: 581
     (D) OTHER INFORMATION: /label= Xaa
         /note= "A or Q"

(ix) FEATURE:
     (A) NAME/KEY: Modified-site
     (B) LOCATION: 583
     (D) OTHER INFORMATION: /label= Xaa
         /note= "I or V"

(ix) FEATURE:
     (A) NAME/KEY: Modified-site
     (B) LOCATION: 584
     (D) OTHER INFORMATION: /label= Xaa
         /note= "V or I or M"

(ix) FEATURE:
     (A) NAME/KEY: Modified-site
     (B) LOCATION: 585
     (D) OTHER INFORMATION: /label= Xaa
         /note= "F or L or S"

(ix) FEATURE:
     (A) NAME/KEY: Modified-site
     (B) LOCATION: 586
     (D) OTHER INFORMATION: /label= Xaa
         /note= "V or L"

(ix) FEATURE:
     (A) NAME/KEY: Modified-site
     (B) LOCATION: 588
     (D) OTHER INFORMATION: /label= Xaa
         /note= "T or L or V"

(ix) FEATURE:
     (A) NAME/KEY: Modified-site
     (B) LOCATION: 591
     (D) OTHER INFORMATION: /label= Xaa
         /note= "I or V"

(ix) FEATURE:
     (A) NAME/KEY: Modified-site
     (B) LOCATION: 592
     (D) OTHER INFORMATION: /label= Xaa
         /note= "V or L"

(ix) FEATURE:
     (A) NAME/KEY: Modified-site
     (B) LOCATION: 595
     (D) OTHER INFORMATION: /label= Xaa
         /note= "V or I"

(ix) FEATURE:
     (A) NAME/KEY: Modified-site
     (B) LOCATION: 599
     (D) OTHER INFORMATION: /label= Xaa
         /note= "C or S"

(ix) FEATURE:
     (A) NAME/KEY: Modified-site
     (B) LOCATION: 635
```

```
          (D) OTHER INFORMATION: /label= Xaa
              /note= "I or M"

(ix) FEATURE:
     (A) NAME/KEY: Modified-site
     (B) LOCATION: 648
     (D) OTHER INFORMATION: /label= Xaa
         /note= "I or L"

(ix) FEATURE:
     (A) NAME/KEY: Modified-site
     (B) LOCATION: 649
     (D) OTHER INFORMATION: /label= Xaa
         /note= "L or M"

(ix) FEATURE:
     (A) NAME/KEY: Modified-site
     (B) LOCATION: 657
     (D) OTHER INFORMATION: /label= Xaa
         /note= "S or T"

(ix) FEATURE:
     (A) NAME/KEY: Modified-site
     (B) LOCATION: 712
     (D) OTHER INFORMATION: /label= Xaa
         /note= "P or S"

(ix) FEATURE:
     (A) NAME/KEY: Modified-site
     (B) LOCATION: 717
     (D) OTHER INFORMATION: /label= Xaa
         /note= "T or A"

(ix) FEATURE:
     (A) NAME/KEY: Modified-site
     (B) LOCATION: 718
     (D) OTHER INFORMATION: /label= Xaa
         /note= "D or G"

(ix) FEATURE:
     (A) NAME/KEY: Modified-site
     (B) LOCATION: 721
     (D) OTHER INFORMATION: /label= Xaa
         /note= "V or I"

(ix) FEATURE:
     (A) NAME/KEY: Modified-site
     (B) LOCATION: 726
     (D) OTHER INFORMATION: /label= Xaa
         /note= "H or R"

(ix) FEATURE:
     (A) NAME/KEY: Modified-site
     (B) LOCATION: 731
     (D) OTHER INFORMATION: /label= Xaa
         /note= "G or S"

(ix) FEATURE:
     (A) NAME/KEY: Modified-site
     (B) LOCATION: 733
     (D) OTHER INFORMATION: /label= Xaa
         /note= "H or P"

(ix) FEATURE:
     (A) NAME/KEY: Modified-site
     (B) LOCATION: 736
     (D) OTHER INFORMATION: /label= Xaa
         /note= "E or Q"

(ix) FEATURE:
     (A) NAME/KEY: Modified-site
     (B) LOCATION: 738
     (D) OTHER INFORMATION: /label= Xaa
         /note= "V or E"

(ix) FEATURE:
     (A) NAME/KEY: Modified-site
     (B) LOCATION: 742
```

-continued

```
            (D) OTHER INFORMATION: /label= Xaa
                /note= "I or L"

(ix) FEATURE:
            (A) NAME/KEY: Modified-site
            (B) LOCATION: 750
            (D) OTHER INFORMATION: /label= Xaa
                /note= "K or N"

(ix) FEATURE:
            (A) NAME/KEY: Modified-site
            (B) LOCATION: 757
            (D) OTHER INFORMATION: /label= Xaa
                /note= "E or K"

(ix) FEATURE:
            (A) NAME/KEY: Modified-site
            (B) LOCATION: 760
            (D) OTHER INFORMATION: /label= Xaa
                /note= "M or N"

(xi) SEQUENCE DESCRIPTION: SEQ ID NO:29:

Met Arg Pro Xaa Xaa Leu Leu Xaa Leu Xaa Leu Leu Leu Xaa Leu Pro
 1               5                  10                  15

Arg Xaa Leu Gly Gly Xaa Gly Cys Xaa Ser Pro Pro Cys Glu Cys His
            20                  25                  30

Gln Glu Xaa Asp Phe Arg Val Thr Cys Lys Asp Ile Xaa Arg Ile Pro
        35                  40                  45

Xaa Leu Pro Pro Ser Thr Gln Thr Leu Lys Xaa Ile Glu Thr Xaa Leu
50                  55                  60

Xaa Thr Ile Pro Ser Xaa Ala Phe Ser Asn Leu Pro Asn Ile Ser Arg
65                  70                  75                  80

Ile Tyr Xaa Ser Ile Asp Xaa Thr Leu Gln Xaa Leu Glu Ser His Ser
                85                  90                  95

Phe Tyr Asn Leu Ser Lys Xaa Thr His Ile Glu Ile Arg Asn Thr Arg
            100                 105                 110

Xaa Leu Thr Xaa Ile Asp Pro Asp Ala Leu Lys Glu Leu Pro Leu Leu
        115                 120                 125

Lys Phe Leu Gly Ile Phe Asn Thr Gly Leu Xaa Xaa Phe Pro Asp Xaa
130                 135                 140

Thr Lys Val Tyr Ser Thr Asp Xaa Phe Phe Ile Leu Glu Ile Thr Asp
145                 150                 155                 160

Asn Pro Tyr Met Xaa Ser Ile Pro Xaa Asn Ala Phe Gln Gly Leu Cys
                165                 170                 175

Asn Glu Thr Leu Thr Leu Lys Leu Tyr Asn Asn Gly Phe Thr Ser Xaa
            180                 185                 190

Gln Gly Xaa Ala Phe Asn Gly Thr Lys Leu Asp Ala Val Tyr Leu Asn
        195                 200                 205

Lys Asn Lys Tyr Leu Xaa Xaa Ile Asp Lys Asp Ala Phe Gly Gly Val
210                 215                 220

Tyr Ser Gly Pro Xaa Leu Leu Asp Val Ser Xaa Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
290                 295                 300
```

-continued

```
Ser Xaa Xaa Ser Leu Arg Gln Arg Lys Ser Val Asn Xaa Leu Asn Xaa
305                 310                 315                 320

Pro Xaa Xaa Gln Glu Tyr Glu Xaa Leu Gly Asp Ser Xaa Xaa Gly
            325                 330                 335

Tyr Lys Xaa Xaa Ser Xaa Phe Gln Asp Thr Xaa Xaa Asn Xaa His Tyr
                340                 345                 350

Tyr Val Phe Phe Glu Glu Gln Gly Asp Glu Ile Xaa Gly Phe Gly Gln
            355                 360                 365

Glu Leu Lys Asn Pro Gln Glu Glu Thr Leu Gln Ala Phe Asp Ser His
        370                 375                 380

Tyr Asp Tyr Thr Xaa Cys Gly Xaa Xaa Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Xaa Xaa Leu Leu Thr Ser His Tyr Lys Leu Xaa Val
            435                 440                 445

Pro Arg Phe Leu Met Cys Asn Leu Ala Phe Ala Asp Phe Cys Xaa Gly
        450                 455                 460

Xaa Tyr Leu Leu Leu Ile Ala Ser Val Asp Xaa Xaa Thr Xaa Ser Xaa
465                 470                 475                 480

Tyr Xaa Asn Xaa Ala Ile Asp Trp Gln Thr Gly Xaa Gly Cys Xaa Xaa
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Xaa Xaa Ile Thr Xaa Ala Met Xaa
            515                 520                 525

Leu Asp Xaa Lys Xaa Xaa Leu Arg His Ala Xaa Xaa Xaa Met Val Gly
        530                 535                 540

Xaa Trp Xaa Xaa Xaa Phe Xaa Xaa Ala Leu Xaa Pro Xaa Xaa Gly Ile
545                 550                 555                 560

Ser Ser Tyr Xaa Lys Val Ser Ile Cys Leu Pro Met Asp Xaa Xaa Xaa
                565                 570                 575

Pro Leu Xaa Xaa Xaa Tyr Xaa Xaa Xaa Xaa Leu Xaa Leu Asn Xaa Xaa
            580                 585                 590

Ala Phe Xaa Ile Val Cys Xaa Cys Tyr Val Lys Ile Tyr Ile Thr Val
            595                 600                 605

Arg Asn Pro Gln Tyr Asn Pro Gly Asp Lys Asp Thr Lys Ile Ala Lys
        610                 615                 620

Arg Met Ala Val Leu Ile Phe Thr Asp Phe Xaa Cys Met Ala Pro Ile
625                 630                 635                 640

Ser Phe Tyr Ala Leu Ser Ala Xaa Xaa Asn Lys Pro Leu Ile Thr Val
                645                 650                 655

Xaa Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
            690                 695                 700

Ala Tyr Arg Gly Gln Arg Val Xaa Pro Lys Asn Ser Xaa Xaa Ile Gln
705                 710                 715                 720
```

```
Xaa Gln Lys Val Thr Xaa Asp Met Arg Gln Xaa Leu Xaa Asn Met Xaa
            725                 730                 735

Asp Xaa Tyr Glu Leu Xaa Glu Asn Ser His Leu Thr Pro Xaa Lys Gln
        740                 745                 750

Gly Gln Ile Ser Xaa Glu Tyr Xaa Gln Thr Val Leu
        755                 760
```

(2) INFORMATION FOR SEQ ID NO:30:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

TAGATCTAGA CYTGKCSNKB GCYGAYMT                            28

(2) INFORMATION FOR SEQ ID NO:31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TAGATCTAGA CTTGTCCNGCG CTGAGAT                            28

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

TAGATCTAGA CCTGGCGNTGG CCGATCT                            28

(2) INFORMATION FOR SEQ ID NO:33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

ACTTTAAGCT TGCARTARMM SANRGGRTT                           29

(2) INFORMATION FOR SEQ ID NO:34:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

ACTTTAAGCT TGCAATAAAA GANGGGGTT 29

(2) INFORMATION FOR SEQ ID NO:35:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Cys Asp Ala Ala Gly Phe Phe Thr Val Phe Ala Ser Glu Leu Ser Val
1               5                  10                 15
Tyr Thr Leu Thr Ala Ile Thr Leu Glu Arg Trp His Thr Ile Thr His
            20                  25                 30
Ala Met Gln Leu Asp Cys Lys Val Gln Leu Arg His Ala Ala Ser Val
        35                  40                  45
Met Val Met Gly Trp Ile Phe Ala Phe
    50                  55
```

(2) INFORMATION FOR SEQ ID NO:36:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Cys Asp Leu Trp Leu Ala Leu Asp Tyr Val Val Ser Asn Ala Ser Val
1               5                  10                 15
Met Asn Leu Leu Ile Ile Ser Phe Asp Arg Tyr Phe Cys Val Thr Lys
            20                  25                 30
Pro Leu Thr Tyr Pro Val Lys Arg Thr Thr Lys Met Ala Gly Met Met
        35                  40                  45
Ile Ala Ala Ala Trp Val Leu Ser Phe
    50                  55
```

(2) INFORMATION FOR SEQ ID NO:37:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Cys Asp Leu Trp Leu Ala Leu Asp Tyr Val Val Ser Asn Ala Ser Val
1               5                  10                 15
Met Asn Leu Leu Ile Ile Ser Phe Asp Arg Tyr Phe Cys Val Thr Lys
            20                  25                 30
Pro Leu Thr Tyr Pro Ala Arg Arg Thr Thr Lys Met Ala Gly Leu Met
        35                  40                  45
Ile Ala Ala Ala Trp Val Leu Ser Phe
    50                  55
```

(2) INFORMATION FOR SEQ ID NO:38:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Cys Asp Leu Trp Leu Ala Leu Asp Tyr Val Ala Ser Asn Ala Ser Val
1               5                   10                  15

Met Asn Leu Leu Leu Ile Ser Phe Asp Arg Tyr Phe Ser Val Thr Arg
                20                  25                  30

Pro Leu Ser Tyr Arg Ala Lys Arg Thr Pro Arg Arg Ala Ala Leu Met
            35                  40                  45

Ile Gly Leu Ala Trp Leu Val Ser Phe
    50                  55

(2) INFORMATION FOR SEQ ID NO:39:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Cys Asp Leu Trp Leu Ala Ile Asp Tyr Val Ala Ser Asn Ala Ser Val
1               5                   10                  15

Met Asn Leu Leu Val Ile Ser Phe Asp Arg Tyr Phe Ser Ile Thr Arg
                20                  25                  30

Pro Leu Thr Tyr Arg Ala Lys Arg Thr Thr Lys Arg Ala Gly Val Met
            35                  40                  45

Ile Gly Leu Ala Trp Val Ile Ser Phe
    50                  55

(2) INFORMATION FOR SEQ ID NO:40:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Cys Asp Ile Trp Ala Ala Val Asp Val Leu Cys Cys Thr Ala Ser Ile
1               5                   10                  15

Leu Ser Leu Cys Ala Ile Ser Ile Asp Arg Tyr Ile Gly Val Arg Tyr
                20                  25                  30

Ser Leu Gln Tyr Pro Thr Leu Val Thr Arg Arg Lys Ala Ile Leu Ala
            35                  40                  45

Leu Leu Ser Val Trp Val Leu Ser Thr
    50                  55

(2) INFORMATION FOR SEQ ID NO:41:

(i) SEQUENCE CHARACTERISTICS:
      (A) LENGTH: 58 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:41:

```
Cys Asp Ile Phe Val Thr Leu Asp Val Met Met Cys Thr Ala Ser Ile
1               5                   10                  15

Leu Asn Leu Cys Ala Ile Ser Ile Asp Arg Tyr Thr Ala Val Ala Met
            20                  25                  30

Pro Met Leu Tyr Asn Thr Arg Tyr Ser Ser Lys Arg Arg Val Thr Val
                35                  40                  45

Met Ile Ala Ile Val Trp Val Leu Ser Phe
    50                  55
```

(2) INFORMATION FOR SEQ ID NO:42:

(i) SEQUENCE CHARACTERISTICS:
      (A) LENGTH: 57 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:42:

```
Cys Glu Leu Trp Thr Ser Val Asp Val Leu Cys Val Thr Ala Ser Ile
1               5                   10                  15

Glu Thr Leu Cys Val Ile Ala Leu Asp Arg Tyr Leu Ala Ile Thr Ser
            20                  25                  30

Pro Phe Arg Tyr Gln Ser Leu Leu Thr Arg Ala Arg Ala Arg Gly Leu
                35                  40                  45

Val Cys Thr Val Trp Ala Ile Ser Ala
    50                  55
```

(2) INFORMATION FOR SEQ ID NO:43:

(i) SEQUENCE CHARACTERISTICS:
      (A) LENGTH: 57 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:43:

```
Cys Glu Phe Trp Thr Ser Ile Asp Val Leu Cys Val Thr Ala Ser Ile
1               5                   10                  15

Glu Thr Leu Cys Val Ile Ala Val Asp Arg Tyr Phe Ala Ile Thr Ser
            20                  25                  30

Pro Phe Lys Tyr Gln Ser Leu Leu Thr Lys Asn Lys Ala Arg Val Ile
                35                  40                  45

Ile Leu Met Val Trp Ile Val Ser Gly
    50                  55
```

(2) INFORMATION FOR SEQ ID NO:44:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Cys Glu Phe Trp Thr Ser Ile Asp Val Leu Cys Val Thr Ala Ser Ile
1               5                  10                  15

Glu Thr Leu Cys Val Ile Ala Val Asp Arg Tyr Ile Ala Ile Thr Ser
            20                  25                  30

Pro Phe Lys Tyr Gln Ser Leu Leu Thr Lys Asn Lys Ala Arg Met Val
        35                  40                  45

Ile Leu Met Val Trp Ile Val Ser Gly
    50                  55
```

(2) INFORMATION FOR SEQ ID NO:45:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Cys Asp Ile Trp Leu Ser Ser Asp Ile Thr Cys Cys Thr Ala Ser Ile
1               5                  10                  15

Leu His Leu Cys Val Ile Ala Leu Asp Arg Tyr Trp Ala Ile Thr Asp
            20                  25                  30

Ala Leu Glu Tyr Ser Lys Arg Arg Thr Ala Gly Arg Ala Ala Val Met
        35                  40                  45

Ile Ala Thr Val Trp Val Ile Ser Ile
    50                  55
```

(2) INFORMATION FOR SEQ ID NO:46:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Cys Glu Ile Tyr Leu Ala Leu Asp Val Leu Phe Cys Thr Ser Ser Ile
1               5                  10                  15

Val His Leu Cys Ala Ile Ser Leu Asp Arg Tyr Trp Ser Ile Thr Gln
            20                  25                  30

Ala Ile Glu Tyr Asn Leu Lys Arg Thr Arg Arg Ile Lys Ala Ile
        35                  40                  45

Ile Thr Cys Trp Val Ile Ser Ala
    50                  55
```

(2) INFORMATION FOR SEQ ID NO:47:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

Cys Asp Leu Phe Ile Ala Leu Asp Val Leu Cys Cys Thr Ser Ser Ile
1               5                   10                  15

Leu His Leu Cys Ala Ile Ala Leu Asp Arg Tyr Trp Ala Ile Thr Asp
            20                  25                  30

Pro Ile Asp Tyr Val Asn Lys Arg Thr Pro Arg Pro Arg Ala Leu Ile
            35                  40                  45

Ser Leu Thr Trp Leu Ile Gly Phe
            50              55

(2) INFORMATION FOR SEQ ID NO:48:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

Cys Pro Val Trp Ile Ser Leu Asp Val Leu Phe Ser Thr Ala Ser Ile
1               5                   10                  15

Met His Leu Cys Ala Ile Ser Leu Asp Arg Tyr Val Ala Ile Arg Asn
            20                  25                  30

Pro Ile Glu His Ser Arg Phe Asn Ser Arg Thr Lys Ala Ile Met Lys
            35                  40                  45

Ile Ala Ile Val Trp Ala Ile Ser Ile
            50              55

(2) INFORMATION FOR SEQ ID NO:49:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

Cys Ala Ile Trp Ile Tyr Leu Asp Val Leu Phe Ser Thr Ala Ser Ile
1               5                   10                  15

Met His Leu Cys Ala Ile Ser Leu Asp Arg Tyr Val Ala Ile Gln Asn
            20                  25                  30

Pro Ile His His Ser Arg Phe Asn Ser Arg Thr Lys Ala Phe Leu Lys
            35                  40                  45

Ile Ile Ala Val Trp Thr Ile Ser Val
            50              55

(2) INFORMATION FOR SEQ ID NO:50:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Cys Leu Phe Phe Ala Cys Phe Val Leu Val Leu Thr Gln Ser Ser Ile
  1               5                  10                  15

Phe Ser Leu Leu Ala Ile Ala Ile Asp Arg Tyr Ile Ala Ile Arg Ile
             20                  25                  30

Pro Leu Arg Tyr Asn Gly Leu Val Thr Gly Thr Arg Ala Lys Gly Ile
             35                  40                  45

Ile Ala Val Cys Trp Val Leu Ser Phe
             50                  55
```

(2) INFORMATION FOR SEQ ID NO:51:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Cys Leu Met Val Ala Cys Pro Val Leu Ile Leu Thr Gln Ser Ser Ile
  1               5                  10                  15

Leu Ala Leu Leu Ala Ile Ala Val Asp Arg Tyr Leu Arg Val Lys Ile
             20                  25                  30

Pro Leu Arg Tyr Lys Thr Val Val Thr Pro Arg Arg Ala Ala Val Ala
             35                  40                  45

Ile Ala Gly Cys Trp Ile Leu Ser Phe
             50                  55
```

(2) INFORMATION FOR SEQ ID NO:52:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Cys Tyr Phe Gln Asn Leu Phe Pro Ile Thr Ala Met Phe Val Ser Ile
  1               5                  10                  15

Tyr Ser Met Thr Ala Ile Ala Ala Asp Arg Tyr Met Ala Ile Val His
             20                  25                  30

Pro Phe Gln Pro Arg Leu Ser Ala Pro Gly Thr Arg Ala Val Ile Ala
             35                  40                  45

Gly Ile Trp Leu Val Ala Leu
             50                  55
```

-continued (2) INFORMATION FOR SEQ ID NO:53:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Cys Lys Ile Thr His Leu Ile Phe Ser Ile Asn Leu Phe Gly Ser Ile
1               5                   10                  15

Phe Phe Leu Thr Cys Met Ser Val Asp Arg Tyr Leu Ser Ile Thr Tyr
            20                  25                  30

Phe Ala Ser Thr Ser Ser Arg Arg Lys Lys Val Val Arg Arg Ala Val
            35                  40                  45

Cys Val Leu Val Trp Leu Leu Ala Phe
50                  55
```

(2) INFORMATION FOR SEQ ID NO:54:

(i) SEQUENCE CHARACTERISTICS:
        (A) LENGTH: 764 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

```
Met Arg Pro Pro Pro Leu Leu His Leu Ala Leu Leu Ala Leu Pro
1               5                   10                  15

Arg Ser Leu Gly Gly Lys Gly Cys Pro Ser Pro Cys Glu Cys His
            20                  25                  30

Gln Glu Asp Asp Phe Arg Val Thr Cys Lys Asp Ile His Arg Ile Pro
            35                  40                  45

Thr Leu Pro Pro Ser Thr Gln Thr Leu Lys Phe Ile Glu Thr Gln Leu
            50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Arg Leu Glu Ser His Ser
                85                  90                  95

Phe Tyr Asn Leu Ser Lys Met Thr His Ile Glu Ile Arg Asn Thr Arg
                100                 105                 110

Ser Leu Thr Ser Ile Asp Pro Asp Ala Leu Lys Glu Leu Pro Leu Leu
            115                 120                 125

Lys Phe Leu Gly Ile Phe Asn Thr Gly Leu Gly Val Phe Pro Asp Val
130                 135                 140

Thr Lys Val Tyr Ser Thr Asp Val Phe Phe Ile Leu Glu Ile Thr Asp
145                 150                 155                 160

Asn Pro Tyr Met Ala Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
                180                 185                 190

Gln Gly His Ala Phe Asn Gly Thr Lys Leu Asp Ala Val Tyr Leu Asn
            195                 200                 205

Lys Asn Lys Tyr Leu Ser Ala Ile Asp Lys Asp Ala Phe Gly Gly Val
            210                 215                 220
```

-continued

```
Tyr Ser Gly Pro Thr Leu Leu Asp Val Ser Tyr Thr Ser Val Thr Ala
225                 230                 235                 240

Leu Pro Ser Lys Gly Leu Glu His Leu Lys Glu Leu Ile Ala Arg Asn
            245                 250                 255

Thr Trp Thr Leu Lys Lys Leu Pro Leu Ser Leu Ser Phe Leu His Leu
                260                 265                 270

Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
290                 295                 300

Ser Ile Arg Ser Leu Arg Gln Arg Lys Ser Val Asn Thr Leu Asn Gly
305                 310                 315                 320

Pro Phe Asp Gln Glu Tyr Glu Glu Tyr Leu Gly Asp Ser His Ala Gly
                325                 330                 335

Tyr Lys Asp Asn Ser Gln Phe Gln Asp Thr Asp Ser Asn Ser His Tyr
                340                 345                 350

Tyr Val Phe Phe Glu Glu Gln Glu Asp Glu Ile Leu Gly Phe Gly Gln
                355                 360                 365

Glu Leu Lys Asn Pro Gln Glu Glu Thr Leu Gln Ala Phe Asp Ser His
370                 375                 380

Tyr Asp Tyr Thr Val Cys Gly Gly Asn Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
                420                 425                 430

Val Phe Val Leu Ile Val Leu Leu Thr Ser His Tyr Lys Leu Thr Val
            435                 440                 445

Pro Arg Phe Leu Met Cys Asn Leu Ala Phe Ala Asp Phe Cys Met Gly
            450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
                500                 505                 510

Thr Val Ile Thr Leu Glu Arg Trp Tyr Ala Ile Thr Phe Ala Met Arg
            515                 520                 525

Leu Asp Arg Lys Ile Arg Leu Arg His Ala Tyr Ala Ile Met Val Gly
            530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Leu Asn Ile Val
                580                 585                 590

Ala Phe Ile Ile Val Cys Ser Cys Tyr Val Lys Ile Tyr Ile Thr Val
            595                 600                 605

Arg Asn Pro Gln Tyr Asn Pro Gly Asp Lys Asp Thr Lys Ile Ala Lys
            610                 615                 620

Arg Met Ala Val Leu Ile Phe Thr Asp Phe Met Cys Met Ala Pro Ile
625                 630                 635                 640
```

```
Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
        690                 695                 700

Ala Tyr Arg Gly Gln Arg Val Ser Pro Lys Asn Ser Ala Gly Ile Gln
705                 710                 715                 720

Ile Gln Lys Val Thr Arg Asp Met Arg Gln Ser Leu Pro Asn Met Gln
                725                 730                 735

Asp Glu Tyr Glu Leu Leu Glu Asn Ser His Leu Thr Pro Asn Lys Gln
                740                 745                 750

Gly Gln Ile Ser Lys Glu Tyr Asn Gln Thr Val Leu
            755                 760

(2) INFORMATION FOR SEQ ID NO:55:

(i) SEQUENCE CHARACTERISTICS:
        (A) LENGTH: 795 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

Arg Ala Thr His Cys Gly Met Gly Arg Arg Val Pro Ala Leu Arg Gln
1               5                   10                  15

Leu Leu Val Leu Ala Val Leu Leu Lys Pro Ser Gln Leu Gln Ser
            20                  25                  30

Arg Glu Leu Ser Gly Ser Arg Cys Pro Glu Pro Cys Asp Cys Ala Pro
            35                  40                  45

Asp Gly Ala Leu Arg Ala Thr His Cys Gly Arg Cys Pro Gly Pro Arg
    50                  55                  60

Ala Gly Leu Ala Arg Leu Ser Leu Thr Tyr Leu Pro Val Lys Val Ile
65                  70                  75                  80

Pro Ser Gln Ala Phe Arg Gly Leu Asn Glu Val Val Lys Ile Glu Ile
            85                  90                  95

Ser Gln Ser Asp Ser Leu Glu Arg Ala Thr His Cys Gly Arg Ile Glu
            100                 105                 110

Ala Asn Ala Phe Asp Asn Leu Leu Asn Leu Ser Glu Leu Leu Ile Gln
            115                 120                 125

Asn Thr Lys Asn Leu Leu Tyr Ile Glu Pro Gly Ala Phe Thr Asn Leu
    130                 135                 140

Pro Arg Leu Lys Tyr Leu Ser Ile Cys Asn Thr Gly Ile Arg Thr Arg
145                 150                 155                 160

Ala Thr His Cys Gly Leu Pro Asp Val Thr Lys Ile Ser Ser Ser Glu
            165                 170                 175

Phe Asn Phe Ile Leu Glu Ile Cys Asp Asn Leu His Ile Thr Thr Ile
            180                 185                 190

Pro Gly Asn Ala Phe Gln Gly Met Asn Asn Glu Ser Val Thr Leu Lys
            195                 200                 205

Leu Tyr Gly Asn Gly Phe Glu Arg Ala Thr His Cys Gly Glu Val Gln
    210                 215                 220
```

```
Ser His Ala Phe Asn Gly Thr Thr Leu Ile Ser Leu Glu Leu Lys Glu
225                 230                 235                 240

Asn Ile Tyr Leu Glu Lys Met His Ser Gly Ala Phe Gln Gly Ala Thr
                245                 250                 255

Gly Pro Ser Ile Leu Asp Ile Ser Ser Thr Lys Leu Gln Ala Arg Ala
                260                 265                 270

Thr His Cys Gly Leu Pro Ser His Gly Leu Glu Ser Ile Gln Thr Leu
            275                 280                 285

Ile Ala Leu Ser Ser Tyr Ser Leu Lys Thr Leu Pro Ser Lys Glu Lys
            290                 295                 300

Phe Thr Ser Leu Leu Val Ala Thr Leu Thr Tyr Pro Ser His Cys Cys
305                 310                 315                 320

Ala Phe Arg Asn Leu Pro Arg Ala Thr His Cys Gly Lys Lys Glu Gln
                325                 330                 335

Asn Phe Ser Phe Ser Ile Phe Glu Asn Phe Ser Lys Gln Cys Glu Ser
                340                 345                 350

Thr Val Arg Lys Ala Asp Asn Glu Thr Leu Tyr Ser Ala Ile Phe Glu
            355                 360                 365

Glu Asn Glu Leu Ser Gly Trp Asp Arg Ala Thr His Cys Gly Tyr Asp
    370                 375                 380

Tyr Gly Arg Ala Thr His Cys Gly Phe Ser Pro Lys Thr Leu Gln Cys
385                 390                 395                 400

Ala Pro Glu Pro Asp Ala Phe Asn Pro Cys Glu Asp Ile Met Gly Tyr
                405                 410                 415

Ala Phe Leu Arg Val Leu Ile Trp Leu Ile Asn Ile Leu Ala Ile Phe
                420                 425                 430

Gly Asn Leu Thr Val Leu Phe Val Arg Ala Thr His Cys Gly Leu Leu
            435                 440                 445

Thr Ser Arg Tyr Lys Leu Thr Val Pro Arg Phe Leu Met Cys Asn Leu
450                 455                 460

Ser Phe Ala Asp Phe Cys Met Gly Leu Tyr Leu Leu Leu Ile Ala Ser
465                 470                 475                 480

Val Asp Ser Gln Thr Lys Gly Gln Tyr Tyr Asn His Ala Ile Asp Trp
                485                 490                 495

Arg Ala Thr His Cys Gly Gln Thr Gly Ser Gly Cys Gly Ala Ala Gly
            500                 505                 510

Phe Phe Thr Val Phe Ala Ser Glu Leu Ser Val Tyr Thr Leu Thr Val
            515                 520                 525

Ile Thr Leu Glu Arg Trp His Thr Ile Thr Tyr Ala Val Gln Leu Asp
    530                 535                 540

Gln Lys Leu Arg Leu Arg His Ala Arg Ala Thr His Cys Gly Ile Pro
545                 550                 555                 560

Ile Met Leu Gly Gly Trp Leu Phe Ser Thr Leu Ile Ala Thr Met Pro
                565                 570                 575

Leu Val Gly Ile Ser Asn Tyr Met Lys Val Ser Ile Cys Leu Pro Met
            580                 585                 590

Asp Val Glu Ser Thr Leu Ser Gln Val Tyr Ile Leu Ser Ile Leu Ile
            595                 600                 605

Arg Ala Thr His Cys Gly Leu Asn Val Val Ala Phe Val Val Ile Cys
    610                 615                 620

Ala Cys Tyr Ile Arg Ile Tyr Phe Ala Val Gln Asn Pro Glu Leu Thr
625                 630                 635                 640
```

```
Ala Pro Asn Lys Asp Thr Lys Ile Ala Lys Lys Met Ala Ile Leu Ile
            645                 650                 655

Phe Thr Asp Phe Thr Cys Met Ala Arg Ala Thr His Cys Gly Pro Ile
            660                 665                 670

Ser Phe Phe Ala Ile Ser Ala Ala Phe Lys Val Pro Leu Ile Thr Val
            675                 680                 685

Thr Asn Ser Lys Ile Leu Leu Val Leu Phe Tyr Pro Val Asn Ser Cys
            690                 695                 700

Ala Asn Pro Phe Leu Tyr Ala Ile Phe Thr Lys Ala Phe Gln Arg Asp
705                 710                 715                 720

Arg Ala Thr His Cys Gly Phe Leu Leu Leu Ser Arg Phe Gly Cys
                725                 730                 735

Cys Lys Arg Arg Ala Glu Leu Tyr Arg Arg Lys Glu Phe Ser Ala Tyr
            740                 745                 750

Thr Ser Asn Cys Lys Asn Gly Phe Pro Gly Ala Ser Lys Pro Ser Gln
            755                 760                 765

Ala Thr Leu Lys Leu Ser Thr Val Arg Ala Thr His Cys Gly His Cys
            770                 775                 780

Gln Gln Pro Ile Pro Pro Arg Ala Leu Thr His
785                 790                 795

(2) INFORMATION FOR SEQ ID NO:56:

(i) SEQUENCE CHARACTERISTICS:
        (A) LENGTH: 792 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

Pro Ile Gly His Cys Gly Met Arg Arg Arg Ser Leu Ala Leu Arg Leu
1                   5                   10                  15

Leu Leu Ala Leu Leu Leu Leu Pro Pro Pro Leu Pro Gln Thr Leu Leu
                20                  25                  30

Gly Ala Pro Cys Pro Glu Pro Cys Ser Cys Arg Pro Asp Gly Ala Leu
            35                  40                  45

Pro Ile Gly His Cys Gly Arg Cys Pro Gly Pro Arg Ala Gly Leu Ser
        50                  55                  60

Arg Leu Ser Leu Thr Tyr Leu Pro Ile Val Ile Pro Ser Gln Ala
65                  70                  75                  80

Phe Arg Gly Leu Asn Glu Val Val Lys Ile Glu Ile Ser Gln Ser Asp
                85                  90                  95

Ser Leu Glu Pro Ile Gly His Cys Gly Lys Ile Glu Ala Asn Ala Phe
            100                 105                 110

Asp Asn Leu Leu Asn Leu Ser Glu Ile Leu Ile Gln Asn Thr Lys Asn
            115                 120                 125

Leu Val Tyr Ile Glu Pro Gly Ala Phe Thr Asn Leu Pro Arg Leu Lys
            130                 135                 140

Tyr Leu Ser Ile Cys Asn Thr Gly Ile Arg Lys Pro Ile Gly His Cys
145                 150                 155                 160

Gly Leu Pro Asp Val Thr Lys Ile Phe Ser Ser Glu Phe Asn Phe Ile
                165                 170                 175

Leu Glu Ile Cys Asp Asn Leu His Ile Thr Thr Val Pro Ala Asn Ala
            180                 185                 190
```

-continued

```
Phe Gln Gly Met Asn Asn Glu Ser Ile Thr Leu Lys Leu Tyr Gly Asn
        195                 200                 205

Gly Phe Glu Pro Ile Gly His Cys Gly Glu Ile Gln Ser His Ala Phe
        210                 215                 220

Asn Gly Thr Leu Leu Ile Ser Leu Glu Leu Lys Glu Asn Ala His Leu
225                 230                 235                 240

Lys Lys Met His Asn Asp Ala Phe Arg Gly Arg Gly Pro Ser Ile
                245                 250                 255

Leu Asp Ile Ser Ser Thr Lys Leu Gln Ala Pro Ile Gly His Cys Gly
                260                 265                 270

Leu Pro Ser Tyr Gly Leu Glu Ser Ile Gln Thr Leu Ile Ala Thr Ser
            275                 280                 285

Ser Tyr Ser Leu Lys Lys Leu Pro Ser Arg Glu Lys Phe Thr Asn Leu
        290                 295                 300

Leu Asp Ala Thr Leu Thr Tyr Pro Ser His Cys Cys Ala Phe Arg Asn
305                 310                 315                 320

Leu Pro Pro Ile Gly His Cys Gly Thr Lys Glu Gln Asn Phe Ser Phe
                325                 330                 335

Ser Ile Phe Lys Asn Phe Ser Lys Gln Cys Glu Ser Thr Ala Arg Arg
                340                 345                 350

Pro Asn Asn Glu Thr Leu Tyr Ser Ala Ile Phe Ala Glu Ser Glu Leu
            355                 360                 365

Ser Asp Trp Asp Pro Ile Gly His Cys Gly Tyr Asp Tyr Gly Pro Ile
        370                 375                 380

Gly His Cys Gly Phe Cys Ser Pro Lys Thr Leu Gln Cys Ala Pro Glu
385                 390                 395                 400

Pro Asp Ala Phe Asn Pro Cys Glu Asp Ile Met Gly Tyr Asp Phe Leu
                405                 410                 415

Arg Val Leu Ile Trp Leu Ile Asn Ile Leu Ala Ile Met Gly Asn Val
                420                 425                 430

Thr Val Leu Phe Ala Pro Ile Gly His Cys Gly Leu Leu Thr Ser His
            435                 440                 445

Tyr Lys Leu Thr Val Pro Arg Phe Leu Met Cys Asn Leu Ser Phe Ala
        450                 455                 460

Asp Phe Cys Met Gly Leu Tyr Leu Leu Leu Ile Ala Ser Val Asp Ala
465                 470                 475                 480

Gln Thr Lys Gly Gln Tyr Tyr Asn His Ala Ile Asp Trp Pro Ile Gly
                485                 490                 495

His Cys Gly Gln Thr Gly Asn Gly Cys Ser Val Ala Gly Phe Phe Thr
            500                 505                 510

Val Phe Ala Ser Glu Leu Ser Val Tyr Thr Leu Thr Val Ile Thr Leu
        515                 520                 525

Glu Arg Trp His Thr Ile Thr Tyr Ala Ile Gln Leu Asp Gln Lys Leu
        530                 535                 540

Arg Leu Arg His Ala Pro Ile Gly His Cys Gly Ile Pro Ile Met Leu
545                 550                 555                 560

Gly Gly Trp Leu Phe Ser Thr Leu Ile Ala Met Leu Pro Leu Val Gly
                565                 570                 575

Val Ser Ser Tyr Met Lys Val Ser Ile Cys Leu Pro Met Asp Val Glu
            580                 585                 590

Thr Thr Leu Ser Gln Val Tyr Ile Leu Thr Ile Leu Ile Pro Ile Gly
        595                 600                 605
```

```
His Cys Gly Leu Asn Val Val Ala Phe Ile Ile Ile Cys Ala Cys Tyr
    610                 615                 620
Ile Lys Ile Tyr Phe Ala Val Gln Asn Pro Glu Leu Met Ala Thr Asn
625                 630                 635                 640
Lys Asp Thr Lys Ile Ala Lys Lys Met Ala Val Leu Ile Phe Thr Asp
                645                 650                 655
Phe Thr Cys Met Ala Pro Ile Gly His Cys Gly Pro Ile Ser Phe Phe
            660                 665                 670
Ala Ile Ser Ala Ala Leu Lys Val Pro Leu Ile Thr Val Thr Asn Ser
                675                 680                 685
Lys Val Leu Leu Val Leu Phe Tyr Pro Val Asn Ser Cys Ala Asn Pro
690                 695                 700
Phe Leu Tyr Ala Ile Phe Thr Lys Ala Phe Arg Arg Asp Pro Ile Gly
705                 710                 715                 720
His Cys Gly Phe Phe Leu Leu Leu Ser Lys Ser Gly Cys Cys Lys His
                725                 730                 735
Gln Ala Glu Leu Tyr Arg Arg Lys Asp Phe Ser Ala Tyr Cys Lys Asn
                740                 745                 750
Gly Phe Thr Gly Ser Asn Lys Pro Ser Arg Ser Thr Leu Lys Leu Thr
            755                 760                 765
Thr Leu Pro Ile Gly His Cys Gly Gln Cys Gln Tyr Ser Thr Val Met
    770                 775                 780
Asp Lys Thr Cys Tyr Lys Asp Cys
785                 790

(2) INFORMATION FOR SEQ ID NO:57:

(i) SEQUENCE CHARACTERISTICS:
        (A) LENGTH: 4417 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CAGGCGCAGA GGGGCCCAGA CGACCGTGGA GGATGAAGAA ATAGCCTTGG GACCCTTGGA      60

AAATGAGGCC GCCGCCCCTG CTGCACCTGG CGCTGCTTCT CGCCCTGCCC AGGAGCCTGG    120

GGGGGAAGGG GTGTCCTTCT CCCCCCTGTG AGTGCCACCA GGAGGATGAC TTCAGAGTCA    180

CCTGCAAGGA TATCCACCGC ATCCCCACCC TACCACCCAG CACGCAGACT CTGAAGTTTA    240

TAGAGACTCA GCTGAAAACC ATTCCCAGTC GTGCATTTTC AAATCTGCCC AATATTTCCA    300

GGATCTACTT GTCAATAGAT GCAACTCTGC AGCGGCTGGA ATCACATTCC TTCTACAATT    360

TAAGTAAAAT GACTCACATA GAGATTCGGA ATACCAGAAG CTTAACATCC ATAGACCCTG    420

ACGCCCTAAA AGAGCTCCCA CTCCTGAAGT TCCTTGGCAT TTTCAACACT GGACTTGGAG    480

TATTCCCTGA TGTGACCAAA GTTTATTCCA CTGATGTATT CTTTATACTT GAAATCACAG    540

ACAACCCTTA CATGGCTTCC ATCCCTGCCA ATGCTTTCCA GGGGCTGTGC AATGAAACCC    600

TGACACTGAA ACTATACAAC AATGGCTTTA CTTCAATCCA AGGACATGCT TTCAATGGGA    660

CAAAACTGGA TGCTGTTTAC CTGAACAAGA ATAAATACCT GTCAGCTATC GACAAAGATG    720

CATTTGGAGG AGTGTACAGT GGACCAACCT TGCTGGATGT CTCTTACACC AGTGTTACTG    780

CCCTGCCATC CAAGGCCTG GAGCATCTAA AGGAGCTGAT AGCAAGAAAC ACTTGGACTC    840

TAAAGAAACT CCCACTTTCC TTGAGTTTCC TTCACCTTAC ACGGGCTGAC CTTTCTTATC    900
```

-continued

```
CAAGCCACTG CTGTGCTTTT AAGAATCAGA AGAAAATCAG AGGAATCCTT GAGTCCTTAA    960
TGTGTAATGA AAGCAGTATT CGGAGCCTGC GCCAGAGAAA ATCTGTGAAT ACTTTGAATG   1020
GCCCCTTTGA CCAGGAATAT GAAGAGTATC TGGGTGACAG CCATGCTGGG TACAAGGACA   1080
ACTCTCAGTT CCAGGATACC GATAGCAATT CTCATTATTA TGTCTTCTTC GAAGAACAAG   1140
AAGATGAGAT CCTCGGTTTT GGGCAGGAGC TTAAAAACCC ACAGGAAGAG ACCCTCCAGG   1200
CCTTTGATAG CCATTATGAC TACACTGTGT GTGGTGGCAA TGAAGACATG GTGTGTACTC   1260
CTAAGTCAGA TGAGTTCAAC CCCTGTGAAG ACATAATGGG CTACAAGTTC TGAGGATTG    1320
TGGTGTGGTT TGTTAGTCTG CTGGCTCTCC TGGGCAATGT CTTTGTCCTG ATCGTCCTCC   1380
TTACCAGTCA CTACAAATTG ACTGTCCCAC GCTTTCTCAT GTGCAACTTG GCCTTTGCAG   1440
ATTTCTGCAT GGGGATGTAT CTGCTCCTCA TCGCCTCCGT AGACCTCTAC ACTCATTCTG   1500
AGTACTACAA CCATGCCATC GACTGGCAGA CAGGCCCTGG GTGTAACACA GCTGGTTTCT   1560
TCACTGTCTT TGCCAGTGAA TTATCAGTGT ATACACTGAC AGTCATCACC CTGGAGCGCT   1620
GGTATGCCAT TACCTTCGCC ATGCGCCTGG ACAGGAAGAT CCGCCTCAGG CATGCATATG   1680
CCATCATGGT TGGGGGCTGG GTTTGCTGCT TCCTGCTCGC CCTGCTCCCT CTGGTGGGAA   1740
TAAGCAGCTA TGCCAAGGTC AGCATCTGCC TGCCCATGGA CACTGAGACA CCTCTTGCCC   1800
TGGCATATAT TATCCTTGTT CTGTTGCTCA ACATAGTTGC CTTTATCATT GTCTGCTCCT   1860
GTTATGTGAA GATCTACATC ACAGTCCGAA ATCCCCAGTA CAACCCGGGG GACAAAGACA   1920
CCAAAATTGC CAAAAGGATG GCTGTATTGA TCTTCACTGA CTTCATGTGC ATGGCCCCAA   1980
TCTCATTCTA CGCTCTGTCA GCACTTATGA ACAAGCCTCT CATCACTGTT ACCAACTCCA   2040
AAATCTTGCT GGTTCTCTTC TATCCACTTA ACTCCTGTGC CAATCCATTT CTCTATGCTA   2100
TTTTCACGAA AGCCTTCCAG AGGGATGTAT TTATCCTGCT CAGCAAGTTT GGCATCTGTA   2160
AACGCCAGGC TCAGGCATAC CGGGGCCAGA GGGTTTCTCC AAAGAATAGT GCTGGTATTC   2220
AGATCCAAAA GGTTACCCGG GACATGAGGC AAAGTCTCCC CAACATGCAG GATGAGTATG   2280
AACTGCTTGA AAACTCCCAT CTAACCCCAA ATAAGCAGGG CCAAATCTCA AAAGAGTATA   2340
ACCAAACAGT TCTGTAAGCA GACCCTATAC TACTCGCAGT GGCAGGTGGA CTTCTAAAAA   2400
TCTAGTTTCT TGAACACGTA TTCCAAATTC ATTATATACA CAAGACAGCT GACCTAACCC   2460
TTTGCAGGTG ATGTTTCATG GGGCAAATTT CATCTCCAAA AAGGGGGTAG CTCTACCACC   2520
TAATCATTAC CTCCCAGAAG GAAGAGAGGC TACCAGCACT TCTGAACCCT GGTGATATCA   2580
AGATAACTGA CACTTTCTAG AAAACTTGTT TGATGCTAAC TGCTTTAACA ACATTGTATA   2640
AGATGTCCAA CAGATATTAA CTGAACCAGG TCAACATTGA GCTTCTCACT TTCAAATAGC   2700
ATTTCATAGT AAAGATTCTG CAAATGGCAA ATGCTATTAA CTGAGTTGGT GACCACAAGA   2760
TAGAATTAGC CCCATGTTGG CTTGGTCCAC CTTCATGTTC TTGGATACAA CCAAAGAGAA   2820
TGTGAATTCC TCGAAACTGA AAAGTCCAGC AGGATACATG CATGAAGCAG CTATTATGAG   2880
GTGGAAGGAG GGGAAAGGCT TAGCTTAGTT GTTATTTCAG CCTCTGAAAC TATATCATCT   2940
CTTCACAAGG ACCTACCTGA TGTGACCCAA CTGTTAGGTG TTGCCCAGGG GGGAAAAAAA   3000
CTGGCAAGAT TTCAGCTTAT GTGGCTGAGC AAAGTAAGAA TTGTTCTTCT TGGCTAGTCT   3060
TATAGCATAA AATACGTGAA CCCTAGAAAT ATTTCTAAGT AGCAGCAAGT GGGAATTATG   3120
AGCAGGGCAC ACTAAATCAC ACACTGATTA ATAAAGCAGG GCCACAAGGT AACTGTTGGA   3180
GCTTGGGCAA ATCACTGGGC CACTTCTAAG TCTAGAAATG AGAGAGCCTG ATTGCTTCTT   3240
CAGTTTCAAA ACTCTATGTA TATCCCTTCC CCTTAAAATA TGTTTCCATG ACAAAAAAGA   3300
```

-continued

| | |
|---|---|
| AAAGCACTAA AAAAGAAAAG AAAAGAAAAG CACTAAGAAA GAAAAATTTA TTTTTCCTAT | 3360 |
| CTTGTAGTGC AGCCACCTCT TTCTCTTTGG AGGCTGGATA TATGACCCAG GACATTTCTT | 3420 |
| TCTTTTTTTT ATTTTTTTTT TCATTTTTGA TTATAATGTC TGATCCATGT TGGGCTGGAT | 3480 |
| CTAAATCACT CAACTAATTA CTAGATCTCT ACAGCTACAA TTATCAGGCC AAAAACAGAC | 3540 |
| TCATATTCAC ATAACAGAAT AAAAGGTGGT TTTGCAAATT TTGGTTATTC AGAGTTACTA | 3600 |
| CTTCACTGTA TAGATTAACT TGAAAACATT TAACTTGTCC AGGGATTGGA AGCTATCAAA | 3660 |
| CACTCAGGCA AAGCAACACT AAAGCTATCA AGAGAAGTTT CTTCTCTCCA AAACTGCTAG | 3720 |
| CCTTTTCCAA CCTGTTGATC ATTGGACATA ATCTCTATTG CCCAATAGTG TTCTCTTACT | 3780 |
| TAAAATGGTT AGGATCAATC TTTTAATATA GACGTACTCT TCAGATTACC TGTCAAAACA | 3840 |
| GTCCCTTAAT TTCCTCCCAA GCAGAGATGG CATTTGCTTC TCAATGTTCA TGAAGCACAC | 3900 |
| CAAGGAATTA GAAGCATTTG TTGTTTCAAG TCTGTGGAGT AGGGTTACTG GGCCCAATGC | 3960 |
| CCCCCCCCCC ACAGAGATGG TCCCCCAACC CACCTAGGAT ATCCCAATAG CAATACCCAT | 4020 |
| TTCTGATTAT CATTGAGATT GGACATCTTA GTAGAAATAT TATACACACT CGAAATCATG | 4080 |
| ACTTATCCAC CAGTTCACTT GTAACTAATA ACTAAACAGT TGTGTTATCG TTTGGCATGT | 4140 |
| GTTTCTCACC TGTGACATTT TGAAATAGTA CATCCTGATA ATGTATTTTA TCTTAAGTAG | 4200 |
| TTGAAATAAC ACTTTGGAAA CCGTCCTAGA AAAGTAACTT CAACACAATT GTTACTAAAA | 4260 |
| TTTGCATTCA CAACATGAAA TAAATTTTCT TCCTATGAAA TGATTGTGCT GAGTCCTACA | 4320 |
| GTATGGCATT TTGTAATTTG TGAGCTTCTT TTAATGTTAC CGTTATATGT GTTACAACTG | 4380 |
| AAGACAGGGA AAAAAAAACA ACTGGCAAAT TTGCTAA | 4417 |

(2) INFORMATION FOR SEQ ID NO:58:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

```
Met Arg Pro Pro Pro Leu Leu His Leu Ala Leu Leu Leu Ala Leu Pro
 1               5                  10                  15

Arg Ser Leu Gly Gly Lys Gly Cys Pro Ser Pro Cys Glu Cys His
             20                  25                  30

Gln Glu Asp Asp Phe Arg Val Thr Cys Lys Asp Ile His Arg Ile Pro
             35                  40                  45

Thr Leu Pro Pro Ser Thr Gln Thr Leu Lys Phe Ile Glu Thr Gln Leu
         50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Arg Leu Glu Ser His Ser
                 85                  90                  95

Phe Tyr Asn Leu Ser Lys Met Thr His Ile Glu Ile Arg Asn Thr Arg
            100                 105                 110

Ser Leu Thr Ser Ile Asp Pro Asp Ala Leu Lys Glu Leu Pro Leu Leu
            115                 120                 125

Lys Phe Leu Gly Ile Phe Asn Thr Gly Leu Gly Val Phe Pro Asp Val
        130                 135                 140
```

```
Thr Lys Val Tyr Ser Thr Asp Val Phe Phe Ile Leu Glu Ile Thr Asp
145                 150                 155                 160

Asn Pro Tyr Met Ala Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
                180                 185                 190

Gln Gly His Ala Phe Asn Gly Thr Lys Leu Asp Ala Val Tyr Leu Asn
            195                 200                 205

Lys Asn Lys Tyr Leu Ser Ala Ile Asp Lys Asp Ala Phe Gly Gly Val
210                 215                 220

Tyr Ser Gly Pro Thr Leu Leu Asp Val Ser Tyr Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
                260                 265                 270

Thr Arg Ala Asp Leu
            275

(2) INFORMATION FOR SEQ ID NO:59:

(i) SEQUENCE CHARACTERISTICS:
        (A) LENGTH: 764 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Met Arg Pro Ala Asp Leu Leu Gln Leu Val Leu Leu Asp Leu Pro
1               5                   10                  15

Arg Asp Leu Gly Gly Met Gly Cys Ser Ser Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
50                  55                  60

Arg Thr Ile Pro Ser His Ala Phe Ser Asn Leu Pro Asn Ile Ser Arg
65                  70                  75                  80

Ile Tyr Val Ser Ile Asp Leu Thr Leu Gln Gln Leu Glu Ser His Ser
                85                  90                  95

Phe Tyr Asn Leu Ser Lys Val Thr His Ile Glu Ile Arg Asn Thr Arg
                100                 105                 110

Asn Leu Thr Tyr Ile Asp Pro Asp Ala Leu Lys Glu Leu Pro Leu Leu
            115                 120                 125

Lys Phe Leu Gly Ile Phe Asn Thr Gly Leu Lys Met Phe Pro Asp Leu
130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
                180                 185                 190

Gln Gly Tyr Ala Phe Asn Gly Thr Lys Leu Asp Ala Val Tyr Leu Asn
            195                 200                 205
```

-continued

```
Lys Asn Lys Tyr Leu Thr Val Ile Asp Lys Asp Ala Phe Gly Gly Val
            210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                    245                 250                 255

Thr Trp Thr Leu Lys Lys Leu Pro Leu Ser Leu Ser Phe Leu His Leu
                260                 265                 270

Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                    325                 330                 335

Tyr Lys Glu Lys Ser Lys Phe Gln Asp Thr His Asn Asn Ala His Tyr
                340                 345                 350

Tyr Val Phe Phe Glu Glu Gln Glu Asp Glu Ile Ile Gly Phe Gly Gln
            355                 360                 365

Glu Leu Lys Asn Pro Gln Glu Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                    405                 410                 415

Leu Arg Ile Val Val Trp Phe Val Ser Leu Leu Ala Leu Leu Gly Asn
                420                 425                 430

Val Phe Val Leu Leu Ile Leu Leu Thr Ser His Tyr Lys Leu Asn Val
            435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                    485                 490                 495

Ala Gly Phe Phe Thr Val Phe Ala Ser Glu Leu Ser Val Tyr Thr Leu
                500                 505                 510

Thr Val Ile Thr Leu Glu Arg Trp Tyr Ala Ile Thr Phe Ala Met Arg
            515                 520                 525

Leu Asp Arg Lys Ile Arg Leu Arg His Ala Cys Ala Ile Met Val Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                    565                 570                 575

Pro Leu Ala Leu Ala Tyr Ile Val Phe Val Leu Thr Leu Asn Ile Val
                580                 585                 590

Ala Phe Val Ile Val Cys Cys Cys Tyr Val Lys Ile Tyr Ile Thr Val
            595                 600                 605

Arg Asn Pro Gln Tyr Asn Pro Gly Asp Lys Asp Thr Lys Ile Ala Lys
    610                 615                 620
```

```
Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
                660                 665                 670

Ala Asn Pro Phe Leu Tyr Ala Ile Phe Thr Lys Ala Phe Gln Arg Asp
                675                 680                 685

Val Phe Ile Leu Leu Ser Lys Phe Gly Ile Cys Lys Arg Gln Ala Gln
                690                 695                 700

Ala Tyr Arg Gly Gln Arg Val Pro Pro Lys Asn Ser Thr Asp Ile Gln
705                 710                 715                 720

Val Gln Lys Val Thr His Asp Met Arg Gln Gly Leu His Asn Met Glu
                725                 730                 735

Asp Val Tyr Glu Leu Ile Glu Asn Ser His Leu Thr Pro Lys Lys Gln
                740                 745                 750

Gly Gln Ile Ser Glu Glu Tyr Met Gln Thr Val Leu
                755                 760
```

(2) INFORMATION FOR SEQ ID NO:60:

(i) SEQUENCE CHARACTERISTICS:
        (A) LENGTH: 764 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

```
Met Arg Pro Pro Leu Leu His Leu Ala Leu Leu Ala Leu Pro
1               5                   10                  15

Arg Ser Leu Gly Gly Lys Gly Cys Pro Ser Pro Cys Glu Cys His
                20                  25                  30

Gln Glu Asp Glu Phe Arg Val Thr Cys Lys Asp Ile His Arg Ile Pro
                35                  40                  45

Thr Leu Pro Pro Ser Thr Gln Thr Leu Lys Phe Ile Glu Thr Gln Leu
50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Arg Leu Glu Ser His Ser
                85                  90                  95

Phe Tyr Asn Leu Ser Lys Met Thr His Ile Glu Ile Arg Asn Thr Arg
                100                 105                 110

Ser Leu Thr Ser Ile Asp Pro Asp Ala Leu Lys Glu Leu Pro Leu Leu
                115                 120                 125

Lys Phe Leu Gly Ile Phe Asn Thr Gly Leu Gly Val Phe Pro Asp Val
                130                 135                 140

Thr Lys Val Tyr Ser Thr Asp Val Phe Phe Ile Leu Glu Ile Thr Asp
145                 150                 155                 160

Asn Pro Tyr Met Ala Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
                180                 185                 190

Gln Gly His Ala Phe Asn Gly Thr Lys Leu Asp Ala Val Tyr Leu Asn
                195                 200                 205
```

-continued

```
Lys Asn Lys Tyr Leu Ser Ala Ile Asp Lys Asp Ala Phe Gly Gly Val
    210                 215                 220

Tyr Ser Gly Pro Thr Leu Leu Asp Val Ser Tyr Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
                260                 265                 270

Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
    290                 295                 300

Ser Ile Arg Ser Leu Arg Gln Arg Lys Ser Val Asn Thr Leu Asn Gly
305                 310                 315                 320

Pro Phe Asp Gln Glu Tyr Glu Glu Tyr Leu Gly Asp Ser His Ala Gly
                325                 330                 335

Tyr Lys Asp Asn Ser Gln Phe Gln Asp Thr Asp Ser Asn Ser His Tyr
                340                 345                 350

Tyr Val Phe Phe Glu Glu Gln Glu Asp Glu Ile Leu Gly Phe Gly Gln
            355                 360                 365

Glu Leu Lys Asn Pro Gln Glu Thr Leu Gln Ala Phe Asp Ser His
    370                 375                 380

Tyr Asp Tyr Thr Val Cys Gly Gly Asn Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Ile Val Leu Leu Thr Ser His Tyr Lys Leu Thr Val
                435                 440                 445

Pro Arg Phe Leu Met Cys Asn Leu Ala Phe Ala Asp Phe Cys Ile Gly
    450                 455                 460

Ile Tyr Leu Leu Leu Ile Ala Ser Val Asp Ile His Thr Lys Ser Gln
465                 470                 475                 480

Tyr His Asn Tyr Ala Ile Asp Trp Gln Thr Gly Ala Gly Cys Asp Ala
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp His Thr Ile Thr His Ala Met Gln
        515                 520                 525

Leu Asp Cys Lys Val Gln Leu Arg His Ala Tyr Ser Ala Met Val Gly
    530                 535                 540

Met Trp Ile Phe Ala Phe Ala Ala Ala Leu Phe Pro Ile Phe Gly Ile
545                 550                 555                 560

Ser Ser Tyr Met Lys Val Ser Ile Cys Leu Pro Met Asp Ile Asp Ser
                565                 570                 575

Pro Leu Ser Leu Gln Tyr Val Ile Leu Leu Leu Leu Leu Asn Val Leu
            580                 585                 590

Ala Phe Ile Ile Val Cys Ser Cys Tyr Val Lys Ile Tyr Ile Thr Val
            595                 600                 605

Arg Asn Pro Gln Tyr Asn Pro Gly Asp Lys Asp Thr Lys Ile Ala Lys
    610                 615                 620
```

```
Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
            645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
            690                 695                 700

Ala Tyr Arg Gly Gln Arg Val Ser Pro Lys Asn Ser Ala Gly Ile Gln
705                 710                 715                 720

Ile Gln Lys Val Thr Arg Asp Met Arg Gln Ser Leu Pro Asn Met Gln
                725                 730                 735

Asp Glu Tyr Glu Leu Leu Glu Asn Ser His Leu Thr Pro Asn Lys Gln
                740                 745                 750

Gly Gln Ile Ser Lys Glu Tyr Asn Gln Thr Val Leu
            755                 760

(2) INFORMATION FOR SEQ ID NO:61:

(i) SEQUENCE CHARACTERISTICS:
        (A) LENGTH: 764 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
                20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
50                  55                  60

Arg Thr Ile Pro Ser His Ala Phe Ser Asn Leu Pro Asn Ile Ser Arg
65                  70                  75                  80

Ile Tyr Val Ser Ile Asp Leu Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
            115                 120                 125

Lys Phe Leu Gly Ile Phe Asn Thr Gly Leu Lys Met Phe Pro Asp Leu
130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
            195                 200                 205
```

-continued

```
Lys Asn Lys Tyr Leu Thr Val Ile Asp Lys Asp Ala Phe Gly Gly Val
    210                 215                 220
Tyr Ser Gly Pro Ser Leu Leu Asp Val Ser Gln Thr Ser Val Thr Ala
225                 230                 235                 240
Leu Pro Ser Lys Gly Leu Glu His Leu Lys Glu Leu Ile Ala Arg Asn
                245                 250                 255
Thr Trp Thr Leu Lys Lys Leu Pro Leu Ser Leu Ser Phe Leu His Leu
                260                 265                 270
Thr Arg Ala Asp Leu Ser Tyr Pro Ser His Cys Cys Ala Phe Lys Asn
            275                 280                 285
Gln Lys Lys Ile Arg Gly Ile Leu Glu Ser Leu Met Cys Asn Glu Ser
    290                 295                 300
Ser Met Gln Ser Leu Arg Gln Arg Lys Ser Val Asn Ala Leu Asn Ser
305                 310                 315                 320
Pro Leu His Gln Glu Tyr Glu Glu Asn Leu Gly Asp Ser Ile Val Gly
                325                 330                 335
Tyr Lys Glu Lys Ser Lys Phe Gln Asp Thr His Asn Asn Ala His Tyr
                340                 345                 350
Tyr Val Phe Phe Glu Glu Gln Glu Asp Glu Ile Ile Gly Phe Gly Gln
            355                 360                 365
Glu Leu Lys Asn Pro Gln Glu Glu Thr Leu Gln Ala Phe Asp Ser His
    370                 375                 380
Tyr Asp Tyr Thr Ile Cys Gly Asp Ser Glu Asp Met Val Cys Thr Pro
385                 390                 395                 400
Lys Ser Asp Glu Phe Asn Pro Cys Glu Asp Ile Met Gly Tyr Lys Phe
                405                 410                 415
Leu Arg Ile Val Val Trp Phe Val Ser Leu Leu Ala Leu Leu Gly Asn
                420                 425                 430
Val Phe Val Leu Leu Ile Leu Leu Thr Ser His Tyr Lys Leu Asn Val
            435                 440                 445
Pro Arg Phe Leu Met Cys Asn Leu Ala Phe Ala Asp Phe Cys Met Gly
    450                 455                 460
Met Tyr Leu Leu Leu Ile Ala Ser Val Asp Leu Tyr Thr His Ser Glu
465                 470                 475                 480
Tyr Tyr Asn His Ala Ile Asp Trp Gln Thr Gly Pro Gly Cys Asn Thr
                485                 490                 495
Ala Gly Phe Phe Thr Val Phe Ala Ser Glu Leu Ser Val Tyr Thr Leu
                500                 505                 510
Thr Val Ile Thr Leu Glu Arg Trp Tyr Ala Ile Thr Phe Ala Met Arg
            515                 520                 525
Leu Asp Arg Lys Ile Arg Leu Arg His Ala Ala Ala Ile Met Val Gly
    530                 535                 540
Gly Trp Val Cys Cys Phe Leu Leu Ala Leu Leu Pro Leu Val Gly Ile
545                 550                 555                 560
Ser Ser Tyr Ala Lys Val Ser Ile Cys Leu Pro Met Asp Thr Glu Thr
                565                 570                 575
Pro Leu Ala Leu Ala Tyr Ile Met Ser Val Leu Val Leu Asn Ile Val
                580                 585                 590
Ala Phe Val Ile Cys Cys Cys Tyr Val Lys Ile Tyr Ile Thr Val
            595                 600                 605
Arg Asn Pro Gln Tyr Asn Pro Gly Asp Lys Asp Thr Lys Ile Ala Lys
    610                 615                 620
```

```
Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
            645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
        690                 695                 700

Ala Tyr Arg Gly Gln Arg Val Pro Pro Lys Asn Ser Thr Asp Ile Gln
705                 710                 715                 720

Val Gln Lys Val Thr His Asp Met Arg Gln Gly Leu His Asn Met Glu
            725                 730                 735

Asp Val Tyr Glu Leu Ile Glu Asn Ser His Leu Thr Pro Lys Lys Gln
            740                 745                 750

Gly Gln Ile Ser Glu Glu Tyr Met Gln Thr Val Leu
        755                 760
```

(2) INFORMATION FOR SEQ ID NO:62:

(i) SEQUENCE CHARACTERISTICS:
        (A) LENGTH: 3710 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

```
AGGCAGCAGT TCCTCCTGG GACCTGATGG CTCCCAGATC ACTATCTTGG GCCCAGACTT      60
TCTGGAGCTG AATCTCCAGT TGCCTCGGAG CCTCCTCAGA CTCAGTGTGG CCAGAATGGT    120
GGTCCTGGCT TCCCCTCGGG CCTGCCCTTC TGCCTCCTTC TGCACCCTGA GATGGTCATC    180
AGCTTTTCTC CCACTGCTGC CCTGTATGCA GGGAAGGCCT GCCTGTGGCT GTATCTGTAG    240
TACTTCTTGA ATGTGTTTCC TTCTCCCCCA GGCCAGAGCT GAGAATGAGG CGATTTCGGA    300
GGATGGAGAA ATAGCCCCGA GTCCCGTGGA AAATGAGGCC GGCGGACTTG CTGCAGCTGG    360
TGCTGCTGCT CGACCTGCCC AGGGACCTGG GCGGAATGGG GTGTTCGTCT CCACCCTGCG    420
AGTGCCATCA GGAGGAGGAC TTCAGAGTCA CCTGCAAGGA TATTCAACGC ATCCCCAGCT    480
TACCGCCCAG TACGCAGACT CTGAAGCTTA TTGAGACTCA CCTGAGAACT ATTCCAAGTC    540
ATGCATTTTC TAATCTGCCC AATATTTCCA GAATCTACGT ATCTATAGAT CTGACTCTGC    600
AGCAGCTGGA ATCACACTCC TTCTACAATT TGAGTAAAGT GACTCACATA GAAATTCGGA    660
ATACCAGGAA CTTAACTTAC ATAGACCCTG ATGCCCTCAA AGAGCTCCCC CTCCTAAAGT    720
TCCTTGGCAT TTTCAACACT GGACTTAAAA TGTTCCCTGA CCTGACCAAA GTTTATTCCA    780
CTGATATATT CTTTATACTT GAAATTACAG ACAACCCTTA CATGACGTCA ATCCCTGTGA    840
ATGCTTTTCA GGGACTATGC AATGAAACCT TGACACTGAA GCTGTACAAC AATGGCTTTA    900
CTTCAGTCCA AGGATATGCT TTCAATGGGA CAAAGCTGGA TGCTGTTTAC CTAAACAAGA    960
ATAAATACCT GACAGTTATT GACAAAGATG CATTTGGAGG AGTATACAGT GGACCAAGCT   1020
TGCTGGACGT GTCTCAAACC AGTGTCACTG CCCTTCCATC CAAAGGCCTG GAGCACCTGA   1080
AGGAACTGAT AGCAAGAAAC ACCTGGACTC TTAAGAAACT TCCACTTTCC TTGAGTTTCC   1140
TTCACCTCAC ACGGGCTGAC CTTTCTTACC CAAGCCACTG CTGTGCTTTT AAGAATCAGA   1200
```

```
AGAAAATCAG AGGAATCCTT GAGTCCTTGA TGTGTAATGA GAGCAGTATG CAGAGCTTGC    1260

GCCAGAGAAA ATCTGTGAAT GCCTTGAATA GCCCCCTCCA CCAGGAATAT GAAGAGAATC    1320

TGGGTGACAG CATTGTTGGG TACAAGGAAA AGTCCAAGTT CCAGGATACT CATAACAACG    1380

CTCATTATTA CGTCTTCTTT GAAGAACAAG AGGATGAGAT CATTGGTTTT GGCCAGGAGC    1440

TCAAAAACCC CCAGGAAGAG ACTCTACAAG CTTTTGACAG CCATTATGAC TACACCATAT    1500

GTGGGGACAG TGAAGACATG GTGTGTACCC CCAAGTCCGA TGAGTTCAAC CCGTGTGAAG    1560

ACATAATGGG CTACAAGTTC CTGAGAATTG TGGTGTGGTT CGTTAGTCTG CTGGCTCTCC    1620

TGGGCAATGT CTTTGTCCTG CTTATTCTCC TCACCAGCCA CTACAAACTG AACGTCCCCC    1680

GCTTTCTCAT GTGCAACCTG GCCTTTGCGG ATTTCTGCAT GGGGATGTAC CTGCTCCTCA    1740

TCGCCTCTGT AGACCTCTAC ACTCACTCTG AGTACTACAA CCATGCCATC GACTGGCAGA    1800

CAGGCCCTGG GTGCAACACG GCTGGTTTCT TCACTGTCTT TGCAAGCGAG TTATCGGTGT    1860

ATACGCTGAC GGTCATCACC CTGGAGCGCT GGTATGCCAT CACCTTCGCC ATGCGCCTGG    1920

ACCGGAAGAT CCGCCTCAGG CACGCATGTG CCATCATGGT TGGGGGCTGG GTTTGCTGCT    1980

TCCTCCTCGC CCTGCTTCCT TTGGTGGGAA TAAGTAGCTA TGCCAAAGTC AGTATCTGCC    2040

TGCCCATGGA CACCGAGACC CCTCTTGCTC TGGCATATAT TGTTTTTGTT CTGACGCTCA    2100

ACATAGTTGC CTTCGTCATC GTCTGCTGCT GTTATGTGAA GATCTACATC ACAGTCCGAA    2160

ATCCGCAGTA CAACCCAGGG GACAAAGATA CCAAAATTGC CAAGAGGATG CTGTGTTGA     2220

TCTTCACCGA CTTCATATGC ATGGCCCCAA TCTCATTCTA TGCTCTGTCA GCAATTCTGA    2280

ACAAGCCTCT CATCACTGTT AGCAACTCCA AAATCTTGCT GGTACTCTTC TATCCACTTA    2340

ACTCCTGTGC CAATCCATTC CTCTATGCTA TTTTCACCAA GGCCTTCCAG AGGGATGTGT    2400

TCATCCTACT CAGCAAGTTT GGCATCTGTA AACGCCAGGC TCAGGCATAC CGGGGGCAGA    2460

GGGTTCCTCC AAAGAACAGC ACTGATATTC AGGTTCAAAA GGTTACCCAC GACATGAGGC    2520

AGGGTCTCCA CAACATGGAA GATGTCTATG AACTGATTGA AAACTCCCAT CTAACCCCAA    2580

AGAAGCAAGG CCAAATCTCA GAAGAGTATA TGCAAACGGT TTTGTAAGTT AACACTACAC    2640

TACTCACAAT GCTAGGGGAA CTTACAAAAT AATAGTTTCT TGAATATGCA TTCCAATCCC    2700

ATGACACCCC CAACACATAG CTGCCCTCAC TCTTGTGCAG GCGATGTTTC AATGTTTCAT    2760

GGGGCAAGAG TTTATCTCTG GAGAGTGATT AGTATTAACC TAATCATTGC CCCCAAGAAG    2820

GAAGTTAGGC TACCAGCATA TTTGAATGCC AGGTGAAATC AAAATAATCT ACACTATCTA    2880

GAAGACTTTC TTGATGCCAA GTCCAGAGAT GTCATTGTGT AGGATGTTCA GTAAATATTA    2940

ACTGAGCTAT GTCAATATAG AGCTTCTCAG TTTTGTATAA CATTTCATAC TAAAGATTCA    3000

GCAAATGGAA AATGCTATTA ATTTGGTTGG TGACCACAAG ATAAAATCAG TCCCACGTTG    3060

GCTCAGTTCA ACTAGATGTT CCCTGATACA AAGAGAACTT GATTTCCTTA AAACTGAAAA    3120

GCCAAACACA GCTAGCTGTC ATACAAGAAA CAGCTATTAT GAGACATGAA GGAGGGTAAG    3180

AATTAGCTTT AAGTTTTGTT TTGCTTTGTT TTGTTTTTTA ACTCAACCTA TTAATCATCT    3240

CTTCACAAGA ATCCACCTGA TGTGACCAAG CTATTATGTG TTGCCTGGAA AAACTGGCAA    3300

GATTTCAGCT TATGTGGCCT AGCAAACTAA GAATTGCTCT TCTTGGCCAG CCTCATAGCA    3360

TAAAAGATGT GAACTCTAGG AAGTCTTTCT CAGTAGCAAT AAGTGGGAAT TATGGGCAGA    3420

GCACACTCAA TCCCCTGTTG ATTAATAAAA CAGGCTGGAC ACTAATTAAC TATGGGACTT    3480

AAATCTGTAG AAATGAAGGA GTCCAATAGC TTCTTCCAAT TTTAAAACTC TAGTACATCC    3540

CTTTCCCTCA AATATATATT TCTAAGATAA AGAGAAAGAA GAGCACTAAG TAAGTAGAAT    3600
```

-continued

```
CTGTTTTTCC TATTTTGTAG GGCTGCTGAC TCCTAGTCCT TGAAGCTTAG ACACATGACC    3660

CAGGAAATTT TCCTTTGTTT CACTTTTGAT TATGATGTCT GAGCCAAAAA              3710
```

What is claimed is:

1. Process for the quantitative detection of TSH or of anti-TSHr antibodies comprising the steps of:

contacting intact cells operationally transformed by a vector comprising a cDNA sequence encoding the amino acid sequence represented in SEQ ID NO:50 or membrane preparations of such cells with biological sample suspected of containing TSH or anti-TSHr antibodies;

measuring in the intact cells or membranes the change in adenylyl cyclase activity; and correlating results from the measuring step to the presence of TSH or anti-TSHr antibodies.

2. The process according to claim 1 wherein the cDNA sequence is represented in SEQ ID NO:62.

3. Process for the quantitative detection of TSH or of anti-TSHr antibodies comprising the steps of:

contacting intact cells operationally transformed by a vector comprising a cDNA sequence encoding the amino acid sequence represented in SEQ ID NO:59, or membrane preparations of such cells with a biological sample suspected of containing TSH or anti-TSHr antibodies;

measuring adenylyl cyclase as an indicator of the activating effect of TSH or by "blocking" anti-TSHr antibodies present in the biological sample; and correlating results from the measuring step to the presence of TSH or anti-TSHr antibodies.

4. The process according to claim 3 wherein the cDNA sequence is represented in SEQ ID NO:62.

5. A biologically active preparation of human TSH receptor in the form of an isolated recombinant polypeptide expressed by a transformed host cell, said polypeptide comprising the amino acid sequence set forth in SEQ ID NO:59, and being free of impurities associated with detergent-solubilized thyroid membrane preparations.

6. An isolated cDNA encoding the polypeptide according to claim 5.

7. The isolated nucleotide sequence according to claim 6 characterised in that the sequence is a DNA sequence having the sequence listed in SEQ ID NO:62 (shown in FIG. 12).

8. Process for the preparation of a polypeptide according to claim 5, comprising the steps of:

inserting a vector, which operationally contains a cDNA sequence encoding the polypeptide, into a host cell such that the cell is transformed; and expressing said nucleic acid to obtain said polypeptide.

9. Process for the quantitative detection of anti-thyrotropin receptor antibodies (anti-TSHr) in a biological sample comprising the steps of:

contacting a polypeptide according to claim 5 with the biological sample suspected of containing anti-TSHr antibodies, incubating with labelled TSH, or with labelled anti-TSHr antibodies;

measuring the remaining, bound labelled TSH or bound labelled anti-TSHr antibodies, after competition between the labelled and unlabelled species; and correlating results from the measuring step to the presence of anti-TSHr antibodies.

10. Kit for the detection of anti-TSHr antibodies characterized in that it contains:

a) Polypeptide according to claim 5, having thyrotropin receptor activity and being either in an immobilised or detergent-solubilised form;

b) at least one of the following reagents:
  i) labelled TSH
  ii) labelled anti-TSHr antibodies.

11. Kit according to claim 10, wherein the polypeptide is present in the form of intact cells previously operationally transformed by a vector comprising a cDNA sequence encoding said polypeptide and consequently bearing said polypeptide in their membranes, or in the form of detergent-solubilized membranes of such cells.

* * * * *